US007846663B2

(12) United States Patent
Bartholomeusz et al.

(10) Patent No.: US 7,846,663 B2
(45) Date of Patent: Dec. 7, 2010

(54) HEPATITIS B VIRAL VARIANTS WITH REDUCED SUSCEPTIBILITY TO NUCLEOSIDE ANALOGS AND USES THEREOF

(75) Inventors: Angeline Ingrid Bartholomeusz, Carnegie (AU); Stephen Alister Locarnini, East St. Kilda (AU); Anna Ayres, West Brunswick (AU); Danielle Colledge, Bundoora (AU); Joseph Sasadeusz, Parkville (AU); Peter William Angus, East Ivanhoe (AU); William Sievert, Clayton (AU)

(73) Assignees: Melbourne Health, Victoria (AU); Austin Health, Victoria (AU)

( * ) Notice: Subject to any disclaimer, the term of this patent is extended or adjusted under 35 U.S.C. 154(b) by 0 days.

(21) Appl. No.: 11/932,714

(22) Filed: Oct. 31, 2007

(65) Prior Publication Data

US 2009/0053201 A1      Feb. 26, 2009

Related U.S. Application Data

(63) Continuation of application No. 11/166,004, filed on Jun. 24, 2005, now Pat. No. 7,384,747, which is a continuation of application No. 10/963,333, filed on Oct. 12, 2004, now abandoned, which is a continuation of application No. PCT/AU03/00432, filed on Apr. 11, 2003.

(30) Foreign Application Priority Data

Apr. 12, 2002   (AU) .................................... 1710/02
Jun. 26, 2002   (AU) .................................... 3224/02

(51) Int. Cl.
*C12Q 1/00*      (2006.01)
*C12Q 1/68*      (2006.01)
*C12Q 1/70*      (2006.01)

(52) U.S. Cl. .................................. 435/6; 435/4; 435/5

(58) Field of Classification Search ....................... None
See application file for complete search history.

(56) References Cited

U.S. PATENT DOCUMENTS

| 6,555,311 | B1 | 4/2003 | Locarnini et al. |
| 7,422,848 | B2 | 9/2008 | Bozdayi |
| 2004/0194155 | A1 | 9/2004 | Delaney et al. |

FOREIGN PATENT DOCUMENTS

| AU | 734831 | 6/1998 |
| CA | 2 309 379 | 12/2001 |
| WO | WO 98 21317 A1 | 5/1998 |
| WO | WO 00/61758 | 10/2000 |
| WO | WO 01 57244 A1 | 8/2001 |
| WO | WO 01/94559 | 12/2001 |
| WO | WO 03/066841 | 8/2003 |
| WO | WO 2004/031224 | 4/2004 |

OTHER PUBLICATIONS

Database EMBL [Online] EBI; Hepatitis B virus mutante polymerase gene, Jun. 28, 2000, Yeh C. -T.: XP002510516, retrived from EBI Database accession No. AF156492.
Database EMBL [Online] EBI; Woodchuck hepatitis virus, Sep. 20, 2001, Yamamoto, T: XP002510517, retrived from EBI Database accession No. AF410856.
Miller et al. "Adefovir and tenofovir susceptibilities of HIV-1 after 24 to 48 weeks of adefovir dipivoxil therapy: genotypic and phenotypic analyses of study GS-96-408" 2001, *JAIDS.* , 27(5):450-8.
Stuyver et al. "Nomenclature for antiviral-resistant human hepatitus B virus mutations in the polymerase region" 2001, *Hepatology*, 33(3):751-7.
Villeneuve et al. "Selection of a hepatitis B virus strain resistant to adefovir in a liver transplantation patient" 2003, *J. Hepa.*, 39(6):1085-9.
Xiong et al. "Resistance surveillance of HBeAg-chronic hepatitis B patients treated for 2 years with adefovir dipivoxi" 2003, *J. Hepa.*, 38:182.
Bartholomeusz et al., 1997, "Mutations in the hepatitis B virus polymerase gene that are associated with resistance to famciclovir and lamivudine," *International Antiviral News*, vol. 5, No. 8: p. 123-124.
Estacio et al., 1988, "Nucleotide sequence of a hepatitis B virus genome of subtype adw isolated from a Philippino: Comparison with the reported three genomes of the same subtype," *Journal of Gastroenterology and Hepatology*, vol. 3: p. 215-222.
Stuyver et al., 2001, "Nomenclature for Antiviral-Resistant Human Hepatitis B Virus Mutations in the Polymerase Region," *Hepatology*, Williams and Wilkens, Baltimore, MD, US, vol. 33, No. 3: p. 751-757.
Database UniProt [Online], Jul. 1, 1993; "Protein P [Includes: DNA-directed DNA polymerase (EC<A HREF=" http://srs.ebi.ac.uk/srsbin/cgi-bin/wgetz?[enzyme-ECNumber:2.7.7.49]+-e">2.7.7</A); RNA-directed DNA polymerase (EC < A HREF="http://srs.ebi.ac.uk/srsbin/cig-bin/wgetz?[enzyme-ECNumber:2.7.7.49]+-e">2.7.7.49</A>); Ribonuclease H (EC <A.

(Continued)

Primary Examiner—Zachariah Lucas
(74) Attorney, Agent, or Firm—Baker Botts L.L.P.

(57) ABSTRACT

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide analogs and/or reduced interactivity with antibodies to viral surface components including reduced sensitivity to these antibodies. The present invention further contemplates assays for detecting such viral variants, which assays are useful in monitoring anti-viral therapeutic regimens and in developing new or modified vaccines directed against viral agents and in particular HBV variants. The present invention also contemplates the use of the viral variants to screen for and/or develop or design agents capable of inhibiting infection, replication and/or release of the virus.

3 Claims, 32 Drawing Sheets

OTHER PUBLICATIONS

Gaillard et al., "Kinetic analysis of wild-type and YMDD mutant hepatitis B virus polymerases and effects of deoxyribonucleotide concentrations on polymerase activity," Antimicrob Agents Chemother. 46(4): 1005-1013, 2002.

Colonno et al., "Long-term entecavir treatment results in sustained antiviral efficacy and prolonged life span in the woodchuck model of chronic hepatitis infection," JID 184: 1236-45 2001.

Das et al., "Molecular Modeling and Biochemical Characterization Reveal the Mechanism of Hepatitis B Virus Polymerase Resistance to Lamivudine (3TC) and Emtricitabine (FTC)", J. Virol. 75(10): 4771-4779, 2001.

Delaney et al., "Cross-resistance testing of antihepadnaviral compounds using novel recombinant baculoviruses which encode drug-resistant strains of hepatitis B virus," Antimicrobial Agents Chemother 45(6): 1705-1713, 2001.

Ren and Nassal, "Hepatitis B virus (HBV) virion and covalently closed circular DNA formation in primary tupaia hepatocytes and human hepatoma cell lines upon HBV genome transduction with replication-defective adenovirus vectors," J. Virol. 75(3): 1104-1116, 2001.

Yamanaka et al., "Metabolic studies on BMS-200475, a new antiviral compound active against hepatitis B virus," Antimicrobial Agent Chem 43: 190-193, 1999.

Allen et al., "Identification and characterization of mutations in hepatitis B virus resistant to lamivudine. Lamivudine Clinical Investigation Group," Hepatology 27(6): 1670-1677, 1998.

Genovesi et al., "Efficacy of the carbocyclic 2'-deoxyguanosine nucleoside BMS-200475 in the woodchuck model of hepatitis B virus infection," Antimicrobial Agent Chem 42: 3209-3217, 1998.

Seifer et al., "In Vitro Inhibition of Hepadnavirus Polymerases by the Triphosphates of BMS-200475 and Lobucavir," Antimicrobial Agent Chem 28; 3200-3208, 1998.

Xiong et al., "Mutations in hepatitis B DNA polymerase associated with resistance to lamivudine do not confer resistance to adefovir in vitro," Hepatology. 28(6): 1669-73, 1998.

Aye et al., "Hepatitis B virus polymerase mutations during antiviral therapy in a patient following liver transplantation," J Hepatol. 26: 1148-53, 1997.

Bartholomeusz et al., "Clinical experience with famciclovir against hepatitis B virus," Intervirology 40(5-6): 337-342 1997.

Bisacchi et al., "BMS-200475, a novel carbocyclic 2'-deoxyguanosine analog with potent and selective anti-hepatitis B virus activity in vitro," Bioorg. Med. Chem. Lit. 7: 127-132, 1997.

Innaimo et al., "Identification of BMS-200475 as a potent and selective inhibitor of hepatitis B virus," Antimicrobial Agent Chem 44: 1444-1448, 1997.

Main et al., "double blind, placebo-controlled study to assess the effect of famciclovir on virus replication in patients with chronic hepatitis B virus infection," J. Viral Hepatitis 3: 211-215, 1996.

Dienstag et al., "A preliminary trial of lamivudine for chronic hepatitis B infection," New England J Med 333: 1657-1661, 1995.

Hendricks DA, et al., "Quantitation of HBV DNA in human serum using a branched DNA (bDNA) signal amplification assay," Am J Clin Pathol 104: 537-46, 1995.

Severini et al., "Mechanism of inhibition of duck hepatitis B virus polymerase by (-)- beta-L-2',3'-dideoxy-3'-thiacytidine," Antimicrobial Agents Chemother 39: 1430-1435, 1995.

Kruger et al., "Famciclovir treatment of hepatitis B recurrence after orthotopic liver transplantation-a pilot study [Abstract]," Hepatology 22: 219A, 1994.

Norder et al., "Genetic relatedness of hepatitis B viral strains of diverse geographical origin and natural variations in the primary structure of the surface antigen," (J. Gen. Virol. 74: 1341-1348, 1993.

Vere Hodge, "Famciclovir and penciclovir. The mode of action of famciclovir including its conversion to peciclovir," Antiviral Chem Chemother 4: 67-84, 1993.

Boyd et al., "Antiherpesvirus activity of 9-(4-hydroxy-3-hydroxymethylbut-1-yl) guanine (BRL 39123) in animals," Antiviral Chem Chemother. 32: 358-363, 1987.

Summers and Mason, "Replication of the genome of a hepatitis B—like virus by reverse transcription of an RNA intermediate," Cell 29: 403-415, 1982.

Ono et al., 2001, The polymerase L528M mutation cooperates with nucleotide binding-site mutations, increasing hepatitis B virus replication and drug resistance, J. Clin. Invest 107(4):449-55.

Xiong et al., 2000, In vitro evaluation of hepatitis B virus polymerase mutations associated with famciclovir resistance, Hepatology 31(1):219-224.

Ono-Nita et al., 1999, YMDD motif in hepatitis B virus DNA polymerase influences on replication and lamivudine resistance: A study by in vitro full-length viral DNA transfection, Hepatology 29(3):939-45.

Cane et al., 1999, Analysis of hepatitis B virus quasispecies changes during emergence and reversion of lamivudine resistance in liver transplantation, Antiviral Therapy 4:7-14.

Oon et al., 1999, Hepatitis B virus variants with lamivudine-related mutations in the DNA polymerase and the 'a' epitope of the surface antigen are sensitive to ganciclovir, Antiviral Research 41:113-8.

Delaney et al., 1998, Hepatitis B virus replication in human HepG2 cells mediated by hepatitis B virus recombinant baculovirus, Hepatology 28(4):1134-46.

Gilson et al., "A placebo-controlled phase I/II study of adefovir dipivoxil in patients with chronic hepatitis B virus infection." J Viral Hepat 6: 387-395, 1999.

Perrillo et al., "Adefovir dipivoxil for the treatment of lamivudine-resistant hepatitis B mutants." Hepatology 32: 129-134, 2000.

Peters et al., "Fulminant hepatic failure resulting from lamivudine-resistant hepatitis B virus in a renal transplant recipient: durable response after orthotopic liver transplantation on adefovir dipivoxil and hepatitis B immune globulin." Transplantation 68: 1912-1914, 1999.

Benhamou et al., "Safety and efficacy of adefovir dipivoxil in patients co-infected with HIV-1 and lamivudine-resistant hepatitis B virus: an open-label pilot study." Lancet 358: 718-723, 2001.

Heathcote et al., "Loss of serum HBV DNA and HBeAg and seroconversion following shoert term (12 weeks) Adefovir Dipivoxil therapy in in chronic hepatitis B: two two placebo-controlled phase II studies." Hepatology 28: A620, 1998.

Ying et al., "Inhibition of the replication of the DNA polymerase M550V mutation variant of human hepatitis B virus by adefovir, tenofovir, L-FMAU, DAPD, penciclovir and lobucavir." J Viral Hepat. 7(2). 161-165, 2000.

Ying et al., "Lamivudine, adefovir and tenofovir exhibit long-lasting anti-hepatitis B virus activity in cell culture." J. Viral Hepat. 7(1): 79-83, 2000.

Suo et al., "Selective inhibition of HIV-1 reverse transcriptase by an antiviral inhibitor, (R)-9-(2-Phosphonylmethoxypropyl)adenine." J Biol Chem. 273(42): 27250-27258. 1998.

Frick et al., "Pharmacokinetics, oral bioavailability, and metabolic disposition in rats of (-)-cis-5-fluoro-1-[2-(hydroxymethyl)-1,3-oxathiolan-5-yl] cytosine, a nucleoside analog active against human immunodeficiency virus and hepatitis B virus." Antimicrob Agents Chemother 37: 2285-2292, 1993.

Benzaria et al., "Synthesis, in vitro antiviral evaluation, and stability studies of bis(S-acyl-2-thioethyl) ester derivatives of 9-[2-(phosphonomethoxy)ethyl]adenine (PMEA) as potential PMEA prodrugs with improved oral bioavailability." J Med Chem. 39: 4958-4965, 1996.

Calio et al., "Enhancement of natural killer activity and interferon induction by different acyclic nucleoside phosphonates." Antiviral Res. 23: 77-89, 1994.

Price et al., "Inhibition of the replication of hepatitis B virus by the carbocyclic analogue of 2'-deoxyguanosine." Proc. Natl. Acad. Sci. USA 86(21): 8541-8544, 1989.

Angus et al., "Resistance to adefovir dipivoxil therapy associated with the selection of a novel mutation in the HBV polymerase," Gastroenterology, 125 (2):292-297, 2003.

Bowie et al., "Deciphering the Message in Protein Sequences: Tolerance to Amino Acid Substitutions," Science, 247(4948): 1306-1310, 1990.

Stuyver et al., "Line probe assay for monitoring drug resistance in hepatitis B virus-infected patients during antiviral therapy," Journal of Clinical Microbiology, 38(2): 702-707, 2000.

Zurawski et al., "Definition and spatial location of mouse interleukin-2 residues that interact with its heterotrimeric receptor," The EMBO Journal, 12(13): 5113-5119, 1993.

```
                                                                                                    [SEQ ID NO:8]
                                                                                                    [SEQ ID NO:9]
                                                                                                    [SEQ ID NO:10]
                                                                                                    [SEQ ID NO:11]

ILA1 F, A-E          CAAAACTTGCCAGCAAATCCGCCTCTCCATCYACCAATCGCCAGTCAGGAMGGCAGCCTACCCGCGTGTCTCCACCTTT    80
ILA 2 F,A-E          GCATACTACAAA-CTTTGCCAGCAAATCCGCCTCTCCACCAATCGCCAGTCAGGAAGGCAGCCTACCCGCTGTCTCCACCTTT    88
ILA 3 F, A-E  ACTAGCTCAGGGCATACTACAAAACTTTGCCAGCAAATCCGCCTCTCCACCAATCGCCAGTCAGGAAGGCAGCCTACCCGCTGTCTCCACCTTT   100
ILA 4 F,A-E                                TGCCAGCAAATCCGCCTCTCCATCTACCAATCGCCAGTCGGGACGGCAGCCTACCCGCTGTCTCCACCTTH   73

ILA1 F, A-E    81 GAGAAACACTCATCCTCAGGCCATGCAGTGGAAYTCCACAACCTTCCACAACCTCTGMAAGATCCAGRGTGARAGGCCTGTATTTCCCTGCTGGTGGC 180
ILA 2 F,A-E    89 GAGAAACACTCATCCTCAGGCCATGCAGTGGAATTCCACAACCTTCCACAACCTCTGCAAGATCCAGATCCAGAGTGAGAGGCCTGTATTTCCCTGCTGGTGGC 188
ILA 3 F, A-E  101 GAGAAACACTCATCCTCAGGCCATGCAGTGGAATTCCACAACCTTCCACAACCTCTGCAAGATCCAGATCCAGAGTGAGAGGCCTGTATTTCCCTGCTGGTGGC 200
ILA 4 F,A-E    74 GAGAAACACTCATCCTCAGGCCATGCAGTGGAACTCCACAACCTTCCACAACCTCTGAAAGATCCAGGGTGAGMGGCCTGTATTTCCCTGCTGGTGGC 173

ILA1 F, A-E   181 TCCAGTTCAGGAACAGTAAACCCTGTTCCGACTACTGCCTCTCCCATATCGTCAATCTTCTGAGGATTGGGGACCCTGCGCTGAACATGGAGAACATCA 280
ILA 2 F,A-E   189 TCCAGTTCAGGAACAGTAAACCCTGTTCTGACTACTGCCTCTCCCTTATCGTCAATCTTCTCGAGGATTGGGGACCCTGCGCTGAACATGGAGAACATCA 288
ILA 3 F, A-E  201 TCCAGTTCAGGAACAGTAAACCCTGTTCCGACTACTGCCTCTCCCTTATCGTCAATCTTCTGAGGATTGGGGACCCTGCGCTGAACATGGAGAACATCA 300
ILA 4 F,A-E   174 TCCAGTTCAGGAACAGTAAACCCTGTTCCGACTACTGCCTCTCCCATATCGTCAATCTTCTGAGGATTGGGGACCCTGCGCTGAACATGGAGAACATCA 273

ILA1 F, A-E   281 CATCAGGATTCCTMGACCCTKCTCGTTACAGGCGGGGTTTTTCTTGTTGACAAGAATCCTCACAATACCCAGAGTCTAGACTCGTGGTGGACTTC 380
ILA 2 F,A-E   289 CATCAGGATTCCTAGGACCCTCTCGTGTTACAGGCGGGGTTTTTCTTGTTGACAAGAATCCTCACAATACCCAGAGTCTAGACTCGTGGTGGACTTC 388
ILA 3 F, A-E  301 CATCAGGATTCCTAGGACCCTTCTCGTGTTACAGGCGGGGTTTTTCTTGTTGACAAGAATCCTCACAATACCCAGAGTCTAGACTCGTGGTGGACTTC 400
ILA 4 F,A-E   274 CATCAGGATTCCTCGGACCCTGCTCGTTACAGGCGGGGTTTTTCTTGTTGACAAGAATCCTCACAATACCCAGAGTCTAGACTCGTGGTGGACTTC 373

ILA1 F, A-E   381 TCTCAATTTTCTAGGGGGAACTACCGTGTGTCTTGGCCAAAATTCGCAGTCCCCAACCTCCTGTCCTCCAACTTGTCCTGT 480
ILA 2 F,A-E   389 TCTCAATTTTCTAGGGGGAACTACCGTGTGTCTTGGCCAAAATTCGCAGTCCCCAACCTCCAATCCTGTCCTCCAACTTGTCCTGT 488
ILA 3 F, A-E  401 TCTCAATTTTCTAGGGGGAACTACCGTGTGTCTTGGCCAAAATTCGCAGTCCCCAACCTCCAATCACTCCACCAACTTGTCCTGT 500
ILA 4 F,A-E   374 TCTCAATTTTCTAGGGGGAACTACCGTGTGTCTTGGCCAAAATTCGCAGTCCCCAACCTCCAATCACTCCACCAACTTGTCCTGT 473

ILA1 F, A-E   481 TATCGCTGGATGTGTCTGCGGCGTTTTATCATCTTCCTCTTCATCTTCATCTCTTCATCTCTTCTCTTCTGGTCTTCTTCTGGACTATCAAGGTATGTTGC 580
ILA 2 F,A-E   489 TATCGCTGGATGTGTCTGCGGCGTTTTATCATCTTCCTCTTCATCTTCATCTCTTCATCTCTTCTCTTCTGGTCTTCTTCTGGACTATCAAGGTATGTTGC 588
ILA 3 F, A-E  501 TATCGCTGGATGTGTCTGCGGCGTTTTATCATCTTCCTCTTCATCTTCATCTCTTCATCTCTTCTCTTCTGGTCTTCTTCTGGACTATCAAGGTATGTTGC 600
ILA 4 F,A-E   474 TATCGCTGGATGTGTCTGCGGCGTTTTATCATCTTCCTCTTCATCTTCATCTCTTCATCTCTTCTCTTCTGGTCTTCTTCTGGACTATCAAGGTATGTTGC 573
```

FIG. 4A

[SEQ ID NO:8]
[SEQ ID NO:9]
[SEQ ID NO:10]
[SEQ ID NO:11]

```
ILA1 F, A-E    581  CCGTTTGTCCTCTAATTCCAGGATCTTCAACCACCAGCGGGGAMCATGCAGAACCTGCACGACTACTGCTCAAGGAACCTCTATGTATCCCTCCTGTTG   680
ILA2 F,A-E     589  CCGTTTGTCCTCTAATTCCAGGATCTTCAACCACCAGCGGGGAACCTGCAGAACCTGCACGACTACTGCTCAAGGAACCTCTATGTATCCCTCCTGTTG   688
ILA3 F, A-E    601  CCGTTTGTCCTCTAATTCCAGGATCTTCAACCACCAGCGGGGAACCTGCAGAACCTGCACGACTACTGCTCAAGGAACCTCTATGTATCCCTCCTGTTG   700
ILA4 F,A-E     574  CCGTTTGTCCTCTAATTCCAGGATCTTCAACCACCAGCGGGGAACCTGCAGAACCTGCACGACTACTGCTCAAGGAACCTCTATGTATCCCTCCTGTTG   673

ILA1 F, A-E    681  CTGTACCAAACCTTCGGACGGAAACTGCACCTGTATTCCCATCCTATCCTGGGCTTTCGGAAAATTCCTATGGAGTGGGCCTCAGCCCGTTTCTCC      780
ILA2 F,A-E     689  CTGTACCAAACCTTCGGACGGAAATGCACCTGTATTCCCATCCTATCCTGGGCTTTCGGAAAATTCCTATGGGAGTGGGCCTCAGCCCGTTTCTCC     788
ILA3 F, A-E    701  CTGTACCAAACCTTCGGACGGAAATGCACCTGTATTCCCATCCTATCCTGGGCTTTCGGAAAATTCCTATGGAGTGGGCCTCAGCCCGTTTCTCC      800
ILA4 F,A-E     674  CTGTACCAAACCTTCGGACGGAAACTGCACCTGTATTCCCATCCTATCCTGGGCTTTCGGAAAATTCCTATGGAGTGGGCCTCAGCCCGTTTCTCC     773

ILA1 F, A-E    781  TGGCTCAGTTTACTAGTGCCATTTGTTCAGTGGTTCGTAGGGCTTTCCCCCACTGTTTGGCTTTCAGTTTATACATTTAAACCCTAAACAAAGATGGGTTACTCT   880
ILA2 F,A-E     789  TGGCTCAGTTTACTAGTGCCATTTGTTCAGTGGTTCGTAGGGCTTTCCCCCACTGTTTGGCTTTCAGTTTATACATTTAAACCCTAACAAAACAAAGATGGGTTACTCT  888
ILA3 F, A-E    801  TGGCTCAGTTTACTAGTGCCATTTGTTCAGTGGTTCGTAGGGCTTTCCCCCACTGTTTGGCTTTCAGTTTATACATTTAAACCCTAACAAAACAAAGATGGGTTACTCT  900
ILA4 F,A-E     774  TGGCTCAGTTTACTAGTGCCATTTGTTCAGTGGTTCGTAGGGCTTTCCCCCACTGTTTGGCTTTCAGTTTATATGGATGATGATGTGGTATTGGGGCCAAGTC       873

ILA1 F, A-E    881  TGTAYCAYCTTGAGTCCCTTTTTTACCGCTGTTACCAATTTTCTTTTCTTTGGGTATACATTTAAACCCTAACAAAACTAAAAGATGGGTACTCT    980
ILA2 F,A-E     889  TGTACAGCATCTTGAGTCCTCCTTTTACCGCTGTTACCAATTTTCTTTTCTTTTGTCTTTGGGTATACATTTAAACCCTAACAAAACAAAGAGATGGGTTACTCT   988
ILA3 F, A-E    901  TGTACAGCATCTTGAGTCCTCCTTTTACCGCTGTTACCAATTTTCTTTTCTTTTCTTTGTCTTTGGGCATACATTTAAACCCTAACAAAACAAAGATGGGTACTCT   1000
ILA4 F,A-E     874  TGTACAGCATCTTGAGTCCTCCTTTTACCGCTGTTACCAATTTTCTTTTCTTTTGTCTTTGGGCATACATTTAAACCCTAACAAAACTAAAAGATGGGTACTCT    973

ILA1 F, A-E    981  TTACATTTCATGGNTATGTCATTGGATGTTATGGGTCATTGCCACAAGATCACATCATACAGAAAATCAAAGATGGTTT   1060
ILA2 F,A-E     989  CTAAATTTTATGGTTATGTCATTGGATGTTATGGGTCCTTG   1030
ILA3 F, A-E    1001 CTAAATTTTCATGGTTATGTCATTGGATGTTATGGGTCCTTGCCAAGAACACATACAGAAAAATCAAGAATG   1077
ILA4 F,A-E     974  TTAAATTTCATGGGATATGTCATTGGATGGG    1010
```

FIG. 4B

Patient A polymerase amino acid sequence alignment

```
Pol Trans Pre   1                                          KLASKSASSIXQSPVRXAAYPAVSTFEKHSSSGHAVEXHNLPPNSXRSQXERPVFPCWWLQFRNSKPCSDYCLSHIVNLLEDWGPCAEHGEHH    93    [SEQ ID NO:12]
Pol Trans 2     1                                   HTTNFASKSASCLHQSPVRKAAYPAVSTFEKHSSSGHAVEFHNLPPNSARSQSERPVFPCWWLQFRNSKPCSDYCLSLIVNLLEDWGPCAEHGEHH    96    [SEQ ID NO:13]
Pol Trans 3     1                     LAQGILQNFASKSASCLHQSPVRKAAYPAVSTFEKHSSSGHAVEFHNLPPNSARSQSERPVFPCWWLQFRNSKPCSDYCLSLIVNLLEDWGPCAEHGEHH   100    [SEQ ID NO:14]
Pol Trans 4     1                                             ASKSASSIYQSPVGTAAYPAVSTXEKHSSSGHAVELHNLPPNSERSQGERPVFPCWWLQFRNSKPCSDYCLSHIVNLLEDWGPCAEHGEHH    91    [SEQ ID NO:15]

Pol Trans Pre  94    IRIPRTPXRVTGGVFLVDKNPHNTAESRLVVDFSQFSRGNYRVSWPKFAVPNLQSLTNLLSSNLSWLSLDVSAAFYHLPLHPAAMPHLLVGSSGLSRYVA   193
Pol Trans 2    97    IRIPRTPSRVTGGVFLVDKNPKNTAESRLVVDFSQFSRGNYRVSWPKFAVPNLQSLTNLLSSNLSWLSLDVSAAFYHLPLHPAAMPHLLVGSSGLSRYVA   196
Pol Trans 3   101    IRIPRTPSRVTGGVFLVDKNPHNTAESRLVVDFSQFSRGNYRVSWPKFAVPNLQSLTNLLSSNLSWLSLDVSAAFYHLPLHPAAMPHLLVGSSGLSRYVA   200
Pol Trans 4 of 4 92  IRIPRTPARVTGGVFLVDKNPHNTAESRLVVDFSQFSRGNYRVSWPKFAVPNLQSLTNLLSSNLSWLSLDVSAAFYHLPLHPAAMPHLLVGSSGLSRYVA   191

Pol Trans Pre 194    RLSSNSRIFNHQRGXMQNLHDYCSRNLYVSLLLLYQTFGRKLHLYSHPIILGFRKIPMGVGLSPFLLAQFTSAICSVVRRAFPHCLAFSYMDDVVLGAKS   293
Pol Trans 2   197    RLSSNSRILNNQHGTMPDLHDYCSRNLYVSLLLLYQTFGRKLHLYSHPIILGFRKIPMGVGLSPFLLAQFTSAICSVVRRAFPHCLAFSYMDDVVLGAKS   296
Pol Trans 3   201    RLSSNSRILNNQHGTMPDLHDYCSRNLYVSLLLLYQTFGRKLHLYSHPIILGFRKIPMGVGLSPFLLAQFTSAICSVVRRAFTHCLAFSYMDDVVLGAKS   300
Pol Trans 4   192    RLSSNSRIFNHQRGNMQNLHDCCSRNLYVSLLLLYQTFGRKLHLYSHPIILGFRKIPMGVGLSPFLLAQFTSAICSVVRRAFPHCLAFSYMDDVVLGAKS   291

Pol Trans Pre 294    VXHLESLFTAVTNFLLSLGIHLNPNKTKRMGYSLHFMGYVIGC    336
Pol Trans 2   297    VQHLESLFTAVTNFLLSLGIHLNPNKTKRMGYSLNFMGYVIGCY   340
Pol Trans 3   301    VQHLESLFTAVTNFLLSLGIHLNPNKTKRMGYSLNFMGYVIGCY   344
Pol Trans 4   292    VQHLESLFTAVTNFLLSLGIHLNPNKTKRMGYSLNFMGYVIGWYG  336
```

FIG. 5

Patient A HBsAg Amino acid alignment

```
HBsAg Trans of Pre    1                                                                                             MENITSGFLGPLLVLQA   17  [SEQ ID NO:16]
HBsAg Trans of 2      1   PPPASTNRQSGRQPTPLSPPLRNTHPQAMQWNSTTFHQTLQDPRVRGLYFPAGGSSSGTVNPVLTTASPLSSIFSRIGDPALNMENITSGFLGPLLVLQA  100  [SEQ ID NO:17]
HBsAg Trans of 3      1   PPPASTNRQSGRQPTPLSPPLRNTHPQAMQWNSTTFHQTLQDPRVRGLYFPAGGSSSGTVNPVLTTASPLSSIFSRIGDPALNMENITSGFLGPLLVLQA  100  [SEQ ID NO:18]
HBsAg Trans of 4      1   PPPPSTNRQSGRQPTPLSPPXRNTHPQAMQWNSTTFHQTLSPPXKDPRVXGLYFPAGGSSSGTVNPVPTTASPISSIFSRIGDPALNMENITSGFLGPLLVLQA  100  [SEQ ID NO:19]

HBsAg Trans of Pre   18   GFFLLTRILTIPQSLDSWWTSLNFLGGTTVCLGQNSQSPTSNHSPTSCPPTCPGYRWMCLRRFIIFLFILLLCLIFLLVLLDYQGMLPVCPLIPGSSTTS  117
HBsAg Trans of 2    101   GFFLLTRILTIPQSLDSWWTSLNFLGGTTVCLGQNSQSPTSNHSPTSCPPTCPGYRWMCLRRFIIFLFILLLCLIFLLVLLDYQGMLPVCPLIPGSSTTS  200
HBsAg Trans of 3    101   GFFLLTRILTIPQSLDSWWTSLNFLGGTTVCLGQNSQSPTSNHSPTSCPPTCPGYRWMCLRRFIIFLFILLLCLIFLLVLLDYQGMLPVCPLIPGSSTTS  200
HBsAg Trans of 4    101   GFFLLTRILTIPQSLDSWWTSLNFLGGTTVCLGQNSQSPTSNHSPTSCPPTCPGYRWMCLRRFIIFLFILLLCLIFLLVLLDYQGMLPVCPLIPGSSTTS  200

HBsAg Trans of Pre  118   AGXCRTCTTTAQGTSMYPSCCCTKPSDGNCTCIPIPSSWAFGKFLWEWASARFSWLSLLVPFVQMFVGLSPTWMLSVIWMMWYWGPSLYSXLSPFLPLLP  217
HBsAg Trans of 2    201   TGPCRTCMTTAQGTSMYPSCCCTKPSDGNCTCIPIPSSWAFGKFLWEWASARFSWLSLLVPFVQMFVGLSPTWMLSVIWMMWYWGPSLYSILSPFLPLLP  300
HBsAg Trans of 3    201   TGPCRTCMTTAQGTSMYPSCCCTKPSDGNCTCIPIPSSWAFGKFLWEWASARFSWLSLLVPFVQMFVGLSPTWMLSVIWMMWYWGPSLYSILSPFLPLLP  300
HBsAg Trans of 4    201   AGTCRTCTTTAAQGTSMYPSCCCTKPSDGNCTCIPIPSSWAFGKFLWEWASARFSWLSLLVPFVQMFVGLSPTWMLSVIWMMWYWGPSLYSILSPFLPLLP  300

HBsAg Trans of Pre  218   IFFCLWVYI  226
HBsAg Trans of 2    301   IFFCLWVYI  309
HBsAg Trans of 3    301   IFFCLWVYI  309
HBsAg Trans of 4    301   IFFCLWAYI  309
```

FIG. 6

|   |   |   |   |   |   |   |
|---|---|---|---|---|---|---|
|   | 10 | 20 | 30 | 40 | 50 |   |
| S0 |   |   |   |   |   | [SEQ ID NO:20] |
| S6 |   |   |   |   |   | [SEQ ID NO:21] |
| S8 |   |   |   |   | T | [SEQ ID NO:22] |
| S12 | TTTTGGGGAGCCCTCAGGCTCAGGGCATATTACAAACTCTGCCAGCAAAT | | | | | [SEQ ID NO:23] |
| S15 |   |   |   | TACAAACTTTGCCAGCAAAT | | [SEQ ID NO:24] |

```
              60        70        80        90       100
S0
S6
S8    GCCCCTTCTGCCTCCACCAATCGCCAGTCAGGAAGGCAGCCTACCCCGCT
S12   CCACCTCCTGCCTCCACCAATCGCCAGTCAGGAAGGCAGCCTACCCCGCT
S15   CCACCTCCTGCCTCCACCAATCGCCAGTCAGGAAGGCAGCCTACCCCGCT 110       120       130       140       150
S0
S6
S8    GTCTCCACCTTTGAGAGACACTCATCCTCAGGCCATGCAGTGGAACTCAA
S12   GTCTCCACCTTTGAGAGACACTCATCCTCAGGCCATGCAGTGGAACTCAA
S15   GTCTCCACCTTTGAGAGACACTCATCCTCAGGCCATGCAGTGGAACTCAA 160       170       180       190       200
S0
S6
S8    CAACCTTCCACCAAACTCTGCAAGATCCCAGAGTGAAAGGCCTGTATTTC
S12   CAACCTTCCACCAAACTCTGCAAGATCCCAGAGTGAAAGGCCTGTATTTC
S15   CAACCTTCCACCAAACTCTGCAAGATCCCAGAGTGAAAGGCCTGTATTTC 210       220       230       240       250
S0
S6
S8    CCTGCTGGTGGCTCCAGTTCAGGAACAGTAAACCCTGTTCCGACTACTGC
S12   CCTGCTGGTGGCTCCAGTTCAGGAACAGTAAACCCTGTTCCGACTACTGC
S15   CCTGCTGGTGGCTCCAGTTCAGGAACAGTAAACCCTGTTCCGACTACTGC 260       270       280       290       300
S0
S6
S8    CTCTCACTCATCGTCAATCTTCTCGAGGATTGGGGTCCCTGCGCTGAACA
S12   CTCTCACTCATCGTCAATCTTCTCGAGGATTGGGGTCCCTGCGCTGAACA
S15   CTCTCACTCATCGTCAATCTTCTCGAGGATTGGGGTCCCTGCGCTGAACA
```

FIG.7A

```
            310       320       330       340       350
S0
S6
S8   TGGAGAACATCACATCAGGACTCCTAGGACCCCTTCTCGTGTTACAGGCG
S12  TGGAGAACATCACATCAGGACTCCTAGGACCCCTTCTCGTGTTACAGGCG
S15  TGGAGAACATCACATCAGGACTCCTAGGACCCCTTCTCGTGTTACAGGCG 360       370       380       390       400
S0                                          CGCAGAGTCTAGACTC
S6
S8   GGGTTTTTCTTGTTGACAAGAATCCTCACAATACCGCAGAGTCTAGACTC
S12  GGGTTTTTCTTGTTGACAAGAATCCTCACAATACCGCAGAGTCTAGACTC
S15  GGGTTTTTNTTGTTGACAAGAATCCTCACAATACCGCAGAGTCTAGACTC 410       420       430       440       450
S0   GTGGTGGACTTCTCTCAATTTTCGAGGGGGGACTACCGTGTGTCTTGGCC
S6
S8   GTGGTGGACTTCTCTCAATTTTCGAGGGGGGACTACCGTGTGTCTTGGCC
S12  GTGGTGGACTTCTCTCAATTTTCGAGGGGGGACTACCGTGTGTCTTGGCC
S15  GTGGTGGACTTCTCTCAATTTTCGAGGGGGGACTACCGTGTGTCTTGGCC 460       470       480       490       500
S0   AAAATTCGCAGTCCCCAACCTCCAATCACTCACCAACCTCCTGTCCTCCA
S6                         TTACTCACCNACCTCCTGTCCTCCA
S8   AAAATTCGCAGTCCCCAACCTCCAATCACTCACCAACCTCCTGTCCTCCA
S12  AAAATTCGCAGTCCCCAACCTCCAATCACTCACCAACCTCCTGTCCTCCA
S15  AAAATTCGCAGTCCCCAACCTCCAATCACTCACCAACCTCCTGTCCTCCA 510       520       530       540       550
S0   ACTTGTCCTGGTTATCGCTGGATGTGTCTGCGGCGTTTTATCATCTTCCT
S6   ACTTGTCCTGGTTATCGCTGGATGTGTCTGCGGCGTTTTATCATCTTCCT
S8   ACTTGTCCTGGTTATCGCTGGATGTGTCTGCGGCGTTTTATCATCTTCCT
S12  ACTTGTCCTGGTTATCGCTGGATGTGTCTGCGGCGTTTTATCATCTTCCT
S15  ACTTGTCCTGGTTATCGCTGGATGTGTCTGCGGCGTTTTATCATCTTCCT 560       570       580       590       600
S0   CTTCATCCTGCTGCTATGCCTCATCTTCTTGTTGGTTCTTCTGGACTGTC
S6   CTTCATCCTGCTGCTATGCCTCATCTTCTTGTTGGTTCTTCTGGACTGTC
S8   CTTCATCCTGCTGCTATGCCTCATCTTCTTGTTGGTTCTTCTGGACTGTC
S12  CTTCATCCTGCTGCTATGCCTCATCTTCTTGTTGGTTCTTCTGGACTGTC
S15  CTTCATCCTGCTGCTATGCCTCATCTTCTTGTTGGCTCTACTGGACTGTC 610       620       630       640       650
S0   AAGGTATGTTGCCCGTTTGTCCTCTAATTCCAGGATCCTCAACCACCAGC
S6   AAGGTATGTTGCCCGTTTGTCCTCTAATTCCAGGATCCTCAACCACCAGC
S8   AAGGTATGTTGCCCGTTTGTCCTCTAATTCCAGGATCCTCAACCACCAGC
S12  AAGGTATGTTGCCCGTTTGTCCTCTAATTCCAGGATCCTCAACCACCAGC
S15  AAGGTATGTTGCCCGTTTGTCCTCTAATTCCAGGATCCTCAACCACCAGC
```

FIG. 7B

```
            660       670       680       690       700
S0    ACGGGACCATGCCGAACCTGCACGACTCCTGCTCAAGGAACCTCTACGGT
S6    AGGGGACCATGCCGAACCTGCACGACTCCTGCTCAAGGAACCTCTACGGT
S8    AGGGGACCATGCCGAACCTGCACGACTCCTGCTCAAGGAACCTCTACGGT
S12   AGGGGACCATGCCGAACCTGCACGACTCCTGCTCAAGGAACCTCTACGGT
S15   AGGGGACCATGCCGAACCTGCACGACTCCTGCTCAAGGAACCTCTACGGT 710       720       730       740       750
S0    TCCCTCATGTTGCTGTACCAAACCTTCGGACGGAAATTGCACCTGTATTC
S6    TCCCTCATGTTGCTGTACCAAACCTTCGGACGGAAATTGCACCTGTATTC
S8    TCCCTCATGTTGCTGTACCAAACCTTCGGACGGAAATTGCACCTGTATTC
S12   TCCCTCATGTTGCTGTACCAAACCTTCGGACGGAAATTGCACCTGTATTC
S15   TCCCTCATGTTGCTGTACCAAACCTTCGGACGGAAATTGCACCTGTATTC 760       770       780       790       800
S0    CCATCCCATCATCCTGGGCTTTCGGAAAATTCCTATGGGAGTGGGCCTCA
S6    CCATCCCATCATCCTGGGCTTTCGGAAAATTCCTATGGGAGTGGGCCTCA
S8    CCATCCCATCATCCTGGGCTTTCGGAAAATTCCTATGGGAGTGGGCCTCA
S12   CCATCCCATCATCCTGGGCTTTCGGAAAATTCCTATGGGAGTGGGCCTCA
S15   CCATCCCATCATCCTGGGCTTTCGGAAAATTCCTATGGGAGTGGGCCTCA 810       820       830       840       850
S0    GCCCGTTTCTCCTGGCTCAGTTTACTAGTGCCATTTGTTCAGTGGTTCGT
S6    GCCCGTTTCTCATGGCTCAGTTTACTAGTGCCATTTGTTCAGTGGTTCGT
S8    GCCCGTTTCTCATGGCTCAGTTTACTAGTGCCATTTGTTCAGTGGTTCGT
S12   GCCCGTTTCTCATGGCTCAGTTTACTAGTGCCATTTGTTCAGTGGTTCGT
S15   GCCCGTTTCTCATGGCTCAGTTTACTAGTGCCATTTGTTCAGTGGTTCGT 860       870       880       890       900
S0    AGGGCTTTCCCCCACTGTCTGGCTTTTAGTTATATGGATGATGTGGTATT
S6    AGGGCTTTCCCCCACTGTCTGGCTTTTGGTTATATGGATGATGTGGTATT
S8    AGGGCTTTCCCCCACTGTCTGGCTTTTGGTTATATGGATGATGTGGTATT
S12   AGGGCTTTCCCCCACTGTCTGGCTTTTGGTTATATGGATGATGTGGTATT
S15   AGGGCTTTCCCCCACTGTCTGGCTTTTGGTTATATGGATGATGTGGTATT 910       920       930       940       950
S0    GGGGGCCAAGTCTGTATCGCATCTTGAGTCCCTTTTTACCGCTGNTACCA
S6    GGGGGCCAAGTCTGTATCGCATCTTGAGTCCCTTTTTACCGCTGTTACCA
S8    GGGGGCCAAGTCTGTATCGCATCTTGAGTCCCTTTTTACCGCTGTTACCA
S12   GGGGGCCAAGTCTGTATCGCATCTTGAGTCCCTTTTTACCGCTGTTACCA
S15   GGGGGCCAAGTCTGTATCGCATCTTGAGTCCCTTTTTACCGCTGTTACCA 960       970       980       990       1000
S0    ATTTTCTTTTGTCTTTGGGTATACATTTAAACCCTAACAAAACAAAAAGA
S6    ATTTTCTTTTGTCTTTGGGTATACATTTAAATCCTAACAAAACAAAAAGA
S8    ATTTTCTTTTGTCTTTGGGTATACATTTAAATCCTAACAAAACAAAAAGA
S12   ATTTTCTTTTGTCTTTGGGTATACATTTAAATCCTAACAAAACAAAAAGA
S15   ATTTTCTTTTGTCTTTGGGTATACATTTAAATCCTAACAAAACAAAAAGA
```

FIG.7C

```
             1010       1020       1030       1040       1050
S0    TGGGGTTACTCCCTACATTTTATGGGCTATGTCATTGGAT
S6    TGGGGTTACTCCCTACATTTTATGGGCTATGTCATTGGATGTCATGGGTC
S8    TGGGGTTACTCCCTACATTTTATGGGCTATGTCATTGGATGTCATGGGTC
S12   TGGGGTTACTCCCTACATTTTATGGGCTATGTCATTGGATGTCATGGGTC
S15   TGGGGTTACTCCCTACA 1060       1070       1080       1090       1100
S0
S6    CTTGCCACAAGAACACATCAGACAAAAAATCAAAGAATGTTTTAGAAAAC
S8    CTTGCCACAAGAACACATCAGACAAAAAATCA
S12   CTTGCCACAAGAACACATCAGACAAAAAATCAAAGAATGTTTTAGAAAAC
S15
```

FIG.7D

Patient B Am

```
              260        270        280        290        300
S0    SGHTTNFASKSTSCLHQSPVRKAAYPAVSTFERHSSSGHAVELNNLPPNS   [SEQ ID NO:25]
S6                                                        [SEQ ID NO:26]
S8              CPFCLHQSPVRKAAYPAVSTFERGSSSGHAVELNNLPPNS   [SEQ ID NO:27]
S12   SGHITNSASKSTSCLHQSPVRKAAYPAVSTFERHSSSGHAVELNNLPPNS   [SEQ ID NO:28]
S15         TNFASKSTSCLHQSPVRKAAYPAVSTFERHSSSGHAVELNNLPPNS [SEQ ID NO:29]

310        320        330        340        350
S0    ARSQSERPVFPCWWLQFRNSKPCSDYCLSLIVNLLEDWGPCAEHGEHHIR
S6
S8    ARSQSERPVFPCWWLQFRNSKPCSDYCLSLIVNLLEDWGPCAEHGEHHIR
S12   ARSQSERPVFPCWWLQFRNSKPCSDYCLSLIVNLLEDWGPCAEHGEHHIR
S15   ARSQSERPVFPCWWLQFRNSKPCSDYCLSLIVNLLEDWGPCAEHGEHHIR 360        370        380        390        400
S0    TPRTPSRVTGGVFLVDKNPHNTAESRLVVDFSQFSRGDYRVSWPKFAVPN
S6
S8    TPRTPSRVTGGVFLVDKNPHNTAESRLVVDFSQFSRGDYRVSWPKFAVPN
S12   TPRTPSRVTGGVFLVDKNPHNTAESRLVVDFSQFSRGDYRVSWPKFAVPN
S15   TPRTPSRVTGGVFXVDKNPHNTAESRLVVDFSQFSRGDYRVSWPKFAVPN 410        420        430        440        450
S0    LQSLTNLLSSNLSWLSLDVSAAFYHLPLHPAAMPHLLVGSSGLSRYVARL
S6              SNLSWLSLDVSAAFYHLPLHPAAMPHLLVGSSGLSRYVARL
S8    LQSLTNLLSSNLSWLSLDVSAAFYHLPLHPAAMPHLLVGSSGLSRYVARL
S12   LQSLTNLLSSNLSWLSLDVSAAFYHLPLHPAAMPHLLVGSSGLSRYVARL
S15   LQSLTNLLSSNLSWLSLDVSAAFYHLPLHPAAMPHLLVGSTGLSRYVARL 460        470        480        490        500
S0    SSNSRILNHQHGTMPNLHDSCSRNLYGSLMLLYQTFGRKLHLYSHPIILG
S6    SSNSRILNHQQGTMPNLHDSCSRNLYGSLMLLYQTFGRKLHLYSHPIILG
S8    SSNSRILNHQQGTMPNLHDSCSRNLYGSLMLLYQTFGRKLHLYSHPIILG
S12   SSNSRILNHQQGTMPNLHDSCSRNLYGSLMLLYQTFGRKLHLYSHPIILG
S15   SSNSRILNHQQGTMPNLHDSCSRNLYGSLMLLYQTFGRKLHLYSHPIILG 510        520        530        540        550
S0    FRKIPMGVGLSPFLLAQFTSAICSVVRRAFPHCLAFSYMDDVVLGAKSVS
S6    FRKIPMGVGLSPFLMAQFTSAICSVVRRAFPHCLAFGYVDDVVLGAKSVS
S8    FRKIPMGVGLSPFLMAQFTSAICSVVRRAFPHCLAFGYVDDVVLGAKSVS
S12   FRKIPMGVGLSPFLMAQFTSAICSVVRRAFPHCLAFGYVDDVVLGAKSVS
S15   FRKIPMGVGLSPFLMAQFTSAICSVVRRAFPHCLAFGYVDDVVLGAKSVS
```

FIG.8A

```
        560        570         580         590         600
S0   HLESLFTAXTNFLLSLGIHLNPNKTKRWGYSLHFMGYVIGCHGSXPQEHI
S6   HLESLFTAVTNFLLSLGIHLNPNKTKRWGYSLHFMGYVIG
S8   HLESLFTAVTNFLLSLGIHLNPNKTKRWGYSLHFMGYVIGCHGSLPQEHI
S12  HLESLFTAVTNFLLSLGIHLNPNKTKRWGYSLHFMGYVIG
S15  HLESLFTAVTNFLLSLGXHLNPNKTKRWGYSL
```

FIG.8B

```
            10        20        30        40        50
S0                                                             [SEQ ID NO:30]
S6                                                             [SEQ ID NO:31]
S8                                                             [SEQ ID NO:32]
S12  LGSPQAQGILQTLPANPPPASTNRQSGRQPTPLSPPLRDTHPQAMQWNST         [SEQ ID NO:33]
S15                 PPPASTNRQSGRQPTPLSPPLRDTHPQAMQWNST         [SEQ ID NO:34]

60        70        80        90       100
S0
S6
S8
S12  TFHQTLQDPRVKGLYFPAGGSSSGTVNPVPTTASHSSSIFSRIGVPALNM
S15  TFHQTLQDPRVKGLYFPAGGSSSGTVNPVPTTASHSSSIFSRIGVPALNM 110       120       130       140       150
S0                             QSLDSWWTSLNFRGGTTVCLGQ
S6
S8
S12  ENITSGLLGPLLVLQAGFFLLTRILTIPQSLDSWWTSLNFRGGTTVCLGQ
S15  ENITSGLLGPLLVLQAGFFLLTRILTIPQSLDSWWTSLNFRGGTTVCLGQ 160       170       180       190       200
S0   NSQSPTSNHSPTSCPPTCPGYRWMCLRRFIIFLFILLLCLIFLLVLLDCQ
S6                 PPTCPGYRWMCLRRFIIFLFILLLCLIFLLVLLDCQ
S8                  PTCPGYRWMCLRRFIIFLFILLLCLIFLLVLLDCQ
S12  NSQSPTSNHSPTSCPPTCPGYRWMCLRRFIIFLFILLLCLIFLLVLLDCQ
S15  NSQSPTSNHSPTSCPPTCPGYRWMCLRRFIIFLFILLLCLIFLLALLDCQ 210       220       230       240       250
S0   GMLPVCPLIPGSSTTSTGPCRTCTTPAQGTSTVPSCCCTKPSDGNCTCIP
S6   GMLPVCPLIPGSSTTSRGPCRTCTTPAQGTSTVPSCCCTKPSDGNCTCIP
S8   GMLPVCPLIPGSSTTSRGPCRTCTTPAQGTSTVPSCCCTKPSDGNCTCIP
S12  GMLPVCPLIPGSSTTSRGPCRTCTTPAQGTSTVPSCCCTKPSDGNCTCIP
S15  GMLPVCPLIPGSSTTSRGPCRTCTTPAQGTSTVPSCCCTKPSDGNCTCIP 260       270       280       290       300
S0   IPSSWAFGKFLWEWASARFSWLSLLVPFVQWFVGLSPTVWLLVIWMMWYW
S6   IPSSWAFGKFLWEWASARFSWLSLLVPFVQWFVGLSPTVWLLVMMMMWYW
S8   IPSSWAFGKFLWEWASARFSWLSLLVPFVQWFVGLSPTVWLLVMMMMWYW
S12  IPSSWAFGKFLWEWASARFSWLSLLVPFVQWFVGLSPTVWLLVMMMMWYW
S15  IPSSWAFGKFLWEWASARFSWLSLLVPFVQWFVGLSPTVWLLVMMMMWYW 310       320
S0   GPSLYRILSPFLPLXPIFFCLWVYI
S6   GPSLYRILSPFLPLLPIFFCLWVYI
S8   GPSLYRILSPFLPLLPIFFCLWVYI
S12  GPSLYRILSPFLPLLPIFFCLWVYI
S15  GPSLYRILSPFLPLLPIFFCLWVXI
```

FIG. 9

```
         10         20         30         40         50         60         70         80         90        100
TACTACAAACCTTGCCAGCAAATCGCGCTCCTGCCCTCTACCAATGCCAGTCAGGAAGGCAGCCTACCCCTCTGACTCCTCACCCTTTGAGAAACACTCATCC
        110        120        130        140        150        160        170        180        190        200
TCAGGCCATGCAGTGGAACTGGACATCCACCACAAACTTCCACCGAACTCTACAAGATCCCAGAGTGAAAGGCCTGTATCCCTGCTGGTGGCTCCAGTTCAGGAACA
        210        220        230        240        250        260        270        280        290        300
GTAAACCCTGTCTTCCGACTACTGTCTCTCACACATGCTCAATCTTATGGAGGATTGGGACCCTGCACTGAAGAATGGAGAACATCACATCAGGATTCCTAG
        310        320        330        340        350        360        370        380        390        400
GACCCCCTGCTCGTGTTACAGGCGGGTTTTTCTTGTTGACAAGAATCCTCACAATACCCGAGAGTCTAGACTCCTGTGGACTTCTCTCAATTTCTAGG
        410        420        430        440        450        460        470        480        490        500
GGGGACCACCGTGTGCCTTGGCCAAAATTCGCAGTCCCCAACCTCCAATCACTCACCGGACCCCGTCCTCCAACTGTCCTGGTTATCGCTGGATGTGT
        510        520        530        540        550        560        570        580        590        600
CTGCGGGGTTTATCATATTCCTCTCTTCATCCTGCTATGCCTCATCTTCTTGTGGTTCTTCTCGGACTATCAAGGTATGTGCCCGTTTGCCCTCTAA
        610        620        630        640        650        660        670        680        690        700
TTCCAGGATCCTCAACGCCACCAGCACAGGGACCATGCAGCAGAACCTGCTCAAGGAACCTCTGCTCAAGTGTCATGTGCTACCAAACCTWC
        710        720        730        740        750        760        770        780        790        800
GGMCGSAAATTGCCACCTGTATTCCCATCATCATCCCTGGGCCTTTCGGAAAATTCCTATGGGAGTGGGCCCTCAGCCCGTTTCCTGACTCAGTTTACTA
        810        820        830        840        850        860        870        880        890        900
GTGCCATTTGTTCAGTGGTTCGTAGGGCTTTCCCCCACTGTTTGGCTTTCAGTTATATGGATGATGTGGTATTGGGGCCAGGTCTGTACAGCATGTGA
        910        920        930        940        950        960        970        980        990       1000
GGCCCTTTTACCGGTTACCAATTTCTTTTGTCTCTCGGGTATACATTTAACCCCCGGACAAAACAAAAGATGGGGTTACTCTTTACATTTCATGGGC
       1010       1020       1030
TATGTCATTGGATGTTATGGGTCATTGCCAC
```

FIG. 10

```
        10         20         30         40         50         60         70         80         90        100
TTNLASKSASCLYQSPVRKAAYPSDSTFEKHSSSGHAVELHKLPPNSTRSQSERPVSPCWWLQFRNSKPCSDYCLSHIVNLIEDWGPCTEHGEHHIRIPR
       110        120        130        140        150        160        170        180        190        200
TPARVTGGVFLVDKNPHNTAESRLVVDFSQFSRGDHRVPWPKFAVPNLQSLTNLLSSNLSWLSLDVSAAFYHIPLHPAAMPHLLVGSSGLSRYVARLPSN
       210        220        230        240        250        260        270        280        290        300
SRILNHQHGTMQNLHDSCSRNLY/FVSLMLLYQTF/TGRKLHLYSHPIILGFRKIPMGVGLSPFLLTQFTSAICSVVRRAFPHCLAFSYMDDVVLGARSVQ
       310        320        330        340
HREALFTAVTNFLLSLGIHLTPDKTKRWGYSLHFMGYVIGCYGSLP
```

FIG.11

```
         10         20         30         40         50         60         70         80         90        100
LQTLPANPPPASTNRQSGRQPTPLTPPLRNTHPQAMQWNSTNFHRTLQDPRVKGLYLPAGGSSSGTVNPVPTTVSHTSSILSRIGDPALNMENITSGFLG
        110        120        130        140        150        160        170        180        190        200
PLLVLQAGFFLLTRILTIPQSLDSWWTSLNFLGGTTVCLGQNSQSPTSNHSPTSCPPTCPGYRWMCLRRFIIFLFILLLCLIFLLVLLDYQGMLPVCPLI
        210        220        230        240        250        260        270        280        290        300
PGSSTTSTGPCRTCTTPAQGTSM/LYPSCCCTKPS/TAANCTCIPIPSSWAFGKFLWEWASARFS*LSLLVPFVQWFVGLSPTVWLSVIWMMMYWGPGLYS
        310
IVRPFLPLPIFFCLWYI
```

FIG.12

```
         10        20        30        40        50        60        70        80        90       100
TGGTCACAGTGCCAACAGTTCCTCCTCCTGCCTCCACCAATCGGCAGTCAGGAGGAGGCAGCCTACTCCCATCTCTCCACCTCTAAGAGACAGTCATCCTCA
        110       120       130       140       150       160       170       180       190       200
GGCCATGGTGGCTCAGCCTGCTGGTGGCTCCAGTTCAGGAACACTCAACCCTGTTCCCAATATGCCTCTCACATCTCGTCAATCTCCTTGAGGACTGGG
        210       220       230       240       250       260       270       280       290       300
GACCCTGGCGCCGAACATGGAGAACATCAGGATTCCTAGGACCCCTGCTCGTGTTACAGGGGGTTTTCTTGTTGACAAGAATCCTCACAATAC
        310       320       330       340       350       360       370       380       390       400
CGCAGAGTCTAGACTCGTGGTGGACTTCTCTCAGTTTTCTAGGGGGATCACCCGTGTCTTGGCCAAATTCGCAGTCCCCAACCTCAGTCACTCACC
        410       420       430       440       450       460       470       480       490       500
AACCTCCTGTCCTCCAATTTGACCTGCTGGTTATCGCTGGATATGTCTGCGGGCGTTTATCATATTCCTCTTCATCCTGCCCGCTATGCCTCATCTCTTATTG
        510       520       530       540       550       560       570       580       590       600
GTTCTTCTGGATTATCAAGGTATGTGCCCGTTTGTCCTCTAATTCCAGGATCCCACAACCAGTGCGGGACCCTGCAAAACCTGCACGACTCCTGCTC
        610       620       630       640       650       660       670       680       690       700
AAGGCAACTCTATGTTCCCTCATGTCTGCTACAAAACCTACGGATGGAAATTGCACCTGTATTCCCATCCCATCATCTTGGCCTTTCCGCAAAATACCT
        710       720       730       740       750       760       770       780       790       800
ATGGGAGTGGGCCTCAGTCCGTTTCTCTTGGCTCAGTTTACTAGTGCCATTGTTCAGTGATTCGTAGGGCTTTCCCCACTGTTGGCTTTCAGCTATA
        810       820       830       840       850       860       870       880
TTGATGATGTGCTACTGGGATGCTGCACAACATCTTGAGTCCCTTTATACCGCTGTTACCAATTTCTTTGTCTTTTGGGTAT
```

FIG. 13

```
         10        20         30         40         50         60         70         80         90        100
GHSANSSSSCLHQSAVREAAYSHLSTSKRQSSSGHGGSACWWLQFRNTQPCSQYCLSHLVNLLEDWGPCAEHGEHHIRIPRTPARVTGGVFLVDKNPHNT
        110       120        130        140        150        160        170        180        190        200
AESRLVVDFSQFSRGITRVSWPKFAVPNLQSLTNLLSSNLTWLSLDMSAAFYHIPLHPAAMPHLLIGSSGLSRYVARLSSNSRIHNNQCGTLQNLHDSCS
        210       220        230        240        250        260        270        280        290
RQLYVSLMLLYKTYGWKLHLYSHPIILGFRKIPMGVGLSPFLLAQFTSAICSVIRRAFPHCLAFSYIDDVVLGAKSAQHLESLYTAVTNFLLSLG
```

FIG.14

```
        10         20         30         40         50         60         70         80         90        100
VTVPTVPPASTNRQSGRQPTPISPPLRDSHPQAMVAQPAGGSSSGTLNPVPNIASHISSISLRTGDPAPNMENITSGFLGPLLVLQAGFFLLTRILTIP
       110        120        130        140        150        160        170        180        190        200
QSLDSWWTSLSFLGGSPVCLGQNSQSPTSNHSPTSCPPI*PGYRWICLRRFIIFLFILPCLIFLLVLLDYQGMLPVCPLIPGSTTTSAGPCKTCTTPAQ
       210        220        230        240        250        260        270        280        290
GNSMFPSCCCTKPTDGNCTCIPIPSSWAFAKYLWEWASVRFSWLSLLVPFVQ*FVGLSPTVWLSAILMMYWGPSLHNILSPFIPLLPIFFCLWV
```

FIG. 15

```
         10        20        30        40        50
TCCTGTCCTCCAATTTGTCCTGGTTATCGCTGGATGTGTCTGCGGCGTTT
         60        70        80        90       100
TATGATATTCCTCTTCATCCTGCTGCTATGCCTCATCTTCTTATTGGTTC
        110       120       130       140       150
TTCTGGATTATCAAGGTATGTTGCCCGTCTGTCCTCTAATTCCAGGATCA
        160       170       180       190       200
ACAACAACCAGTACGGGACCATGCAAAACCAAAACCTGCACGACTCCTGC
        210       220       230       240       250
TCAAGGCAACTCTATGTTTCCCTCATGTTGCTGTACAAAACCTACGGATG
        260       270       280       290       300
GAAATTGCACCTGTATTCCCATCCCATCGTCCTGGGCTTTCGCAAAATTC
        310       320       330       340       350
CTATGGGAGTGGGCCTCAGTCCGTTTCTCTTGGCTCAGTTTACTAGTGCC
        360       370       380       390       400
ATTTGTTCAGTGGTTCGTAGGGCTTTCCCCCACTGTTTGGCTTTCAGCTA
        410       420       430       440       450
TATGGATGATGTGGTATTGGGGGCCAAGTCTGTACAGCATCGTGAGGCCC
        460       470       480       490       500
TTTATACAGCTGTTACCAATTTTCTTTTGTCTCTGGGTATACATTTAAAC
        510       520       530       540       550
CCTAACAAAACAAAAGATGGGGTTATTCCCTAAACTTCATGGGTTACAT
        560       570       580       590       600
AATTGGAAGTTGGGGAACATTGCCACAGGATCATATTGTAC
```

FIG.16

```
          10         20         30         40         50
SNLSWLSLDVSAAFYDIPLHPAAMPHLLIGSSGLSRYVARLSSNSRINNN
          60         70         80         90        100
QYGTMQNQNLHDSCSRQLYVSLMLLYKTYGWKLHLYSHPIVLGFRKIPMG
         110        120        130        140        150
VGLSPFLLAQFTSAICSVVRRAFPHCLAFSYMDDVVLGAKSVQHREALTY
         160        170        180
AVTNFLLSLGIHLNPNKTKRWGYSLNFMGYIIGSWG
```

FIG.17

```
          10        20        30        40        50
SCPPICPGYRWMCLRRFMIFLFILLLCLIFLLVLLDYQGMLPVCPLIPGS
          60        70        80        90       100
TTTSTGPCKTKTCTTPAQGNSMFPSCCCTKPTDGNCTCIPIPSSWAFAKF
         110       120       130       140       150
LWEWASVRFSWLSLLVPFVQWFVGLSPTVWLSAIWMMWYWGPSLYSIVRP
         160
FIQLLPIFFCLWVYI
```

FIG. 18

```
        10        20        30        40        50
AATCCTCACAATACCGCAGAGTCTAGACTTCGTGGTGACTTCTCTCAATT
        60        70        80        90       100
TTCTAGGGGACCACCCGTGTGTCTTGGCCAAAATTCGCAGTCCCCAACCT
       110       120       130       140       150
CCAATCACTCACCAACCTCTTGTCCTCCAATTTGTCCTGGTTATCGCTGG
       160       170       180       190       200
ATGTGTCTGCGGCGTTTTATCATATCCCTCTTCATCCTGCTGCTATGCCT
       210       220       230       240       250
CATCTTCTTATTGGTTCTTCTGGATTATCAAGGTATGTTGCCCGTTTGTC
       260       270       280       290       300
CTCTAATTCCAGGATCCACAACAACCAGTACGGGACCCTGCAAAACCTGC
       310       320       330       340       350
ACGACTCCTGCTCAAGGCAACTCTATGTTTCCCTCATGTTGCTGTACAAA
       360       370       380       390       400
ACCTACGGATGGAAATTGCACMTGTATTCCCATCCCATCATCTTGGGCTT
       410       420       430       440       450
TCGCAAAATACCTATGGGAGTGGGCCTCAGTCCGTTTCTCTTGGTTCAGT
       460       470       480       490       500
TTACTAGTGCCATTTGTTCAGTGGTTCGTAGGGCTTTCCCCCACTGTTTG
       510       520       530       540       550
GCTTTCAGCTATATGGATGATATTGTACTGGGGGCCAAGTCTGTACAACA
       560       570       580       590       600
TCTTGAGTCCCTTTATACCGCTGTTACCAATTTTCTTTTGTCTTTGGGTA
       610       620       630       640       650
TACATTTAACCCCTAACAAAACAAAGAGATGGGGTTATTCCCTGAATTTC
       660
ATGGGTTATGTAATTGGAA
```

FIG. 20

```
        10         20         30         40         50
SNLSWLSLDVSAAFYHIPLHPAAMPHLLIGSSGLSRYVARLSSNSRIHNN
        60         70         80         90        100
QYGTLQNLHDSCSRQLYVSLMLLYKTYGWKLHXYSHPIILGFRKIPMGVG
       110        120        130        140        150
LSPFLLVQFTSAICSVVRRAFPHCLAFSYMDDIVLGAKSVQHLESLYTAV
       160        170        180
TNFLLSLGIHLTPNKTKRWGYSLNFMGYVIG
```

FIG.21

```
         10        20        30        40        50
PICPGYRWMCLRRFIISLFILLLCLIFLLVLLDYQGMLPVCPLIPGSTTT
         60        70        80        90       100
STGPCKTCTTPAQGNSMFPSCCCTKPTDGNCTCIPIPSSWAFAKYLWEWA
        110       120       130       140       150
SVRFSWFSLLVPFVQWFVGLSPTVWLSAIWMILYWGPSLYNILSPFIPLL
        160
PIFFCLWVYI
```

FIG.22

```
        10        20        30        40        50
TCCAATTTGTCCTGGGTATCGCTGGATGTGTCTGCGGCGTTTTATCATAT
        60        70        80        90       100
TCCTCTTCATCCTGCTGCTATGCCTCATCTTCTTGTTGGTTCTTCTGGAC
       110       120       130       140       150
TATCAAGGTATGTTGCCCGTTTGTCCTCTACTTCCAGGAACATCAACTAC
       160       170       180       190       200
CAGCACGGGACCATGCAAGACCTGCACGACTCCTGCTCAAGGAACCTCTA
       210       220       230       240       250
TGTTTCCCTCTTGTTGCTGTACAAAACCTTCGGACGGAAATTGCACTTGT
       260       270       280       290       300
ATTCCCATCCCATCGTCTTGGGCTTTCGCAAGATTCCTATGGGAGTGGGC
       310       320       330       340       350
CTCAGTCCGTTTCTCTTGGCTCARTTTACTAGTGCCATTTGTTCAGTGGT
       360       370       380       390       400
TCGTAGGGCTTTCCCCCACTGTTTGGCTTTCAGTTATATTGATGATGTGG
       410       420       430       440       450
TATTGGGGGCCAAGTCTGTACAACATCTTGAATCCCTTTTTACCTCTATT
       460       470       480       490       500
ACCAATTTTCTTATGTCTTTGGGTATACATTTAAACCCTAAGAAAACCAA
       510       520       530       540       550
ACGTTGGGGCTACTCCCTTAACTTCATGGATATGTAATTGGAAGTTGGG

GTAC
```

FIG.23

```
         10        20        30        40        50
SNLSWVSLDVSAAFYHIPLHPAAMPHLLVGSSGLSRYVARLSSTSRNINY
         60        70        80        90       100
QHGTMQDLHDSCSRNLYVSLLLLYKTFGRKLHLYSHPIVLGFRKIPMGVG
        110       120       130       140       150
LSPFLLAQFTSAICSVVRRAFPHCLAFSYIDDVVLGAKSVQHLESLFTSI
        160       170       180
TNFLMSLGIHLNPKKTKRWGYSLNFMGYVIGSWG
```

FIG.24

```
          10        20        30        40        50
PICPGYRWMCLRRFIIFLFILLLCLIFLLVLLDYQGMLPVCPLLPGTSTT
          60        70        80        90       100
STGPCKTCTTPAQGTSMFPSCCCTKPSDGNCTCIPIPSSWAFARFLWEWA
         110       120       130       140       150
SVRFSWLXLLVPFVQWFVGLSPTVWLSVILMMWYWGPSLYNILNPFLPLL
         160
PIFLCLWVYI
```

FIG.25

```
         10        20        30        40        50
CAGCAAATCCGCCTCCTGCCTCTACCAATCGCCAGTCAGGAAGGCAGCCT
         60        70        80        90       100
ACCCCTCTGTCTCCACCTTTGRGAAACACTCATCCTCAGGCCATGCAGTG
        110       120       130       140       150
GAACTCCACAACCTTCCACCAAACTCTGCWAGATCCCAGAGTGAGAGGCC
        160       170       180       190       200
TGTATTTCCCTGCTGGTGGCTCCAGTTCAGGAACAGTAAACCCTGTTCCG
        210       220       230       240       250
ACTTCTGTCTCTCACACATCGTCAATCTTCTCGAGGATTGGGGWCCCTGC
        260       270       280       290       300
GCTGAACATGGAGAACATCACATCAGGATTCCTAGGACCCCTGCTCGTGT
        310       320       330       340       350
TACAGGCGGGGTTTTCTTGTTGACAAGAATCCTCACAATACCGCAGAGT
        360       370       380       390       400
CTAGACTCGTGGTGGACTTCTCTCAATTTTCTAGGGGGAACTACCGTGTG
        410       420       430       440       450
TCTTGGCCAAAATTCGCAGTTCCCAACCTCCAATCACTCACCAACCTCCT
        460       470       480       490       500
GTCCTCCAACTTGWCCTGGTTATCGCTGGATGTRTCTGCGGCGTTTTATC
        510       520       530       540       550
ATCTTCCTCTTCATCCTGCTGCTATGCCTCATCTTCTTGTTGGTTCTTCT
        560       570       580       590       600
GGACTATCAAGGTATGTTGCCCGTTTGTCCTCTARTTCCAGGATCTTCAA
        610       620       630       640       650
CCACCAGCACGGGACCATGCAGAACCTGCACGACTCCTGCTCAAGGAAMC
        660       670       680       690       700
TCTATGAATCCCTCCTGTTGCTGTACCAAACCTTCGGACGGAAATTGCAC
        710       720       730       740       750
CTGTATTCCCATCCCATCATCCTGGGCTTTCGGAAAATTCCTATGGGAGT
        760       770       780       790       800
GGGCCTCAGCCCGTTTCTCCTGRCTCAGTTTACTAGTGCCATTTGTTCAG
        810       820       830       840       850
TGGTTCGTAGGGCTTTCCCCCACTGTTTGGCTTTCAGTTATATGGATGAT
        860       870       880       890       900
GTGGTATTGGGGGCCAAGTCTGTAYMGCATCTTRAGTCCCTTTTTACCGC
        910       920       930       940       950
TGTTACCAATTTTCTTTTGTCTYTGGGTATACATTTAAACCCTMACAAAA
        910       920       930       940      1000
CAAAAAGATGGGGTTACTCTTTACATTTCATGGGCTATGTCATTGGATGT
       1010      1020      1030      1040
TATGGGTCATTGCCACAAGATCACATCAGACAGAAAATCAAAGAA
```

FIG.26

```
          10        20        30        40        50
SKSASCLYQSPVRKAAYPSVSTFXKHSSSGHAVELHNLPPNSARSQSERP
          60        70        80        90       100
VFPCWWLQFRNSKPCSDFCLSHIVNLLEDWGPCAEHGEHHIRIPRTPARV
         110       120       130       140       150
TGGVFLVDKNPHNTAESRLVVDFSQFSRGNYRVSWPKFAVPNLQSLTNLL
         160       170       180       190       200
SSNLXWLSLDVSAAFYHLPLHPAAMPHLLVGSSGLSRYVARLSSXSRIFN
         210       220       230       240       250
HQHGTMQNLHDSCSRXLYESLLLLYQTFGRKLHLYSHPIILGFRKIPMGV
         260       270       280       290       300
GLSPFLLXQFTSAICSVVRRAFPHCLAFSYMDDVVLGAKSVXHLXSLFTA
         310       320       330       340
VTNFLLSLGIHLNPXKTKRWGYSLHFMGYVIGCYGSLPQDHIRQKIKE
```

FIG.27

```
          10        20        30        40        50
ANPPPASTNRQSGRQPTPLSPPLXNTHPQAMQWNSTTFHQTLXDPRVRGL
          60        70        80        90       100
YFPAGGSSSGTVNPVPTSVSHTSSIFSRIGXPALNMENITSGFLGPLLVL
         110       120       130       140       150
QAGFFLLTRILTIPQSLDSWWTSLNFLGGTTVCLGQNSQFPTSNHSPTSC
         160       170       180       190       200
PPTXPGYRWMXLRRFIIFLFILLLCLIFLLVLLDYQGMLPVCPLXPGSST
         210       220       230       240       250
TSTGPCRTCTTPAQGXSMNPSCCCTKPSDGNCTCIPIPSSWAFGKFLWEW
         260       270       280       290       300
ASARFSXLSLLVPFVQWFVGLSPTVWLSVIWMMWYWGPSLYXILSPFLPL
         310
LPIFFCLWVYI
```

FIG.28

HEPATITIS B VIRAL VARIANTS WITH REDUCED SUSCEPTIBILITY TO NUCLEOSIDE ANALOGS AND USES THEREOF

CROSS REFERENCE TO RELATED APPLICATIONS

This application is a continuation of U.S. patent application Ser. No. 11/166,004 filed Jun. 24, 2005, which issued as U.S. Pat. No. 7,384,747 on Jun. 10, 2008, which is a continuation of U.S. patent application Ser. No. 10/963,333 filed Oct. 12, 2004, now abandoned, which is a continuation of International Patent Application No. PCT/AU03/00432, filed Apr. 11, 2003 and published in English on Oct. 23, 2003, as International Patent Publication No. WO03/087351, which claims priority to Australian Patent Application Nos. PS 1710, filed Apr. 12, 2002, and PS 3224, filed Jun. 26, 2002, each of which is by reference incorporated herein in its entirety and to each of which priority is claimed

SEQUENCE LISTING

The specification further incorporates by reference the Sequence Listing submitted herewith via EFS on Jun. 25, 2009. Pursuant to 37 C.F.R. §1.52(e)(5), the Sequence Listing text file, identified as 0718380159seqlist.txt, is 99,799 bytes and was created on Jun. 23, 2009.

BACKGROUND OF THE INVENTION

1. Field of the Invention

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide analogs and/or reduced interactivity with antibodies invention further contemplates assays for detecting such viral variants, which assays are useful in monitoring anti-viral therapeutic regimens and in developing new or modified vaccines directed against viral agents and in particular HBV variants. The present invention also contemplates the use of the viral variants to screen for and/or develop or design agents capable of inhibiting infection, replication and/or release of the virus.

2. Description of the Prior Art

Bibliographic details of the publications referred to in this specification are also collected at the end of the description.

The reference to any prior art in this specification is not, and should not be taken as, an acknowledgment or any form of suggestion that that prior art forms part of the common general knowledge in any country.

Hepatitis B virus (HBV) can cause debilitating disease conditions and can lead to acute liver failure. HBV is a DNA virus which replicates via an RNA intermediate and utilizes reverse transcription in its replication strategy (Summers and Mason, *Cell* 29: 403-415, 1982). The HBV genome is of a complex nature having a partially double-stranded DNA structure with overlapping open reading frames encoding surface, core, polymerase and X genes. The complex nature of the HBV genome is represented in FIG. 1. The polymerase consists of four functional regions, the terminal protein (TP), spacer, reverse transcriptase (rt) and ribonuclease (RNAse).

The polymerase gene of HBV overlaps the envelope gene, mutations in the catalytic domain of the polymerase gene can also affect the nucleotide and the deduced amino acid sequence of the envelope protein and vice versa. In particular, the genetic sequence for the neutralization domain of HBV known as the 'a' determinant, which is found within the HBsAg and located between amino acids 99 and 169, actually overlaps the major catalytic regions of the viral polymerase protein and in particular domains A and B.

The presence of an HBV DNA polymerase has led to the proposition that nucleoside or nucleotide analogs could act as effective anti-viral agents. Examples of nucleoside analogs currently being tested are penciclovir and its oral form (FCV) [Vere Hodge, *Antiviral Chem Chemother* 4: 67-84, 1993; Boyd et al., *Antiviral Chem. Chemother.* 32: 358-363, 1987; Kruger et al., *Hepatology* 22: 219A, 1994; Main et al., *J. Viral Hepatitis* 3: 211-215, 1996], Lamivudine[(–)-β-2'-deoxy-3'-thiacytidine]; (3TC or LMV) [Severini et al., *Antimicrobial Agents Chemother.* 39: 430-435, 1995; Dienstag et al., *New England J Med* 333: 1657-1661, 1995]. New nucleoside or nucleotide analogs which have already progressed to clinical trials include the pyrimidines Emtricitabine, ((–)-β-L-2'-3'-dideoxy-5-fluoro-3'-thiacydidine; FTC), the 5-fluoro derivative of 3TC, and Clevudine (1-(2-fluoro-5-methyl-β-L-arabino-furanosyl) uracil; L-FMAU), a thymidine analog. Like 3TC, these are pyrimidine derivatives with an unnatural "L"-configuration. Several purine derivatives have also progressed to clinical trials; they include Entecavir (BMS-200, 475; ETV), a carbocyclic deoxyguanosine analog, diaminopurine dioxolane (DAPD), an oral pro-drug for dioxolane guanine ((–)-β3-D-2-aminopurine dioxolane; DXG) and Adefovir dipivoxil, an oral prodrug for the acyclic deoxyadenosine monophosphate nucleoside analog Adefovir (9-[phosphonyl-methoxyethyl]-adenine; PMEA). Other drugs in pre-clincial and clinical trials include FLG [Medivir], ACH-126,443 (L-d4C) [Archillion Pharmaceuticals], ICN 2001-3 (ICN) and Racivir (RCV) [Pharmassett].

Whilst these agents are highly effective in inhibiting HBV DNA synthesis, there is the potential for resistant mutants of HBV to emerge during long term antiviral chemotherapy. In patients on prolonged LMV therapy, key resistance mutations are selected in the rt domain within the polymerase at rtM204I/V+/−rtL180M as well as other mutations. The nomenclature used for the polymerase mutations is in accordance with that proposed by Stuyver et al., 2001, supra. LMV is a nucleoside analog that has been approved for use against chronic HBV infection. LMV is a particularly potent inhibitor of HBV replication and reduces HBV DNA titres in the sera of chronically infected patients after orthotopic liver transplantation (OLT) by inhibiting viral DNA synthesis. LMV monotherapy seems unlikely to be able to control HBV replication in the longer term. This is because emergence of LMV-resistant strains of HBV seems almost inevitable during monotherapy.

Adefovir dipivoxil (ADV: formerly, bis-pom PMEA) is an orally available prodrug of the acyclic deoxyadenosine monophosphate analog adefovir (formerly, PMEA) (FIG. 2). ADV is also a potent inhibitor of HBV replication and has recently been given FDA approval for use against chronic HBV infection. Adefovir dipivoxil differs from other agents in this class in that it is a nucleotide (vs. nucleoside) analog and as such bypasses the first phosphorylation reaction during drug activation. This step is often rate-limiting. Adefovir dipivoxil has demonstrated clinical activity against both wild-type and lamivudine-resistant strains of HBV and is currently in phase III clinical Testing (Gilson et al., *J Viral Hepat* 6: 387-395, 1999; Perrillo et al., *Hepatology* 32: 129-134, 2000; Peters et al., *Transplantation* 68: 1912-1914, 1999; Benhamou et al., *Lancet* 358: 718-723, 2001). During phase II studies a 30 mg daily dose of adefovir dipivoxil resulted in a mean 4 log$_{10}$ decrease in viremia over 12 weeks (Heathcote et al, *Hepatology* 28: A620, 1998).

ADV is a substituted acyclic nucleoside phosphonate. This class of compounds also includes tenofovir disoproxil fumarate (also referred to as tenofovir DF, or tenofovir, or (TFV) or 9-R-(2-phosphonomethoxypropyl)adenine (PMPA) and is marketed as Viread by Gilead sciences).

TFV has antiviral activity against both HBV and HIV (Ying et al, *J Viral Hepat.* 7(2): 161-165, 2000; Ying et al, *J. Viral Hepat.* 7(1): 79-83, 2000; Suo et al., *J Biol. Chem.* 273(42): 27250-27258.1998).

FTC has activity against HBV and HIV (Frick et al., *Antimicrob Agents Chemother* 37: 2285-2292, 1993).

Nucleoside or nucleotide analog therapy may be administered as monotherapy or combination therapy where two or more nucleoside or nucleotide analogs may be administered. The nucleoside or nucleotide analogs may also be administered in combination with other antiviral agents such as interferon or hepatitis B immunoglobulin (HBIG).

There is a need to monitor for the emergence of nucleoside/ nucleotide-analog- or antibody-resistant strains of HBV and to develop diagnostic protocols to detect these resistant viruses and/or to use them to screen for and/or develop or design agents having properties making them useful as antiviral agents. Defective forms of these resistant strains or antigenic components therefrom are also proposed to be useful in the development of therapeutic vaccine compositions as are antibodies directed to viral surface components.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

Specific mutations in an amino acid sequence are represented herein as "Xaa$_1$nXaa$_2$" where Xaa$_1$ is the original amino acid residue before mutation, n is the residue number and Xaa$_2$ is the mutant amino acid. The abbreviation "Xaa" may be the three letter or single letter (i.e. "X") code. An "rt" before "Xaa$_1$nXaa$_2$" means "reverse transcriptase". An "s" means an envelope gene. The amino acid residues for HBV DNA polymerase are numbered with the residue methionine in the motif Tyr Met Asp Asp (YMDD) being residue number 204 (Stuyver et al., *Hepatology* 33: 751-757, 2001). The amino acid residues for hepatitis B virus surface antigen are number according to Norder et al. (*J. Gen. Virol.* 74: 341-1348, 1993). Both single and three letter abbreviations are used to define amino acid residues and these are summarized in Table 2.

In accordance with the present invention, the selection of HBV variants is identified in patients (Patient A, C and D) with chronic HBV infection treated with ADV and liver transplant patients (Patients B and E) treated with both ADV and LMV post-OLT or ADV post-transplant. HBV variants from Patients F, G and H were also identified following similar treatments. Variants of HBV are identified during ADV or combination ADV and LMV treatment with mutations in the HBV DNA polymerase gene which reduce the sensitivity of HBV to this nucleoside analog. Consequently, HBV rt variants are contemplated which are resistant to, or which exhibit reduced sensitivity to, ADV, LMV, TFV, FTC, ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combinations thereof. Corresponding mutations in the surface antigen also occur. The identification of these HBV variants is important for the development of assays to monitor ADV, LMV, FTC and/or TFV resistance and/or resistance to other nucleoside or nucleotide analogs or other anti-HBV agents or combinations thereof and to screen for agents which are useful as alternative therapeutic agents.

Reference herein to "anti-HBV agents" includes nucleoside and nucleotide analogs as well as immunological reagents (e.g. antibodies to HBV surface components) and chemical, proteinaceous and nucleic acid agents which inhibit or otherwise interfere with viral replication, maintenance, infection, assembly or release.

The detection of such HBV variants is particularly important in the management of therapeutic protocols including the selection of appropriate agents for treating HBV infection. The method of this aspect of the present invention is predicated in part on monitoring the development in a subject of an increased HBV load in the presence of a nucleoside or nucleotide analog or other anti-HBV agents or combinations thereof. The clinician is then able to modify an existing treatment protocol or select an appropriate treatment protocol accordingly.

Accordingly, one aspect of the present invention is directed to an isolated HBV variant comprising a nucleotide mutation in a gene encoding a DNA polymerase resulting in at least one amino acid addition, substitution and/or deletion to the DNA polymerase and which exhibits decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combinations thereof. The variant HBV comprises a mutation in an overlapping open reading frame in its genome in a region defined by one or more of domains F and G and domain A through to E of HBV DNA polymerase.

Another aspect of the present invention provides an isolated HBV variant comprising a nucleotide mutation in the S gene resulting in at least one amino acid addition, substitution and/or deletion to the surface antigen and which exhibits decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, or ADV and FTC and LMV and TFV, ADV and LMV and FTC, and/or optionally other nucleoside or nucleotide analogs or other anti-HBV agents or combinations thereof.

Useful mutants in the rt region include, in one embodiment, rtS21A, rtL122F, rtN124H, rtH126R, rtT28N, rtP130Q, rtD131N and rtY135C; in another embodiment, rt/N/S/T/I/ V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; and in yet another embodiment, rtH90D and rtL/F108L; and in still a further embodiment, rtL157L/M, rtA181V and rtV207I and in yet a further embodiment, rtL80V, rtP109S, rtI163V, rtL229M and rtN/H/A/S/Q238K; and in another embodiment, rtS78S/T, rtN118N/S, rtN139N/K, rtV142E, rtA181A/T, rtI204M, rtQ/P/S/Stop215Q, rtE218K/E and rtN238N/H or a combination thereof or an equivalent mutation.

Other HBV variants are also contemplated with mutations in rt at rtK32, rtN33, rtP34, rtH35 and rtT37 (these are upstream of the F domain of the DNA polymerase), rtP59, rtK60, rtF61, rtA62 and rtV63 (these are located between the F and A domains), rtD83, rtV84, rtS85, rtA86, rtY89, rtH90 and rtI/L91 (these are located within the A domain and the region immediately prior to and following), rtP177, rtF178, rtL179, rtL180, rtA181, rtQ182, rtF183 and rtT184 (these are located in the B domain), rtM204 and rtY203 (these are located in the C domain), rt235, rt236, rt237, rt238 and rt239 (these are located in the D domain) and rt247, rt248, rt249, rt250 and rt251 (these are located in the E domain) or a combination thereof or an equivalent mutation.

Useful mutants are provided below (see also Tables 16 and 17):

K32M/F/P/S/T/W/Y/V/A/R/N/D/C/Q/E/G/H/I/L/deletion;
N33D/C/Q/E/G/H/I/L/K/M/F/P/S/T/W/Y/V/A/R/deletion;
P34S/T/W/Y/V/A/R/N/D/C/Q/E/G/H/I/L/K/M/F/deletion;
H35I/L/K/M/F/P/S/T/W/Y/V/A/R/N/D/C/Q/E/G/deletion;
T37W/Y/V/A/R/N/D/C/Q/E/G/H/I/L/K/M/F/P/S/deletion;
P59S/T/W/Y/V/A/R/N/D/C/Q/E/G/H/I/L/K/M/F/deletion;
K60M/F/P/S/T/W/Y/V/A/R/N/D/C/Q/E/G/H/I/L/deletion;
F61P/S/T/W/Y/V/A/R/N/D/C/Q/E/G/H/I/L/K/M/deletion;
A62R/N/D/C/Q/E/G/H/I/L/K/M/F/P/S/T/W/Y/V/deletion;
V63A/R/N/D/C/Q/E/G/H/I/L/K/M/F/P/S/T/W/Y/deletion;
D83C/Q/E/G/H/I/L/K/M/F/P/S/T/W/Y/V/A/R/N/deletion;
V84A/R/N/D/C/Q/E/G/H/I/L/K/M/F/P/S/T/W/Y/deletion;
S85T/W/Y/V/A/R/N/D/C/Q/E/G/H/I/L/K/M/F/P/deletion;
A86R/N/D/C/Q/E/G/H/I/L/K/M/F/P/S/T/W/Y V/deletion;
Y89V/A/R/N/D/C/Q/E/G/H/I/L/K/M/F/P/S/T/W/deletion;
H90I/L/K/M/F/P/S/T/W/Y/V/A/R/N/D/C/Q/E/G/deletion;
I/L91K/M/F/P/S/T/W/Y/V/A/R/N/D/C/Q/E/G/H/deletion;
P177S/T/W/Y/V/A/R/N/D/C/Q/E/G/H/I/L/K/M/F/deletion;
F178P/S/T/W/Y/V/A/R/N/D/C/Q/E/G/H/I/L/K/M/deletion;
L179K/M/F/P/S/T/W/Y/V/A/R/N/D/C/Q/E/G/H/I/deletion;
L180K/M/F/P/S/T/W/Y/V/A/R/N/D/C/Q/E/G/H/I/deletion;
A181R/N/D/C/Q/E/G/H/I/L/K/M/F/P/S/T/W/Y/V/deletion;
Q183E/G/H/I/L/K/M/F/P/S/T/W/Y/V/A/R/N/D/C/deletion;
F183P/S/T/W/Y/V/A/R/N/D/C/Q/E/G/H/I/L/K/M/deletion;
T184W/Y/V/A/R/N/D/C/Q/E/G/H/I/L/K/M/F/P/S/deletion;
Y203V/A/R/N/D/C/Q/E/G/H/I/L/K/M/F/P/S/T/W/deletion;
M204F/P/S/T/W/Y/V/A/R/N/D/C/Q/E/G/H/I/L/K/deletion;
L235K/M/F/P/S/T/W/Y/V/A/R/N/D/C/Q/E/G/H/I/deletion;
N236D/C/Q/E/G/H/I/L/K/F/P/S/T/W/Y/V/A/R/deletion;
T237W/Y/V/A/R/N/D/C/Q/E/G/H/I/L/K/M/F/P/S/deletion;
P237S/T/W/Y/V/A/R/N/D/C/Q/E/G/H/I/L/K/M/F/deletion;
N238D/C/Q/E/G/H/I/L/K/M/F/P/S/T/W/Y/V/A/R/deletion;
H238I/L/K/M/F/P/S/T/W/Y/V/A/R/N/D/C/Q/E/G/deletion;
A238R/N/D/C/Q/E/G/H/I/L/K/M/F/P/S/T/W/Y/V/deletion;
S239T/W/Y/V/A/R/N/D/C/Q/E/G/H/I/L/K/M/F/P/deletion;
Q238E/G/H/L/K/M/F/P/S/T/W/Y/V/A/R/N/D/C/deletion;
K239M/F/P/S/T/W/Y/V/A/R/N/D/C/Q/E/G/H/I/L/deletion;
L247K/M/F/P/S/T/W/Y/V/A/R/N/D/C/Q/E/G/H/I/deletion;
N248D/C/Q/E/G/H/I/L/K/M/F/P/S/T/W/Y/V/A/R/deletion;
H248I/L/K/M/F/P/S/T/W/Y/V/A/R/N/D/C/Q/E/G/deletion;
F249P/S/T/W/Y/V/A/R/N/D/C/Q/E/G/H/I/L/K/M/deletion;
M250F/P/S/T/W/Y/V/A/R/N/D/C/Q/E/G/H/I/L/K/deletion;
G251H/I/L/K/M/F/P/S/T/W/Y/V/A/R/N/D/C/Q/E/deletion; and
V251A/R/N/D/C/Q/E/G/H/I/L/K/M/F/P/S/T/W/Y/deletion.

Reference above to "deletion" means that the first mentioned amino acid before the residue number has been deleted.

Useful mutations in the S gene include, in one embodiment, sP120T, sM125T and sT127A; in another embodiment, T118R, sM133T, sF134V sI195M, sS207R and sY225Y/C; in a further embodiment, sS126T, sM133L/M, sS143S/T, sD144A sG145A and sW172Stop; in yet a further embodiment, sN40S, sC69 Stop, sM75I, sL88P, sT118A, sW182stop, sW196L, sY206H and sY225F; and in yet another embodiment, sI81M and sP214Q; and in still another embodiment, sF83S, sL173F and sW199L; and in still yet another embodiment, sI126T, sK160R, sS174N, sA184V, sW196L, sS210N, sF/C220L and sY221C; and in yet another embodiment, sC69Stop/C, sC76Y sI110V/I, sY134N, sW172Stop/W, sW196Stop and sS207R or a combination thereof or an equivalent mutation.

The present invention further contemplates a method for determining the potential for an HBV to exhibit reduced sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof by isolating DNA or corresponding mRNA from the HBV and screening for a mutation in the nucleotide sequence encoding HBV DNA polymerase resulting in at least one amino acid substitution, deletion and/or addition in any one or more of domains F and G and domains A through to E or a region proximal thereto of the DNA polymerase and associated with resistance or decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof. The presence of such a mutation is an indication of the likelihood of resistance to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

The present invention also provides a composition comprising a variant HBV resistant to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, or ADV and FTC and LMV and TFV, ADV and LMV and FTC, and/or optionally other nucleoside or nucleotide analogs or other anti-HBV agents or combination thereof or an HBV surface antigen from the variant HBV or a recombinant or derivative form thereof or its chemical equivalent and one or more pharmaceutically acceptable carriers and/or diluents.

Yet another aspect of the present invention provides a use of the aforementioned composition or a variant HBV comprising a nucleotide mutation in a gene encoding a DNA polymerase resulting in at least one amino acid addition, substitution and/or deletion to the DNA polymerase and a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof in the manufacture of a medicament for the treatment and/or prophylaxis of hepatitis B virus infection.

The present invention also contemplates a method for determining whether an HBV strain exhibits reduced sensitivity to a nucleoside or nucleotide analog or other anti-HBV agents or by isolating DNA or corresponding mRNA from the HBV and screening for a mutation in the nucleotide sequence encoding the DNA polymerase wherein the presence of the following mutations in the rt region: in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment, rtH90D and rtL/F108L, in even yet another embodiment, rtL157L/M, rtA181V and rtV207I; in still yet another embodiment, rtL80V, rtP109S, rtI163V, rtL229M and rtN/H/A/S/Q238K; in another embodiment, rtS78S/T, rtN118N/S, rtN139N/K, rtV142E, rtA181A/T, rtI204M, rtQ/P/S/Stop215Q, rtE218K/E and rtN238N/H; in a further embodiment, rtK32, rtN33, rtP34, rtH35 and rtT37; in yet another embodiment, rtP59, rtK60, rtF61, rtA62 and rtV63; in still another embodiment, rtD83, rtV84, rtS85, rtA86, rtY89, rtH90 and rtI/L91; in even yet another embodiment, rtP177, rtF178, rtL179, rtL180, rtA181, rtQ182, rtF183 and rtT184; in still yet another embodiment, rtM204 and rtY203; in another embodiment, rt235, rt236, rt237, rt238 and rt239; in a further embodiment, rt247, rt248, rt249, rt250 and rt251 or combinations thereof or an equivalent one or more other mutation is indicative of a variant which exhibits a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

Still a further methodology comprises screening for a mutation in the nucleotide sequence encoding the envelope genes (s) wherein the presence of the following mutations in the S gene: in one embodiment, sP120T, sM125T and sT127A; in another embodiment, sT118R, sM133T, SF134V, sI195M, sS207R and sY225Y/C; in a further embodiment, sS126T, sM133L/M, sS143S/T, sD144A, sG145A and sW172Stop in yet another embodiment, sN40S, sC69Stop, sM75I, sL88P, sT118A, sW182Stop, sW196L, sY206H and sY225F; in still yet another embodiment, s181M and sP214Q; in another embodiment, sF83S, sL173F and sW199L; in a further aspect, sI126T, sK160R, sS174N, sA184V, sW196L, sS210N, sF/C220L and sY221C; in a further embodiment, sC69Stop/C, sC76Y, sI110V/I, sY134N, sW172Stop/W, sW196Stop and sS207R or combinations thereof or an equivalent one or more other mutation is indicative of a variant which exhibits a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV, and/or optionally other nucleoside or nucleotide analogs or other anti-HBV agents or combination thereof.

Preferably, the variants are in an isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions.

Another aspect of the present invention is directed to a variant HBV comprising a surface antigen having an amino acid sequence with a single or multiple amino acid substitution, addition and/or deletion or a truncation compared to a surface antigen from a reference or wild type HBV and wherein an antibody generated to the reference or wild type surface antigen exhibits an altered immunological profile relative to the HBV variant. One altered profile includes a reduced capacity for neutralizing the HBV. More particularly, the surface antigen of the variant HBV exhibits an altered immunological profile compared to a pre-treatment HBV where the variant HBV is selected for by a nucleoside or nucleotide analog or other anti-HBV agents of the HBV DNA polymerase. The variant HBV of this aspect of the invention may also comprise a nucleotide sequence comprising a single or multiple nucleotide substitution, addition and/or deletion compared to a pre-treatment HBV.

The present invention extends to an isolated HBsAg or a recombinant form thereof or derivative or chemical equivalent thereof corresponding to the variant HBV. Generally, the HBsAg or its recombinant or derivative form or its chemical equivalent comprises an amino acid sequence with a single or multiple amino acid substitution, addition and/or deletion or a truncation compared to an HBsAg from a reference HBV and wherein an antibody directed to a reference HBV exhibits an altered immunological profile to an HBV carrying said variant HBsAg. In one embodiment, the altered immunological profile comprises a reduction in the ability to neutralize the variant HBV.

Another aspect of the present invention contemplates a method for detecting an agent which exhibits inhibitory activity to an HBV by generating a genetic construct comprising a replication competent-effective amount of the genome from the HBV contained in a plasmid vector and then transfecting said cells with said construct, contacting the cells, before, during and/or after transfection, with the agent to be tested, culturing the cells for a time and under conditions sufficient for the HBV to replicate, express genetic sequences and/or assemble and/or release virus or virus-like particles if resistant to said agents; and the subjecting the cells, cell lysates or culture supernatant fluid to viral- or viral-component-detection means to determine whether or not the virus has replicated, expressed genetic material and/or assembled and/or been released in the presence of the agent. In a preferred embodiment, the plasmid vector in a baculovirus vector and the method comprises generating a genetic construct comprising a replication competent-effective amount of the genome from the HBV contained in or fused to an amount of a baculovirus genome effective to infect cells and then infecting said cells with said construct, contacting the cells, before, during and/or after infection, with the agent to be tested, culturing the cells for a time and under conditions sufficient for the HBV to replicate, express genetic sequences and/or assemble and/or release virus or virus-like particles if resistant to said agent and then subjecting the cells, cell lysates or culture supernatant fluid to viral- or viral-component-detection means to determine whether or not the virus has replicated, expressed genetic material and/or assembled and/or been released in the presence of the agent.

In connection with these methods, the plasmid vector may include genes encoding part or all of other viral vectors such as baculovirus vectors or adenovirus vectors (see Ren and Nassal, *J. Virol.* 75(3):1104-1116, 2001).

In an alternative embodiment, the method comprises generating a continuous cell line comprising an infectious copy of the genome of the HBV in a replication competent effective amount such that said infectious HBV genome is stably integrated into said continuous cell line such as but not limited to the 2.2.15 or AD cell line, contacting the cells with the agent to be tested, culturing the cells for a time and under conditions sufficient for the HBV to replicate, express genetic sequences and/or assemble and/or release virus or virus-like particles if resistant to the agent and then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the present invention also contemplates a method for detecting an agent which exhibits inhibitory activity to an HBV polymerase in an in vitro polymerase assay. The HBV polymerase activity can be examined using established assays (Gaillard et al., *Antimicrob Agents Chemother.* 46(4): 1005-1013, 2002; Xiong et al., *Hepatology.* 28(6): 1669-73, 1998). The HBV polymerase may be a wild-type or reference HBV polymerase or mutant HBV polymerase.

The identification of viral variants enables the production of vaccines comprising particular recombinant viral components such as polymerases or envelope genes PreS1, PreS2, S encoding for L, M, S proteins as well as therapeutic vaccines comprising defective HBV variants. Rational drug design may also be employed to identify or generate therapeutic molecules capable of interacting with a polymerase or envelope genes PreS1, PreS2, S encoding for L, M, S proteins or other component of the HBV. Such drugs may also have diagnostic potential. In addition, defective HBV variants may also be used as therapeutic compositions to generate an immune response against the same, similar or homologous viruses. Alternatively, antibodies generated to the HBV variants or surface components thereof may be used in passive immunization of subjects against infection by HBV variants or similar or homologous viruses. Furthermore, agents such as nucleoside or nucleotide analogs, RNAi or siRNA molecules, antisense or sense oligonucleotides, chemical or proteinaceous molecules having an ability to down-regulate the activity of a component of HBV and inhibit replication, maintenance, infection, assembly or release are contemplated by the present invention.

A summary of the abbreviations used throughout the subject specification are provided in Table 3.

A summary of sequence identifiers used throughout the subject specification is provided in Table 1.

TABLE 1

Summary of sequence identifiers

| SEQUENCE ID NO: | DESCRIPTION |
|---|---|
| 1 | Formula I |
| 2 | Formula II |
| 3 | OS1 primer |
| 4 | TTA3 primer |
| 5 | JM primer |
| 6 | TTA4 primer |
| 7 | OS2 primer |
| 8 | sense primer |
| 9 | antisense primer |
| 10 | internal regions primer |
| 11 | internal regions primer |
| 12 | PC1 forward primer |
| 13 | PC2 reverse primer |
| 14 | HBV-specific molecular beacon primer |
| 15 | ILA 1 F, A-E (FIG. 4) |
| 16 | ILA 2 F, A-E (FIG. 4) |
| 17 | ILA 3 F, A-E (FIG. 4) |
| 18 | ILA 4 F, A-E (FIG. 4) |
| 19 | Pol Trans Pre 1 (FIG. 5) |
| 20 | Pol Trans 2 (FIG. 5) |
| 21 | Pol Trans 3 (FIG. 5) |
| 22 | Pol Trans 4 (FIG. 5) |
| 23 | HBsAg Trans of Pre 1 (FIG. 6) |
| 24 | HBsAg Trans of 2 (FIG. 6) |
| 25 | HBsAg Trans of 3 (FIG. 6) |
| 26 | HBsAg Trans of 4(FIG. 6) |
| 27 | S0 (FIG. 7) |
| 28 | S6 (FIG. 7) |
| 29 | S8 (FIG. 7) |
| 30 | S12 (FIG. 7) |
| 31 | S15 (FIG. 7) |
| 32 | Pol Trans S0 (FIG. 8) |
| 33 | Pol Trans S6 (FIG. 8) |
| 34 | Pol Trans S8 (FIG. 8) |
| 35 | Pol Trans S12 (FIG. 8) |
| 36 | Pol Trans S15 (FIG. 8) |
| 37 | HBsAg Trans of S0 (FIG. 9) |
| 38 | HBsAg Trans of S6 (FIG. 9) |
| 39 | HBsAg Trans of S8 (FIG. 9) |
| 40 | HBsAg Trans of S12 (FIG. 9) |
| 41 | HBsAg Trans of S15 (FIG. 9) |
| 42 | Nucleotide sequence Patient C (FIG. 10) |
| 43 | POL Trans of Patient C (FIG. 11) |
| 44 | HBsAg Trans of Patient C (FIG. 12) |
| 45 | Nucleotide sequence of Patient D (FIG. 13) |
| 46 | Pol Trans of Patient D (FIG. 14) |
| 47 | HBsAg Trans of Patient D (FIG. 15) |
| 48 | Nucleotide sequence of Patient E (FIG. 16) |
| 49 | Pol Trans of Patient E (FIG. 17) |
| 50 | HBsAg Trans of Patient E (FIG. 18) |
| 51 | Nucleotide sequence of Patient F (FIG. 20) |
| 52 | Deduced sequence of DNA polymerase of Patient F (FIG. 21) |
| 53 | HBsAg Trans of Patient F (FIG. 22) |

TABLE 1-continued Summary of sequence identifiers

| SEQUENCE ID NO: | DESCRIPTION |
|---|---|
| 54 | Nucleotide sequence of Patient G (FIG. 23) |
| 55 | Deduced sequence of DNA polymerase of Patient G (FIG. 24) |
| 56 | HBsAg Trans of Patient G (FIG. 25) |
| 57 | Nucleotide sequence of Patient H (FIG. 26) |
| 58 | Deduced sequence of DNA polymerase of Patient H (FIG. 27) |
| 59 | HBsAg Trans of Patient H (FIG. 28) |

TABLE 2

Single and three letter amino acid abbreviations

| Amino Acid | Three-letter Abbreviation | One-letter symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

A list of abbreviations used throughout the subject specification are provided in Table 3.

TABLE 3

Abbreviations

| ABBREVIATION | DESCRIPTION |
|---|---|
| 3TC | (LMV); (−)-β-2'-deoxy-3'-thiacytidine |
| ADV | adefovir dipivoxil |
| DAPD | diaminopurine dioxalone |
| DXG | dioxolane guanine |
| ETV | entecavir |
| FAM | famciclovir |
| FCV | famciclovir |
| FTC | emtricitabine |
| HBIG | hepatitis B immunoglobulin |
| HBsAg | hepatitis B surface antigen |
| HBV | hepatitis B virus |
| LMV | lamividuine |
| PMEA | 9-[phosphonyl-methoxyethyl]-adenine; adefovir |
| PMPA | 9-R-(2-phosphonomethoxypropyl)adenine |
| RNase | ribonuclease |
| rt ("rt" before "Xaa$_1$nXaa$_2$" means reverse transcriptase) | reverse transcriptase |
| s (as used in a mutation, e.g. sF134V) | envelope gene |
| TFV | tenofovir disoproxil fumarate |

TABLE 3-continued

Abbreviations

| ABBREVIATION | DESCRIPTION |
|---|---|
| YMDD | Tyr Met Asp Asp-a motif in the polymerase protein; where the Met residue is designated residue number 204 of the reverse transcriptase |

BRIEF DESCRIPTION OF THE FIGURES

FIG. 4 is a representation showing comparison of the HBV nucleotide sequence encoding the catalytic region of the polymerase gene in sequential samples from Patient A during ADV treatment.

FIG. 5 is a representation showing comparison of the deduced amino acid sequence of the catalytic region of the polymerase gene in sequential samples from Patient A during ADV therapy.

FIG. 6 is a representation showing comparison of the deduced amino acid sequence of the envelope gene in sequential samples from Patient A during ADV therapy.

FIG. 7 is a representation showing comparison of the HBV nucleotide sequence encoding the catalytic region of the polymerase gene in sequential samples from Patient B during ADV and LMV treatment.

FIG. 8 is a representation showing comparison of the deduced amino acid sequence of the catalytic region of the polymerase gene in sequential samples from Patient B during ADV and LMV therapy.

FIG. 9 is a representation showing comparison of the deduced amino acid sequence of the envelope gene in sequential samples from Patient B during ADV and LMV therapy.

FIG. 10 is a representation showing comparison of the HBV nucleotide sequence encoding the catalytic region of the polymerase gene in sequential samples from Patient C during ADV treatment (SEQ ID NO: 42).

FIG. 11 is a representation showing comparison of the deduced amino acid sequence of the catalytic region of the polymerase gene in sequential samples from Patient C during ADV therapy (SEQ ID NO: 43).

FIG. 12 is a representation showing comparison of the deduced amino acid sequence of the envelope gene in sequential samples from Patient C during ADV therapy (SEQ ID NO: 44).

FIG. 13 is a representation showing comparison of the HBV nucleotide sequence encoding the catalytic region of the polymerase gene in sequential samples from Patient D during ADV treatment (SEQ ID NO: 45).

FIG. 14 is a representation showing comparison of the deduced amino acid sequence of the catalytic region of the polymerase gene in sequential samples from Patient D during ADV therapy (SEQ ID NO: 46).

FIG. 15 is a representation showing comparison of the deduced amino acid sequence of the envelope gene in sequential samples from Patient D during ADV therapy (SEQ ID NO: 47).

FIG. 16 is a representation showing comparison of the HBV nucleotide sequence encoding the catalytic region of the polymerase gene in sequential samples from Patient E during ADV treatment (SEQ ID NO: 48).

FIG. 17 is a representation showing comparison of the deduced amino acid sequence of the catalytic region of the polymerase gene in sequential samples from Patient E during ADV therapy (SEQ ID NO: 49).

FIG. 18 is a representation showing comparison of the deduced amino acid sequence of the envelope gene in sequential samples from Patient E during ADV therapy (SEQ ID NO: 50).

FIG. 20 is a representation showing the nucleotide sequence of envelope/rt region of an HBV isolated from Patient F having ADV therapy (SEQ ID NO: 51).

FIG. 21 is a representation showing the deduced amino acid sequence of DNA polymerase encoded by the nucleotide sequence shown in FIG. 20 (SEQ ID NO: 52).

FIG. 22 is a representation showing the deduced amino acid sequence of HBsAg encoded by the nucleotide sequence shown in FIG. 20 (SEQ ID NO: 53).

FIG. 23 is a representation showing the nucleotide sequence of envelope/rt region of an HBV isolated from Patient G having ADV therapy (SEQ ID NO: 54).

FIG. 24 is a representation showing the deduced amino acid sequence of DNA polymerase encoded by the nucleotide sequence shown in FIG. 23 (SEQ ID NO: 55).

FIG. 25 is a representation showing the deduced amino acid sequence of HBsAg encoded by the nucleotide sequence shown in FIG. 23 (SEQ ID NO: 56).

FIG. 26 is a representation showing the nucleotide sequence of envelope/rt region of an HBV isolated from Patient H having ADV therapy (SEQ ID NO: 57).

FIG. 27 is a representation showing the deduced amino acid sequence of DNA polymerase encoded by the nucleotide sequence shown in FIG. 26 (SEQ ID NO: 58).

FIG. 28 is a representation showing the deduced amino acid sequence of HBsAg encoded by the nucleotide sequence shown in FIG. 26 (SEQ ID NO: 59).

DETAILED DESCRIPTION OF THE INVENTION

Figure 1:
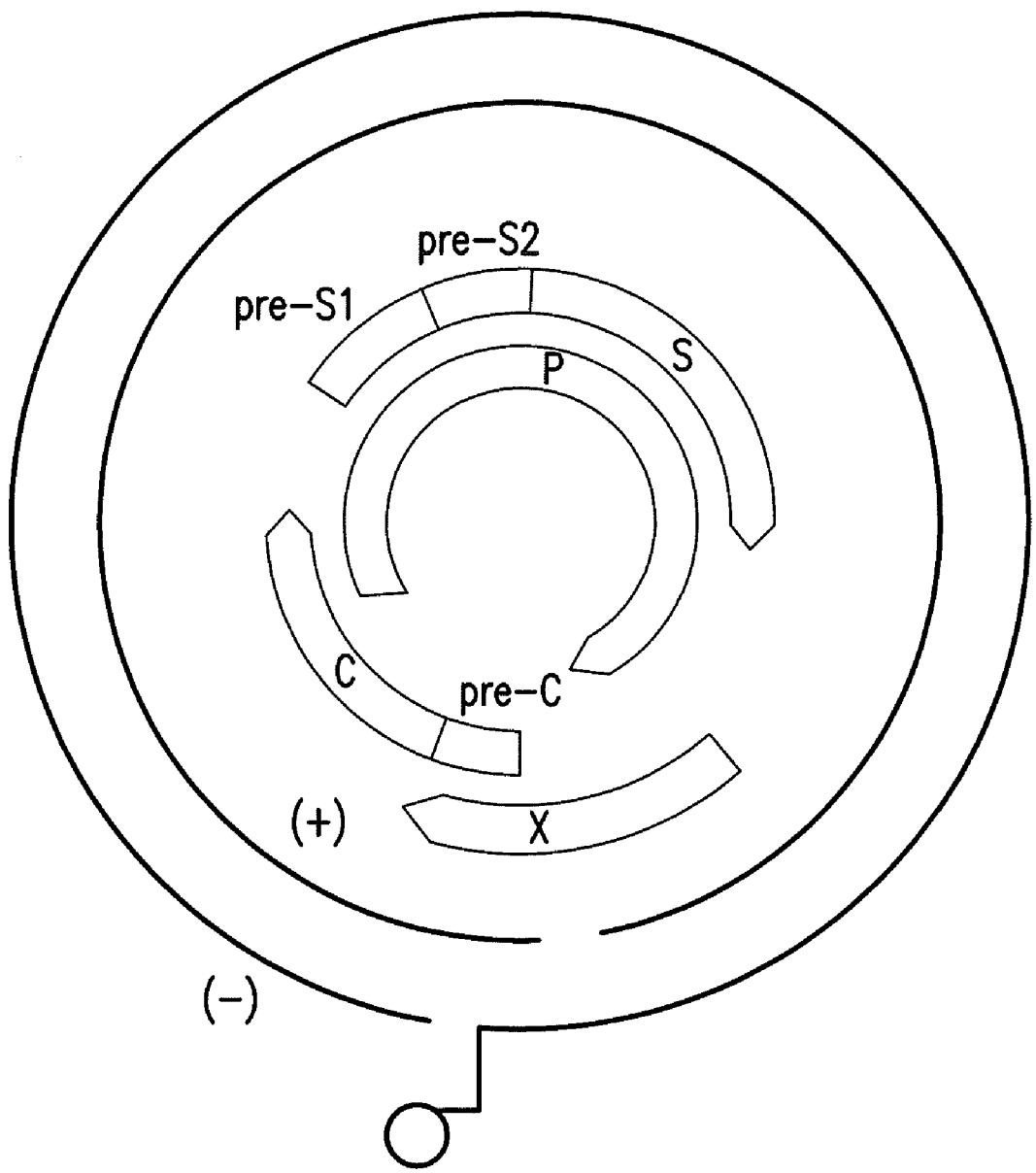
FIG. 1 is a diagrammatic representation showing the partially double stranded DNA HBV genome showing the overlapping open reading frames encoding surface (S), core (C), polymerase (P) and X gene.

The present invention is predicated in part on the identification and isolation of nucleoside or nucleotide analog-resistant variants of HBV following treatment of patients with either ADV or LMV or more particularly ADV and LMV, or optionally other nucleoside analogs or nucleotide analogs or other anti-HBV agents such as TFV or FTC. In particular, ADV or ADV and LMV treated patients gave rise to variants of HBV exhibiting decreased or reduced sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV. Reference herein to "decreased" or "reduced" in relation to sensitivity to ADV and/or LMV and/or FTC and/or TFV includes and encompasses a complete or substantial resistance to the nucleoside or nucleotide analog or other anti-HBV agents as well as partial resistance and includes a replication rate or replication efficiency which is more than a wild-type in the presence of a nucleoside or nucleotide analog or other anti-HBV agents. In one aspect, this is conveniently measured by an increase in viral load during treatment, or alternatively, there is no substantial decrease in HBV DNA viral load from pre-treatment HBV DNA levels during treatment (i.e., non-response to treatment).

Before describing the present invention in detail, it is to be understood that unless otherwise indicated, the subject invention is not limited to specific formulations of components, manufacturing methods, dosage regimens, or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to "a nucleoside or nucleotide analog" includes a single analog, as well as two or more analogs; reference to "an HBV variant" includes reference to two or more HBV variants; and so forth.

In describing and claiming the present invention, the following terminology is used in accordance with the definitions set forth below.

The terms "analog", "compound", "active agent", "pharmacologically active agent", "medicament", "active" and "drug" are used interchangeably herein to refer to a chemical compound that induces a desired effect such as inhibit viral replication, infection, maintenance, assembly and/or the function of an enzyme such as HBV DNA polymerase. The terms also encompass pharmaceutically acceptable and pharmacologically active ingredients of those active agents specifically mentioned herein including but not limited to salts, esters, amides, prodrugs, active metabolites, analogs and the like. When the terms "analog", "compound", "active agent", "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc.

The present invention contemplates, therefore, compounds useful in inhibiting HBV replication, infection, maintenance, assembly and/or the function of an enzyme such as HBV DNA polymerase. Reference to an "analog", "compound", "active agent", "pharmacologically active agent", "medicament", "active" and "drug" such as ADV, LMV, FTC and/or TFV includes combinations of two or more actives such as ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV. A "combination" also includes a two-part or more such as a multi-part anti-HBV therapeutic composition where the agents are provided separately and given or dispensed separately or admixed together prior to dispensation.

The terms "effective amount" and "therapeutically effective amount" of an agent as used herein mean a sufficient amount of the agent to provide the desired therapeutic or physiological effect of inhibiting HBV replication, infection, maintenance, assembly and/or the function of an enzyme such as HBV DNA polymerase. Furthermore, an "effective HBV-inhibiting amount" or "effective symptom-ameliorating amount" of an agent is a sufficient amount of the agent to directly or indirectly inhibit replication, infection, maintenance, assembly and/or the function of an enzyme such as HBV DNA polymerase. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, amide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage in relation to HBV infection. Thus, for example, "treating" a patient involves prevention of HBV infection as well as treatment of a clinically HBV symptomatic individual by inhibiting HBV replication, infection, maintenance, assembly and/or the function of an enzyme such as HBV DNA polymerase. Thus, for example, the present method of "treating" a patient with HBV infection or with a propensity for one to develop encompasses both prevention of HBV infection as well as treating HBV infection or symptoms thereof. In any event, the present invention contemplates the treatment or prophylaxis of HBV infection.

"Patient" as used herein refers to an animal, preferably a mammal and more preferably a primate including a lower primate and even more preferably, a human who can benefit from the formulations and methods of the present invention. A patient regardless of whether a human or non-human animal may be referred to as an individual, subject, animal, host or recipient. The compounds and methods of the present invention have applications in human medicine, veterinary medicine as well as in general, domestic or wild animal husbandry. For convenience, an "animal" includes an avian species such as a poultry bird (including ducks, chicken, turkeys and geese), an aviary bird or game bird. The condition in a non-human animal may not be a naturally occurring HBV infection but HBV-like infection may be induced.

As indicated above, the preferred animals are humans, non-human primates such as marmossets, baboons, orangatangs, lower primates such as tupia, livestock animals, laboratory test animals, companion animals or captive wild animals. A human is the most preferred target. However, non-human animal models may be used.

Examples of laboratory test animals include mice, rats, rabbits, guinea pigs and hamsters. Rabbits and rodent animals, such as rats and mice, provide a convenient test system or animal model as do primates and lower primates. Livestock animals include sheep, cows, pigs, goats, horses and donkeys. Non-mammalian animals such as avian species, zebrafish, amphibians (including cane toads) and *Drosophila* species such as *Drosophila melanogaster* are also contemplated. Instead of a live animal model, a test system may also comprise a tissue culture system.

Accordingly, one aspect of the present invention is directed to an isolated HBV variant wherein said variant comprises a nucleotide mutation in a gene encoding a DNA polymerase resulting in at least one amino acid addition, substitution and/or deletion to said DNA polymerase and wherein said variant exhibits decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, or ADV and LMV and FTC, ADV and FTC and LMV and TFV and/or optionally other nucleoside or nucleotide analogs or other anti-HBV agents or combination thereof.

HBV is a member of the Hepdnaviridae that includes also avian hepatitis viruses such as Duck hepatitis B virus (DHBV) and hepatitis viruses from mammals such as woodchuck hepatitis virus (WHV). These viruses have similarity to HBV and may be used in in vitro and in vivo or animal model systems to investigate the equivalent HBV mutants and antiviral sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, FTC and TFV, TFV and FTC and LMV, ADV and LMV and FTC, or ADV and FTC and LMV and TFV, An "anti-HBV agent" includes a nucleoside or nucleotide analog, protein, chemical compound, RNA or DNA or RNAi or siRNA oligonucleotide.

Preferably, the decreased sensitivity is in respect of ADV. Alternatively, the decreased sensitivity is in respect of LMV. Alternatively, the decreased sensitivity is in respect of TFV. Alternatively, the decreased sensitivity is in respect of FTC. Alternatively, the decreased sensitivity is in respect of ADV and LMV. Alternatively, the decreased sensitivity is in respect of ADV and TFV. Alternatively, the decreased sensitivity is in respect of LMV and TFV. Alternatively, the decreased sensitivity is in respect of ADV and FTC. Alternatively, the decreased sensitivity is in respect to FTC and TFV. Alternatively, the decreased sensitivity is in respect of FTC and LMV. Alternatively, the decreased sensitivity is in respect of ADV and LMV and TFV. Alternatively, the decreased sensitivity is in respect to ADV and TFV and FTC. Alternatively, the decreased sensitivity is in respect to LMV and TFV and FTC. Alternatively, the decrease sensitivity is in respect of ADV and LMV and FTC. Alternatively, the decreased sensitivity is in respect of ADV and FTC and TFV and LMV.

Reference herein to "anti-HBV agents" includes nucleoside and nucleotide analogs as well as immunological reagents (e.g. antibodies to HBV surface components) and chemical, proteinaceous and nucleic acid agents which inhibit or otherwise interfere with viral replication, maintenance, infection, assembly or release. Reference herein to "nucleic acid" includes reference to a sense or antisense molecule, RNA or DNA, oligonucleotides and RNAi and siRNA molecules and complexes containing same.

In addition to a mutation in the gene encoding DNA polymerase, due to the overlapping nature of the HBV genome (FIG. 1), a corresponding mutation may also occur in the gene encoding the S gene encoding the surface antigen (HBsAg) resulting in reduced interactivity of immunological reagents such as antibodies and immune cells to HBsAg. The reduction in the interactivity of immunological reagents to a viral surface component generally includes the absence of immunological memory to recognize or substantially recognize the viral surface component. The present invention extends, therefore, to an HBV variant exhibiting decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, and/or ADV and FTC and LMV and TFV or a reduced interactivity of an immunological reagent to HBsAg wherein the variant is selected for following ADV and/or LMV combination or sequential treatment. The term "sequential" in this respect means ADV followed by LMV and/or TFV, and/or FTC, LMV followed by ADV and/or TFV, and/or FTC, or multiple sequential administrations of each of ADV, LMV and/or TFV, and/or FTC.

A viral variant may, therefore, carry mutation only in the DNA polymerase gene or both in the DNA polymerase gene and the S gene. The term "mutation" is to be read in its broadest context and includes multiple mutations.

The present invention extends to a mutation and any domain of the HBV DNA polymerase and in particular regions F and G, and domains A through to E provided said mutation leads to decreased sensitivity to ADV and/or LMV and/or TFV or combinations thereof. Regions F and G of the HBV DNA polymerase is defined by the amino acid sequence set forth in Formula I below [SEQ ID NO:1]:

$$L,X_1,X_2,D,W,G,P,C,X_3,X_4,H,G,X_5,H,X_6,J,R,B_7,P,R,$$
$$T,P,X_8,R,V,X_9,G,G,V,F,L,V,D,K,N,P,H,N,T,X_{10},$$
$$E,S,X_{11},L,X_{12},V,D,F,S,Q,F,S,R,G,X_{13},X_{14},X_{15},$$
$$V,S,W,P,K,F,A,V,P,N,L,X_{16},S,L,T,N,L,L,S* \quad \text{FORMULA I}$$

wherein:

$X_1$ is L, or R, or I $X_2$ is E, or D $X_3$ is T, or D, or A, or N, or Y $X_4$ is E, or D $X_5$ is E, or K, or Q $X_6$ is H, or R, or N, $X_7$ is I, or T $X_8$ is A, or S $X_9$ is T or R $X_{10}$ is A, or T, or S $X_{11}$, is R, or T $X_{12}$ is V, or G $X_{13}$ is S, or I, or T, or N, or V $X_{14}$ is T, or S, or H, or Y $X_{15}$ is R, or H, or K, or Q $X_{16}$ is Q, or P;

and wherein S* is designated as amino acid 74.

In this specification, reference is particularly made to the conserved regions of the DNA polymerase as defined by domains A to E. Regions A to E are defined by the amino acid sequence set forth in Formula II below [SEQ ID NO:2] (and in Australian Patent No. 734831):

$$SX_1LSWLSLDVSAAFYHX_2PLHPAAMPHLLX_3GSSGLX_4$$
$$RYVARLSSX_5SX_6X_7XNX_8QX_9X_{10}XXXX_{11}LHX_{12}$$
$$X_{13}CSRX_{14}LYVSLX_{15}LLYX_{16}TX_{17}GX_{18}KLHLX_{19}$$
$$X_{20}HPIX_{21}LGFRKX_{22}PMGX_{23}GLSPFLLAQFTSAIX_{24}$$
$$X_{25}X_{26}X_{27}X_{28}RAFX_{29}HCX_{30}X_{31}FX_{32}YM*DDX_{33}$$
$$VLGAX_{34}X_{35}X_{36}X_{37}HX_{38}EX_{39}LX_{40}X_{41}X_{42}X_{43}X_{44}$$
$$X_{45}X_{46}LLX_{47}X_{48}GIHLNPX_{49}$$
$$KTKRWGYSLNFMGYX_{50}IG \quad \text{FORMULA II}$$

wherein:

X is any amino acid $X_1$ is N or D;

$X_2$ is I or P;

$X_3$ is I or V;

$X_4$ is S or D;

$X_5$ is T or N;

$X_6$ is R or N;

$X_7$ is N or I;

$X_8$ is N or Y or H;

$X_9$ is H or Y;

$X_{10}$ is G or R;

$X_{11}$ is D or N;

$X_{12}$ is D or N;

$X_{13}$ is S or Y;

$X_{14}$ is N or Q;

$X_{15}$ is L or M;

$X_{16}$ is K or Q;

$X_{17}$ is Y or F;

$X_{18}$ is R or W;

$X_{19}$ is Y or L;

$X_{20}$ is S or A;

$X_{21}$ is I or V;

$X_{22}$ is I or L;

$X_{23}$ is V or G;

$X_{24}$ is C or L;

$X_{25}$ is A or S;

$X_{26}$ is V or M;

$X_{27}$ is V or T;

$X_{28}$ is R or C;

$X_{29}$ is F or P;

$X_{30}$ is L or V;

$X_{31}$ is A or V;

$X_{32}$ is S or A;

$X_{33}$ is V or L or M;

$X_{34}$ is K or R;

$X_{35}$ is S or T;

$X_{36}$ is V or G;

$X_{37}$ is Q or E;

$X_{38}$ is L or S or R;

$X_{39}$ is S or F;

$X_{40}$ is F or Y;

$X_{41}$ is T or A;

$X_{42}$ is A or S;

$X_{43}$ is V or I;

$X_{44}$ is T or C;

$X_{45}$ is N or S;

$X_{46}$ is F or V;

$X_{47}$ is S or D;

$X_{48}$ is L or V;

$X_{49}$ is N or Q;

$X_{50}$ is V or I; and

M* is amino acid 204;

and wherein the first S is designated as amino acid 75.

Preferably, the mutation results in an altered amino acid sequence in any one or more of domains F and G, and domains A through to E or regions proximal thereto of the HBV DNA polymerase.

Another aspect of the present invention provides an HBV variant comprising a mutation in an overlapping open reading frame in its genome wherein said mutation is in a region defined by one or more of domains F and G, and domains A through to E of HBV DNA polymerase and wherein said variant exhibits decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents.

In a related embodiment, there is provided an HBV variant comprising a mutation in the nucleotide sequence encoding a DNA polymerase resulting in an amino acid addition, substitution and/or deletion in said DNA polymerase in one or more amino acids as set forth in Formula I [SEQ ID NO:1] and/or Formula II [SEQ ID NO:2]:

$$L,X_1,X_2,D,W,G,P,C,X_3,X_4,H,G,X_5,H,X_6,I,R,X_7,P,R,\\T,P,X_8,R,V,X_9,G,G,V,F,L,V,D,K,N,P,H,N,T,X_{10},\\E,S,X_{11},L,X_{12},V,D,F,S,Q,F,S,R,G,X_{13},X_{14},X_{15},\\V,S,W,P,K,F,A,V,P,N,L,X_{16},S,L,T,N,L,L,S^* \quad \text{FORMULA I}$$

wherein:

$X_1$ is L, or R, or I $X_2$ is E, or D $X_3$ is T, or D, or A, or N, or Y $X_4$ is E, or D $X_5$ is E, or K, or Q $X_6$ is H, or R, or N, $X_7$ is I, or T $X_8$ is A, or S $X_9$ is T or R $X_{10}$ is A, or T, or S $X_{11}$ is R, or T $X_{12}$ is V, or G $X_{13}$ is S, or I, or T, or N, or V $X_{14}$ is T, or S, or H, or Y $X_{15}$ is R, or H, or K, or Q $X_{16}$ is Q, or P; and $$SX_1LSWLSLDVSAAFYHX_2PLHPAAMPHLLX_3GSSGLX_4\\RYVARLSSX_5SX_6X_7XNX_8QX_9X_{10}XXXX_{11}LHX_{12}X_{13}\\CSRX_{14}LYVSLX_{15}LLYX_{16}TX_{17}GX_{18}KLHLX_{19}X_{20}\\HPIX_{21}LGFRKX_{22}PMGX_{23}GLSPFLLAQFTSAIX_{24}X_{25}\\X_{26}X_{27}X_{28}RAFX_{29}HCX_{30}X_{31}FX_{32}YM^*DDX_{33}\\VLGAX_{34}X_{35}X_{36}X_{37}HX_{38}EX_{39}LX_{40}X_{41}X_{42}X_{43}\\X_{44}X_{45}X_{46}LLX_{47}X_{48}GIHLNPX_{49}\\KTKRWGYSLNFMGYX_{50}IG \quad \text{FORMULA II}$$

wherein:

X is any amino acid $X_1$ is N or D;

$X_2$ is I or P;

$X_3$ is I or V;

$X_4$ is S or D;

$X_5$ is T or N;

$X_6$ is R or N;

$X_7$ is N or I;

$X_8$ is N or Y or H;

$X_9$ is H or Y;

$X_{10}$ is G or R;

$X_{11}$ is D or N;

$X_{12}$ is D or N;

$X_{13}$ is S or Y;

$X_{14}$ is N or Q;

$X_{15}$ is L or M;

$X_{16}$ is K or Q;

$X_{17}$ is Y or F;

$X_{18}$ is R or W;

$X_{19}$ is Y or L;

$X_{20}$ is S or A;

$X_{21}$ is I or V;

$X_{22}$ is I or L;

$X_{23}$ is V or G;

$X_{24}$ is C or L;

$X_{25}$ is A or S;

$X_{26}$ is V or M;

$X_{27}$ is V or T;

$X_{28}$ is R or C;

$X_{29}$ is F or P;

$X_{30}$ is L or V;

$X_{31}$ is A or V;

$X_{32}$ is S or A;

$X_{33}$ is V or L or M;

$X_{34}$ is K or R;

$X_{35}$ is S or T;

$X_{36}$ is V or G;

$X_{37}$ is Q or E;

$X_{38}$ is L or S or R;

$X_{39}$ is S or F;

$X_{40}$ is F or Y;

$X_{41}$ is T or A;

$X_{42}$ is A or S;

$X_{43}$ is V or I;

$X_{44}$ is T or C;

$X_{45}$ is N or S;

$X_{46}$ is F or V;

$X_{47}$ is S or D;

$X_{48}$ is L or V;

$X_{49}$ is N or Q;

$X_{50}$ is V or I; and

M* is amino acid 204;

and wherein S* in Formula I is designated as amino acid 74 and the first S in Formula II is designated as amino acid 75;

and wherein said variant exhibits decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof. Preferably, the decreased sensitivity is to ADV or to both ADV and LMV or to one or both of ADV and/or LMV and/or TFV and/or FTC.

Another preferred aspect of the present invention contemplates an HBV variant comprising a mutation in the nucleotide sequence encoding HBsAg resulting in an amino acid addition, substitution and/or deletion in said HBsAg in a region corresponding to the amino acid sequence set forth in Formulae I and II wherein said variant exhibits decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

More particularly, the present invention provides a variant HBV comprising a surface antigen having an amino acid sequence with a single or multiple amino acid substitution, addition and/or deletion or a truncation compared to a surface antigen from a reference or wild-type HBV and wherein an antibody generated to the reference or wild-type surface antigen exhibits reduced capacity for neutralizing said HBV variant, said variant selected by exposure of a subject to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

The term "combination therapy" means that both combinations of ADV, LMV, FTC and/or TFV are co-administered in the same composition or simultaneously in separate compositions. The term "sequential therapy" means that the two agents are administered within seconds, minutes, hours, days or weeks of each other and in either order. Sequential therapy also encompasses completing a therapeutic course with one or other of ADV, LMV, FTC or TFV and then completing a second or third or subsequent therapeutic courses with the other of ADV, LMV, FTC or TFV.

Accordingly, another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC therapy or therapy by one or more other nucleoside or nucleotide analogs or other anti-HBV agents.

Still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV therapy or therapy by one or more other nucleoside or nucleotide analogs or other anti-HBV agents.

Even yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and LMV therapy or therapy by one or more other nucleoside or nucleotide analogs or other anti-HBV agents.

Even still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and TFV therapy or therapy by one or more other nucleoside or nucleotide analogs or other anti-HBV agents.

A further aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV and TFV therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and FTC therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV and FTC therapy or therapy by one or more other nucleoside or nucleotide analogs or other anti-HBV agents.

Still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC and LMV therapy or therapy by one or more other nucleoside or nucleotide analogs or other anti-HBV agents.

Even yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and TFV therapy or therapy by one or more other nucleoside or nucleotide analogs or other anti-HBV agents.

Even still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and TFV therapy or therapy by one or more other nucleoside or nucleotide analogs or other anti-HBV agents.

A further aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and FTC therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC, LMV and TFV therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, FTC and TFV therapy or therapy by one or more other nucleoside or nucleotide analogs or other anti-HBV agents.

Still yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV, FTC and TFV therapy or therapy by one or more other nucleoside or nucleotide analogs or other anti-HBV agents.

Preferably, the variants are in isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. Furthermore, the present invention provides isolated components from the variant HBVs such as but not limited to an isolated HBsAg. Accordingly, the present invention provides an isolated HBsAg or a recombinant form thereof or derivative or chemical equivalent thereof, said HBsAg being from a variant HBV selected by exposure of a subject to one or more of ADV, LMV, FTC and/or TFV or optionally one or more nucleoside or nucleotide analogs or other anti-HBV agents.

More particularly, yet another aspect of the present invention is directed to an isolated variant HBsAg or a recombinant or derivative form thereof or a chemical equivalent thereof wherein said HBsAg or its recombinant or derivative form or its chemical equivalent exhibits an altered immunological profile compared to an HBsAg from a reference HBV, said HBsAg being from a variant HBV selected by exposure of a subject to one or more of ADV, LMV, FTC and/or TFV or optionally one or more nucleoside or nucleotide analogs or other anti-HBV agents.

Even more particularly, the present invention provides an isolated variant HBsAg or a recombinant or derivative form thereof or a chemical equivalent thereof wherein said HBsAg or its recombinant or derivative form or its chemical equivalent comprises an amino acid sequence with a single or multiple amino acid substitution, addition and/or deletion or a truncation compared to an HBsAg from a reference HBV and wherein a neutralizing antibody directed to a reference HBV exhibits no or reduced neutralising activity to an HBV carrying said variant HBsAg, said HBsAg being from a variant HBV selected by exposure of a subject to one or more of ADV, LMV, FTC and/or TFV or optionally one or more nucleoside or nucleotide analogs or other anti-HBV agents.

Preferred mutations in the HBV DNA polymerase include variants selected from patients with HBV recurrence following ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV treatment. Nucleoside or nucleotide analog or other anti-HBV agents treatment may occur in relation to a transplantation procedure (e.g. bone marrow transplantation (BMT) or OLT) or following treatment of patients diagnosed with hepatitis. Following selection of variants, viral loads are obtainable at levels similar to pre-treatment levels or are increasing while on therapy.

Preferred mutations include, in one embodiment, rtS21A, rtL122F, rtN124H, rtH126R, rtT28N, rtP130Q, rtD131N and rtY135C; in another embodiment, rt/N/S/T/V/V53D, rtY126Q, rtL180M, rtS202G, rtI204V and rtI235V/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment, rtH90D, and rtL/F108L; in even yet another embodiment, rtL157L/M, rtA181V and rtV207I; in still yet another embodiment, rtL80V, rtP109S, rtI163V, rtL229M and rtN/H/A/S/Q238K; in another embodiment, rtS78S/T, rtN118N/S, rtN139N/K, rtV142E, rtA181A/T, rtI204M, rtQ/P/S/Stop215Q, rtE218K/E and rtN238N/H; in a further embodiment, rtK32, rtN33, rtP34, rtH35 and rtT37; in yet another embodiment, rtP59, rtK60, rtF61, rtA62 and rtV63; in still another embodiment, rtD83, rtV84, rtS85, rtA86, rtY89, rtH90 and rtI/L91; in even yet another embodiment, rtP177, rtF178, rtL179, rtL180, rtA181, rtQ182, rtF183 and rtT184; in still yet another embodiment, rtM204 and rtY203; in another embodiment, rt235, rt236, rt237, rt238 and rt239; in a further embodiment, rt247, rt248, rt249, rt250 and rt251; in yet another embodiment, K32M/F/P/S/T/W/Y/V/A/R/N/D/C/Q/E/G/H/I/L/deletion;

N33D/C/Q/E/G/H/I/L/K/M/F/P/S/T/W/Y/V/A/R/deletion;

P34S/T/W/Y/V/A/1N/D/C/Q/E/G/H/I/L/K/M/F/deletion;

H35I/L/K/M/F/P/S/T/W/Y/V/A/R/N/D/C/Q/E/G/deletion;

T37W/Y/V/A/R/N/D/C/Q/E/G/H/I/L/K/M/F/P/S/deletion;

P59S/T/W/Y/V/A/R/N/D/C/Q/E/G/H/I/L/K/M/F/deletion;

K60M/F/P/S/T/W/Y/V/A/R/N/D/C/Q/E/G/H/I/L/deletion;

F61P/S/T/W/Y/V/A/R/N/D/C/Q/E/G/H/I/L/K/M/deletion;

A62R/N/D/C/Q/E/G/H/I/L/K/M/F/P/S/T/W/Y/V/deletion;

V63A/R/N/D/C/Q/E/G/H/I/L/K/M/F/P/S/T/W/Y/deletion;

D83C/Q/E/G/H/I/L/K/M/F/P/S/T/W/Y/V/A/R/N/deletion;

V84A/R/N/D/C/Q/E/G/H/F/L/K/M/F/P/S/T/W/Y/deletion;

S85T/W/Y/V/A/R/N/D/C/Q/E/G/H/I/L/K M/F/P/deletion;

A86R/N/D/C/Q/E/G/H/I/L/K/M/F/P/S/T/W/YV/deletion;

Y89V/A/R/N/D/C/Q/E/G/H/I/L/K/M/F/P/S/T/W/deletion;

H90I/L/K/M/F/P/S/T/W/Y/V/A/R/N/D/C/Q/E/G/deletion;

I/L91K/M/F/P/S/T/W/Y/V/A/R/N/D/C/Q/E/G/deletion;

P177S/T/W/Y/V/A/R/N/D/C/Q/E/G/H/I/L/K M/F/deletion;

F178P/S/T/W/Y/V/A/R/N/D/C/Q/E/G/H/I/L/K/M/deletion;

L179K/M/F/P/S/T/W/Y/V/A/R/N/D/C/Q/E/G/H/I/deletion;

L180K/M/F/P/S/T/W/Y/V/A/R/N/D/C/Q/E/G/H/J/deletion;

A181R/N/D/C/Q/E/G/H/I/L/K/M/F/P/S/T/W/YV/deletion;

Q183E/G/H/I/L/K/M/F/P/S/T/W/Y/V/A/R/N/D/C/deletion;

F183P/S/T/W/Y/V/A/R/N/D/C/Q/E/G/H/I/L/K/M/deletion;

T184W/Y/V/A/R/N/D/C/Q/E/G/H/I/L/K/M/F/P/S/deletion;

Y203V/A/R/N/D/C/Q/E/G/H/I/L/K/M/F/P/S/T/W/deletion;

M204F/P/S/T/W/Y/V/A/R/N/D/C/Q/E/G/H/I/L/K/deletion;

L235K/M/F/P/S/T/W/Y/V/A/R/N/D/C/Q/E/G/H/I/deletion;

N236D/C/Q/E/G/H/I/L/K/M/F/P/S/T/W/Y/V/A/R/deletion;

T237W/Y/V/A/R/N/D/C/Q/E/G/H/I/L/K/M/F/P/S/deletion;

P237S/T/W/Y/V/A/R/N/D/C/Q/E/G/H/I/L/K/M/F/deletion;

N238D/C/Q/E/G/H/L/L/K/M/F/P/S/T/W/Y/V/A/R/deletion;

H238I/L/K/M/F/P/S/T/W/Y/V/A/R/N/D/C/Q/E/G/deletion;

A238R/N/D/C/Q/E/G/H/I/L/K/M/F/P/S/T/W/Y/V/deletion;

S239T/W/Y/V/A/R/N/D/C/Q/E/G/H/I/L/K/M/F/P/deletion;

Q238E/G/H/I/L/K/M/F/P/S/T/W/Y/V/A/R/N/D/C/deletion;

K239M/F/P/S/T/W/Y/V/A/R/N/D/C/Q/E/G/H/I/L/deletion;

L247K/M/F/P/S/T/W/Y/V/A/R/N/D/C/Q/E/G/H/I/deletion;

N248D/C/Q/E/G/H/I/L/K/M/F/P/S/T/W/Y/V/A/R/deletion;

H248I/L/K/M/F/P/S/T/W/Y/V/A/R/N/D/C/Q/E/G/deletion;

F249P/S/T/W/Y/V/A/R/N/D/C/Q/E/G/H/I/L/K/M/deletion;

M250F/P/S/T/W/Y/V/A/R/N/D/C/Q/E/G/H/I/L/K/deletion;

G251H/I/L/K/M/F/P/S/T/W/Y/V/A/R/N/D/C/Q/E; and

V251A/R/N/D/C/Q/E/G/H/I/L/K/M/F/P/S/T/W/Y.

Reference above to "deletion" means that the first mentioned amino acid before the residue number has been deleted.

Such HBV variants are proposed to exhibit a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof. It should be noted that the nomenclature system for amino acid positions is based on the methionine residues in the YMDD motif being designated codon rtM204. This numbering system is different to that in Australian Patent No. 734831 where the methionine residue in the YMDD motif within the polymerase gene is designated codon 550. In this regard, rtL180M and rtM204V correspond to L526M and M550V, respectively, in Australian Patent No. 734831. Corresponding mutations may also occur in envelope genes such as in one or more of PreS1, PreS2 and S. The mutations in S gene encoding HBsAg at sT118R, sP120T, sS143S/T, sD144A or sI195M also result in mutation in the in the polymerase gene rtY126C, rtT128N, rtF151S/F or rtM204V respectively.

Another potential mode of action of ADV and other acyclic nucleoside phosphonates is that of immune stimulation (Calio et al, *Antiviral Res.* 23: 77-89, 1994). A number of mutations resulted in changes in the envelope gene detected in HBV variants which may be associated with immune escape. These changes include sT118R, sP120T, sS126T, sM133T, sM133L/M, sF134V, sS143S/T, sD144A, sG145A and/or sW172STOP.

HBV encoding the mutation at codon sG145R is a well characterized vaccine escape mutant, although the envelope protein from HBV encoding the mutation at sG145A does not have the same antigen/antibody binding characteristics as the sG145R. This mutation was detected in HBV isolated from patient C in conjunction with mutations at codons 143 and 144.

The identification of the variants of the present invention permits the generation of a range of assays to detect such variants. The detection of such variants may be important in identifying resistant variants to determine the appropriate form of chemotherapy and/or to monitor vaccination protocols, or develop new or modified vaccine preparations.

Still another aspect of the present invention contemplates a method for determining the potential for an HBV to exhibit reduced sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and A domains through to E or a region proximal thereto of said DNA polymerase and associated with resistance or decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents wherein the presence of such a mutation is an indication of the likelihood of resistance to said ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents.

Preferably, the assay detects one or more of the following mutations: in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment, rtH90D and rtL/F108L; in even yet another embodiment, sP120T, sM125T and sT127A; in still yet another embodiment, sT118R, sM133T, SF134V, sI195M, sS207R and sY225Y/C; in another embodiment, sS126T, sM133L/M, sS143S/T, sD144A, sG145A and sW172Stop; in a further embodiment, sN40S, sC69STOP, sM75I, sL88P, sT118A, sW182Stop, sW196L, sY206H and sY225F; in yet another embodiment, s181M and sP214Q; in still another embodiment, sF83S, sL173F and sW199L; in yet another embodiment, sI126T, sK160R, sS174N, sA184V, sW196L, sS210N, sF/C220L and sY221C; in still another embodiment, sC69Stop/C, sC76Y, sI110V/I, sY134N, sW172Stop/W, sW196Stop, sS207R; in even still another embodiment, rtK32, rtN33, rtP34, rtH35 and rtT37); in another embodiment, rtP59, rtK60, rtF61, rtA62 and rtV63); in a further embodiment, rtD83, rtV84, rtS85, rtA86, rtY89, rtH90 and rtI/L91); in yet another embodiment, rtP177, rtF178, rtL179, rtL180, rtA181, rtQ182, rtF183 and rtT184; in still another embodiment, rtM204 and rtY203; in even yet another embodiment, rt235, rt236, rt237, rt238 and rt239 and in even still another embodiment, rt247, rt248, rt249, rt250 and rt251 and in another embodiment, K32M/F/P/S/T/W/Y/V/A/R/N/D/C/Q/E/G/H/I/L/deletion;

N33D/C/Q/E/G/H/I/L/K/M/F/P/S/T/W/Y/V/A/R/deletion;

P34S/T/W/Y/V/A/R/N/D/C/Q/E/G/H/L/K/M//deletionF;

H35I/L/K/M/F/P/S/T/W/Y/V/A/R/N/D/C/Q/E/G/deletion;

T37W/Y/V/A/R/N/D/C/Q/E/G/H/I/L/K/M/F/P/S/deletion;

P59S/T/W/Y/V/A/R/N/D/C/Q/E/G/H/I/L/K/M/F/deletion;

K60M/F/P/S/T/W/Y/V/A/R/N/D/C/Q/E/G/H/I/L/deletion;

F61P/S/T/W/Y/V/A/R/N/D/C/Q/E/G/H/I/L/L/K/M/deletion;

A62R/N/D/C/Q/E/G/H/I/K/M/F/P/S/T/W/Y/V/deletion;

V63A/R/N/D/C/Q/E/G/H/I/L/K/M/F/P/S/T/W/Y/deletion;

D83C/Q/E/G/H/I/L/K/M/F/P/S/T/W/Y/V/A/R/N/deletion;

V84A/R/N/D/C/Q/E/G/H/I/L/K/M/F/P/S/T/W/Y/deletion;

S85T/W/Y/V/A/R/N/D/C/Q/E/G/H/I/L/K/M/F/P/deletion;

A86R/N/D/C/Q/E/G/H/I/L/K/M/F/P/S/T/W/YV/deletion;

Y89V/A/R/N/D/C/Q/E/G/H/I/L/K/M/F/P/S/T/W/deletion;

H90I/L/K/M/F/P/S/T/W/Y/V/A/R/N/D/C/Q/E/G/deletion;

I/L91K/M/F/P/S/T/W/Y/V/A/R/N/D/C/Q/E/G/H/deletion;

P177S/T/W/Y/V/A/R/N/D/C/Q/E/G/H/I/L/K/M/F/deletion;

F178P/S/T/W/Y/V/A/R/N/D/C/Q/E/G/H/I/L/K/M/deletion;

L179K/M/F/P/S/T/W/Y/V/A/R/N/D/C/Q/E/G/H/I/deletion;

L180K/M/F/P/S/T/W/Y/V/A/R/N/D/C/Q/E/G/H/I/deletion;

A181R/N/D/C/Q/E/G/H/I/L/K/M/F/P/S/T/W/Y/v/deletion;

Q183E/G/H/I/L/K/M/F/P/S/T/W/Y/V/A/R/N/D/C/deletion;

F183P/S/T/W/Y/V/A/R/N/D/C/Q/E/G/H/I/L/K/M/deletion;

T184W/Y/V/A/R/N/D/C/Q/E/G/H/I/L/K/M/F/P/S/deletion;

Y203V/A/R/N/D/C/Q/E/G/H/I/L/K/M/F/P/S/T/W/deletion;

M204F/P/S/T/W/Y/V/A/R/N/D/C/Q/E/G/H/I/L/K/deletion;

L235K/M/F/P/S/T/W/Y/VIA/R/N/D/C/Q/E/G/H/I/deletion;

N236D/C/Q/E/G/H/I/L/K/M/F/P/S/T/W/Y/V/A/R/deletion;

T237W/Y/V/A/R/N/D/C/Q/E/G/H/I/L/K/M/F/P/S/deletion;

P237S/T/W/Y/V/A/R/N/D/C/Q/E/G/H/I/L/K/M/F/deletion;

N238D/C/Q/E/G/H/I/L/K/M/F/P/S/T/W/Y/V/A/R/deletion;

H238I/L/K/M/F/P/S/T/W/Y/V/A/R/N/D/C/Q/E/G/deletion;

A238R/N/D/C/Q/E/G/H/I/L/K/M/F/P/S/T/W/YV/deletion;

S239T/W/Y/V/A/R/N/D/C/Q/E/G/H/I/L/K/M/F/P/deletion;

Q238E/G/H/I/L/K/M/F/P/S/T/W/Y/V/A/R/N/D/C/deletion;

K239M/F/P/S/T/W/Y/V/A/R/N/D/C/Q/E/G/H/I/L/deletion;

L247K/M/F/P/S/T/W/Y/V/A/R/N/D/C/Q/E/G/H/I/deletion;

N248D/C/Q/E/G/H/I/L/K/M/F/P/S/T/W/Y/V/A/R/deletion;

H248I/L/K/M/F/P/S/T/W/Y/V/A/R/N/D/C/Q/E/G/deletion;

F249P/S/T/W/Y/V/A/R/N/D/C/Q/E/G/H/I/L/K/M/deletion;

M250F/P/S/T/W/Y/V/A/R/N/D/C/Q/E/G/H/I/L/K/deletion;

G251H/I/L/K/M/F/P/S/T/W/Y/V/A/R/N/D/C/Q/E/deletion; and

V251A/R/N/D/C/Q/E/G/I/L/K/M/F/P/S/T/W/Y/deletion or combinations thereof or an equivalent one or more other mutation is indicative of a variant wherein said variant exhibits a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

Accordingly, another aspect of the present invention produces a method for determining whether an HBV strain exhibits reduced sensitivity to a nucleoside or nucleotide analog or other anti-HBV agents, said method comprising isolating DNA or corresponding mRNA from said HBV and screening for a mutation in the nucleotide sequence encoding the DNA polymerase and/or a corresponding region of the S gene, wherein the presence of a mutation selected from, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191, rtM204I and rtV214A; in still another embodiment, rtH90D and rtL/F108L; in even yet another embodiment, sP120T, sM125T and sT127A; in still yet another embodiment, sT118R, sM133T, SF134V, sI195M, sS207R and sY225Y/C; in another embodiment, sS126T, sM133L/M, sS143S/T, sD144A, sG145A and sW172Stop; in a further embodiment, sN40S, sC69STOP, sM75I, sL88P, sT118A, sW182Stop, sW196L, sY206H and sY225F; in yet another embodiment, s181M and sP214Q; in still another embodiment, sF83S, sL173F and sW199L; in yet another embodiment, sI126T, sK160R, sS174N, sA184V, sW196L, sS210N, sF/C220L and sY221C; in still another embodiment, sC69Stop/C, sC76Y, sI110V/I, sY134N, sW172Stop/W, sW196Stop, sS207R; in even still another embodiment, rtK32, rtN33, rtP34, rtH35 and rtT37); in another embodiment, rtP59, rtK60, rtF61, rtA62 and rtV63); in a further embodiment, rtD83, rtV84, rtS85, rtA86, rtY89, rtH90 and rtI/L91); in yet another embodiment, rtP177, rtF178, rtL179, rtL180, rtA181, rtQ182, rtF183 and rtT184; in still another embodiment, rtM204 and rtY203; in even yet another embodiment, rt235, rt236, rt237, rt238 and rt239 and in even still another embodiment, rt247, rt248, rt249, rt250 and rt251; and in another embodiment, K32M/F/P/S/T/W/Y/V/A/R N/D/C/Q/E/G/H/I/L/deletion;

N33D/C/Q/E/G/H/I/L/K/M/F/P/S/T/W/Y/V/A/R/deletion;

P34S/T/W/Y/V/A/R/N/D/C/Q/E/G/H/I/L/K/M/F/deletion;

H351/L/K/M/F/P/S/T/W/Y/V/A/R/N/D/C/Q/E/G/deletion;

T37W/Y/V/A/R/N/D/C/Q/E/G/H/I/L/K/M/F/P/S/deletion;

P59S/T/W/Y/V/A/R/N/D/C/Q/E/G/H/I/L/K/M/F/deletion;

K60M/F/P/S/T/W/Y/V/A/R/N/D/C/Q/E/G/H/I/L/deletion;

F61P/S/T/W/Y/V/A/R/N/D/C/Q/E/G/H/I/L/K/M/deletion;

A62R/N/D/C/Q/E/G/H/I/L/K/M/F/P/S/T/W/Y/V/deletion;

V63A/R/N/D/C/Q/E/G/H/I/L/K/M/F/P/S/T/W/Y/deletion;

D83C/Q/E/G/H/I/L/K/M/F/P/S/T/W/Y/V/A/R/N/deletion;

V84A/R/N/D/C/Q/E/G/H/I/L/K/M/F/P/S/T/W/Y/deletion;

S85T/W/Y/V/A/R/N/D/C/Q/E/G/H/I/L/K/M/F/P/deletion;

A86R/N/D/C/Q/E/G/H/I/L/K/M/F/P/S/T/W/Y/V/deletion;

Y89V/A/R/N/D/C/Q/E/G/H/I/L/K/M/F/P/S/T/W/deletion;

H90I/L/K/M/F/P/S/T/W/Y/V/A/R/N/D/C/Q/E/G/deletion;

I/L91K/M/F/P/S/T/W/Y/V/A/R/N/D/C/Q/E/G/H/deletion;

P177S/T/W/Y/V/A/R/N/D/C/Q/E/G/H/I/L/K/M/F/deletion;

F178P/S/T/W/Y/V/A/R/N/D/C/Q/E/G/H/I/L/K/M/deletion;

L179K/M/F/P/S/T/W/Y/V/A/R/N/D/C/Q/E/G/H/I/deletion;

L180K/M/F/P/S/T/W/Y/V/A/R/N/D/C/Q/E/G/H/I/deletion;

A181R/N/D/C/Q/E/G/H/I/L/K/M/F/P/S/T/W/Y/V/deletion;

Q183E/G/H/I/L/K/M/F/P/S/T/W/Y/V/A/R/N/D/C/deletion;

F183P/S/T/W/Y/V/A/R/N/D/C/Q/E/G/H/I/L/K/M/deletion;

T184W/Y/V/A/R/N/D/C/Q/E/G/H/I/L/K/M/F/P/S/deletion;

Y203V/A/R/N/D/C/Q/E/G/H/I/L/K/M/F/P/S/T/W/deletion;

M204F/P/S/T/W/Y/V/A/R/N/D/C/Q/E/G/H/I/L/K/deletion;

L235K/M/F/P/S/T/W/Y/V/A/R/N/D/C/Q/E/G/H/I/deletion;

N236D/C/Q/E/G/H/I/L/K/M/F/P/S/T/W/Y/V/A/R/deletion;

T237W/Y/V/A/R/N/D/C/Q/E/G/H/I/L/K/M/F/P/S/deletion;

P237S/T/W/Y/V/A/R/N/D/C/Q/E/G/H/I/L/K/M/F/deletion;

N238D/C/Q/E/G/H/I/L/K/M/F/P/S/T/W/Y/V/A/R/deletion;

H238I/L/K/M/F/P/S/T/W/Y/V/A/R/N/D/C/Q/E/G/deletion;

A238R/N/D/C/Q/E/G/H/L/K/M/F/P/S/T/W/Y/V/deletion;

S239T/W/Y/V/A/R/N/D/C/Q/E/G/H/I/L/K/M/F/P/deletion;

Q238E/G/H/I/L/K/M/F/P/S/T/W/Y/V/A/R/N/D/C/deletion;

K239M/F/P/S/T/W/Y/V/A/R/N/D/C/Q/E/G/H/I/L/deletion;

L247K/M/F/P/S/T/W/Y/V/A/R/N/D/C/Q/E/G/H/I/deletion;

N248D/C/Q/E/G/H/I/L/K/M/F/P/S/T/W/Y/V/A/R/deletion;

H248I/L/K/M/F/P/S/T/W/Y/V/A/R/N/D/C/Q/E/G/deletion;

F249P/S/T/W/Y/V/A/R/N/D/C/Q/E/G/H/I/L/K/M/deletion;

M250F/P/S/T/W/Y/V/A/R/N/D/C/Q/E/G/H/I/L/K/deletion;

G251H/I/L/K/M/F/P/S/T/W/Y/V/A/R/N/D/C/Q/E/deletion; and

V251A/R/N/D/C/Q/E/G/H/I/L/K/M/F/P/S/T/W/Y/deletion or combinations thereof or an equivalent one or more other mutation is indicative of a variant which exhibits a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

A further aspect of the present invention produces a method for determining whether an HBV strain exhibits reduced sensitivity to a nucleoside or nucleotide analog or other anti-HBV agents, said method comprising isolating DNA or corresponding mRNA from said HBV and screening for a mutation in the nucleotide sequence encoding the DNA polymerase and/or a corresponding region of the S gene, wherein the presence of a mutation selected from, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141F/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment, rtH90D and rtL/F108L; in even yet another embodiment, sP120T, sM125T and sT127A; in still yet another embodiment, sT118R, sM133T, SF134V, sI195M, sS207R and sY225Y/C; in another embodiment, sS126T, sM133L/M, sS143S/T, sD144A, sG145A and sW172Stop; in a further embodiment, sN40S, sC69STOP, sM75I, sL88P, sT118A, sW182Stop, sW196L, sY206H and sY225F; in yet another embodiment, s181M and sP214Q; in still another embodiment, sF83S, sL173F and sW199L; in yet another embodiment, sI126T, sK160R, sS174N, sA184V, sW196L, sS210N, sF/C220L and sY221C; in still another embodiment, sC69Stop/C, sC76Y, sI110V/I, sY134N, sW172Stop/W, sW196Stop, sS207R; in even still another embodiment, rtK32, rtN33, rtP34, rtH35 and rtT37); in another embodiment, rtP59, rtK60, rtF61, rtA62 and rtV63); in a further embodiment, rtD83, rtV84, rtS85, rtA86, rtY89, rtH90 and rtI/L91); in yet another embodiment, rtP177, rtF178, rtL179, rtL180, rtA181, rtQ182, rtF183 and rtT184); in still another embodiment, rtM204 and rtY203; in even yet another embodiment, rt235, rt236, rt237, rt238 and rt239 and in even still another embodiment, rt247, rt248, rt249, rt250 and rt251; and in another embodiment, K32M/F/P/S/T/W/Y/V/A/R/N/D/C/Q/E/G/H/I/L/deletion;

N33D/C/Q/E/G/H/I/L/K/M/F/P/S/T/W/Y/V/A/R/deletion;

P34S/T/W/Y/V/A/R/N/D/C/Q/E/G/H/I/L/K/M/F/deletion;

H35I/L/K/M/F/P/S/T/W/Y/V/A/R/N/D/C/Q/E/G/deletion;

T37W/Y/V/A/R/N/D/C/Q/E/G/H/I/L/K/M/F/P/S/deletion;

P59S/T/W/Y/V/A/R/N/D/C/Q/E/G/H/I/L/K/M/F/deletion;

K60M/F/P/S/T/W/Y/V/A/R/N/D/C/Q/E/G/H/I/L/deletion;

F61P/S/T/W/Y/V/A/R/N/D/C/Q/E/G/H/I/L/K/M/deletion;

A62R/N/D/C/Q/E/G/H/I/L/K/M/F/P/S/T/W/Y/V/deletion;

V63A/R/N/D/C/Q/E/G/H/I/L/K/M/F/P/S/T/W/Y/deletion;

D83-C/Q/E/G/H/I/L/K/M/F/P/S/T/W/Y/V/A/R/N/deletion;

V84A/R/N/D/C/Q/E/G/H/I/L/K/M/F/P/S/T/W/Y/deletion;

S85T/W/Y/V/A/R/N/D/C/Q/E/G/H/I/L/K/M/F/P/deletion;

A86R/N/D/C/Q/E/G/H/I/L/K/M/F/P/S/T/W/Y/V/deletion;

Y89V/A/R/N/D/C/Q/E/G/H/I/L/K/M/F/P/S/T/W/deletion;

H90I/L/K/M/F/P/S/T/W/Y/V/A/R/N/D/C/Q/E/G/deletion;

I/L91K/M/F/P/S/T/W/Y/V/A/R/N/D/C/Q/E/G/H/deletion;

P177S/T/W/Y/V/A/R/N/D/C/Q/E/G/H/I/L/K/M/F/deletion;

F178P/S/T/W/Y/V/A/R/N/D/C/Q/E/G/H/I/L/K/M/deletion;

L179K/M/F/P/S/T/W/Y/V/A/R/N/D/C/Q/E/G/H/I/deletion;

L180K/M/F/P/S/T/W/Y/V/A/R/N/D/C/Q/E/G/H/I/deletion;

A181R/N/D/C/Q/E/G/H/I/L/K/M/F/P/S/T/W/Y/V/deletion;

Q183E/G/H/I/L/K/M/F/P/S/T/W/Y/V/A/R/N/D/C/deletion;

F183P/S/T/W/Y/V/A/R/N/D/C/Q/E/G/H/I/L/K/M/deletion;

T184W/Y/V/A/R/N/D/C/Q/E/G/H/I/L/K/M/F/P/S/deletion;

Y203V/A/R/N/D/C/Q/E/G/H/I/L/K/M/F/P/S/T/W/deletion;

M204F/P/S/T/W/Y/V/A/R/N/D/C/Q/E/G/H/I/L/K/deletion;

L235K/M/F/P/S/T/W/Y/V/A/R/N/D/C/Q/E/G/H/I/deletion;

N236D/C/Q/E/G/H/I/L/K/M/F/P/S/T/W/Y/V/A/R/deletion;

T237W/Y/V/A/R/N/D/C/Q/E/G/H/I/L/K/M/F/P/S/deletion;

P237S/T/W/Y/V/A/R/N/D/C/Q/E/G/H/I/L/K/M/F/deletion;

N238D/C/Q/E/G/H/I/L/K/M/F/P/S/T/W/Y/V/A/R/deletion;

H238I/L/K/M/F/P/S/T/W/Y/V/A/R/N/D/C/Q/E/G/deletion;

A238R/N/D/C/Q/E/G/H/I/L/K/M/F/P/S/T/W/Y/V/deletion;

S239T/W/Y/V/A/R/N/D/C/Q/E/G/H/I/L/K/M/F/P/deletion;

Q238E/G/H/I/L/K/M/F/P/S/T/W/Y/V/A/R/N/D/C/deletion;

K239M/F/P/S/T/W/Y/V/A/R/N/D/C/Q/E/G/H/I/L/deletion;

L247K/M/F/P/S/T/W/Y/V/A/R/N/D/C/Q/E/G/H/I/deletion;

N248D/C/Q/E/G/H/I/L/K/M/F/P/S/T/W/Y/V/A/R/deletion;

H248I/L/K/M/F/P/S/T/W/Y/V/A/R/N/D/C/Q/E/G/deletion;

F249P/S/T/W/Y/V/A/R/N/D/C/Q/E/G/H/I/L/K/M/deletion;

M250F/P/S/T/W/Y/V/A/R/N/D/C/Q/E/G/H/I/L/K/deletion;

G251H/I/L/K/M/F/P/S/T/W/Y/V/A/R/N/D/C/Q/E/deletion; and

V251A/R/N/D/C/Q/E/G/H/I/L/K/M/F/P/S/T/W/Y/deletion or combinations thereof or an equivalent one or more other mutation is indicative of a variant which exhibits a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions. The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others. Other forms of detection include Northern blots, Southern blots, PCR sequencing, antibody procedures such as ELISA, Western blot and immunohistochemistry. A particularly useful assay includes the reagents and components required for immobilized oligonucleotide- or oligopeptide-mediated detection systems.

One particularly useful nucleic acid detection system is the reverse hybridization technique. In this technique, DNA from an HBV sample is amplified using a biotin or other ligand-labeled primer to generate a labeled amplificon. Oligonucleotides immobilized to a solid support such as a nitrocellulose film are then used to capture amplified DNA by hybridization. Specific nucleic acid fragments are identified via biotin or the ligand. Generally, the labeled primer is specific for a particular nucleotide variation to be detected. Amplification occurs only if the variation to be detected is present. There are many forms of the reverse hybridization assay and all are encompassed by the present invention.

Detecting HBV replication in cell culture is particularly useful.

This and other aspects of the present invention is particularly amenable to microarray analysis such as to identify oligonucleotides including sense and antisense molecules, RNAi or siRNA molecules or DNA or RNA-binding molecules which down-regulate genomic sequences or transcripts of HBV. Microarray analysis may also be used to identify particular mutations in the HBV genome such as within the HBV DNA polymerase-coding region or the HBsAg-coding region.

Another aspect of the present invention contemplates a method for detecting an agent which exhibits inhibitory activity to an HBV by:

- generating a genetic construct comprising a replication competent-effective amount of the genome from the HBV contained in a plasmid vector and then transfecting said cells with said construct;
- contacting the cells, before, during and/or after transfection, with the agent to be tested;
- culturing the cells for a time and under conditions sufficient for the HBV to replicate, express genetic sequences and/or assemble and/or release virus or virus-like particles if resistant to said agents; and
- then subjecting the cells, cell lysates or culture supernatant fluid to viral- or viral-component-detection means to determine whether or not the virus has replicated, expressed genetic material and/or assembled and/or been released in the presence of the agent.

In a preferred embodiment, the plasmid vector may include genes encoding part or all of other viral vectors such as baculovirus or adenovirus (Ren and Nassal, 2001, supra) and the method comprises:

- generating a genetic construct comprising a replication competent-effective amount of the genome from the HBV contained in or fused to an amount of a baculovirus genome or adenovirus genome effective to infect cells and then infecting said cells with said construct;
- contacting the cells, before, during and/or after infection, with the agent to be tested;
- culturing the cells for a time and under conditions sufficient for the HBV to replicate, express genetic sequences and/or assemble and/or release virus or virus-like particles if resistant to said agent; and
- then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the method comprises:

- generating a continuous cell line comprising an infectious copy of the genome of the HBV in a replication competent effective amount such that said infectious HBV genome is stably integrated into said continuous cell line such as but not limited to 2.2.15 or AD;
- contacting the cells with the agent to be tested;
- culturing the cells for a time and under conditions sufficient for the HBV to replicate, express genetic sequences and/or assemble and/or release virus or virus-like particles if resistant to the agent; and
- then subjecting the cells, cell lysates or culture supernatant fluid to viral- or viral-component-detection means to determine whether or not the virus has replicated, expressed genetic material and/or assembled and/or been released in the presence of the agent.

The above-mentioned methods are particularly useful in identifying or developing agents against HBV variants such as those carrying mutations, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment rtH90D and rtL/F108L; in even yet another embodiment, rtL157L/M, rtA181V and rtV207I; in even still another embodiment, rtL80V, rtP109S, rtI163V, rtL229M and rtN/H/A/S/Q238K; in another embodiment, rtS78S/T, rtN118N/S, rtN139N/K, rtV142E, rtA181A/T, rtI204M, rtQ/P/S/Stop215Q, rtE218K/E and rtN238N/H; in a further embodiment, sP120T, sM125T and sT127A; in yet another embodiment, sT118R, sM133T, SF134V, sI195M, sS207R and sY225Y/C; in still another embodiment, sS126T, sM133L/M, sS143S/T, sD144A, sG145A and sW172Stop; in even yet another embodiment, sN40S, sC69Stop, sM75I, sL88P, sT118A, sW182STOP, sW196L, sY206H and sY225F; in even still another embodiment, s181M and sP214Q; in another embodiment, sF83S, sL173F and sW199L; in a further embodiment, sI126T, sK160R, sS174N, sA184V, sW196L, sS210N, sF/C220L and sY221C; in yet another embodiment, sC69Stop/C, sC76Y sI110V/I, sY134N, sW172Stop/W, sW196Stop and sS207R; in still another embodiment, rtK32, rtN33, rtP34, rtH35 and rtT37; in even yet another embodiment, rtP59, rtK60, rtF61, rtA62 and rtV63; in even still another embodiment, rtD83, rtV84, rtS85, rtA86, rtY89, rtH90 and rtI/L91; in another embodiment, rtP177, rtF178, rtL179, rtL180, rtA181, rtQ182, rtF183 and rtT184; in a further embodiment, rtM204 and rtY203; in yet another embodiment, rt235, rt236, rt237, rt238 and rt239 in still another embodiment, rt247, rt248, rt249, rt250 and rt251; and in even yet another embodiment, K32M/F/P/S/T/W/Y/V/A/R/N/D/C/Q/E/G/H/I/L/deletion;

N33D/C/Q/E/G/H/I/L/K/M/F/P/S/T/W/Y/V/A/R/deletion;

P34S/T/W/Y/V/A/R/N/D/C/Q/E/G/H/I/L/K/M/F/deletion;

H35I/L/K/M/F/P/S/T/W/Y/V/A/R/N/D/C/Q/E/G/deletion;

T37W/Y/V/A/R/N/D/C/Q/E/G/H/I/L/K/M/F/P/S/deletion;

P59S/T/W/Y/V/A/R/N/D/C/Q/E/G/H/I/L/K/M/F/deletion;

K60M/F/P/S/T/W/Y/V/A/R/N/D/C/Q/E/G/H/I/L/deletion;

F61P/S/T/W/Y/V/A/R/N/D/C/Q/E/G/H/I/L/K/M/deletion;
A62R/N/D/C/Q/E/G/H/I/L/K/M/F/P/S/T/W/Y/V/deletion;
V63A/R/N/D/C/Q/E/G/H/I/L/K/M/F/P/S/T/W/Y/deletion;
D83C/Q/E/G/H/I/L/K/M/F/P/S/T/W/Y/V/A/R/N/deletion;
V84A/R/N/D/C/Q/E/G/H/I/L/K/M/F/P/S/T/W/Y/deletion;
S85T/W/Y/V/A/R/N/D/C/Q/E/G/H/I/L/K/M/F/P/deletion;
A86R/N/D/C/Q/E/G/H/I/L/K/M/F/P/S/T/W/Y/V/deletion;
Y89V/A/R/N/D/C/Q/E/G/H/I/L/K/M/F/P/S/T/W/deletion;
H90I/L/K/M/F/P/S/T/W/Y/V/A/R/N/D/C/Q/E/G/deletion;
I/L91K/M/F/P/S/T/W/Y/V/A/R/N/D/C/Q/E/G/H/deletion;
P177S/T/W/Y/V/A/R/N/D/C/Q/E/G/H/I/L/K/M/F/deletion;
F178P/S/T/W/Y/V/A/R/N/D/C/Q/E/G/H/I/L/K/M/deletion;
L179K/M/F/P/S/T/W/Y/V/A/R/N/D/C/Q/E/G/H/I/deletion;
L180K/M/F/P/S/T/W/Y/V/A/R/N/D/C/Q/E/G/H/I/deletion;
A181R/N/D/C/Q/E/G/H/I/L/K/M/F/P/S/T/W/Y/V/deletion;
Q183E/G/H/I/L/K/M/F/P/S/T/W/Y/V/A/R/N/D/C/deletion;
F183P/S/T/W/Y/V/A/R/N/D/C/Q/E/G/H/I/L/K/M/deletion;
T184W/Y/V/A/R/N/D/C/Q/E/G/H/I/L/K/M/F/P/S/deletion;
Y203V/A/R/N/D/C/Q/E/G/H/I/L/K/M/F/P/S/T/W/deletion;
M204F/P/S/T/W/Y/V/A/R/N/D/C/Q/E/G/H/I/L/K/deletion;
L235K/M/F/P/S/T/W/Y/V/A/R/N/D/C/Q/E/G/H/I/deletion;
N236D/C/Q/E/G/H/I/L/K/M/F/P/S/T/W/Y/V/A/R/deletion;
T237W/Y/V/A/R/N/D/C/Q/E/G/H/I/L/K/M/F/P/S/deletion;
P237S/T/W/Y/V/A/R/N/D/C/Q/E/G/H/I/L/K/M/F/deletion;
N238D/C/Q/E/G/H/I/L/K/M/F/P/S/T/W/Y/V/A/R/deletion;
H238I/L/K/M/F/P/S/T/W/Y/V/A/R/N/D/C/Q/E/G/deletion;
A238R/N/D/C/Q/E/G/H/I/L/K/M/F/P/S/T/W/Y/V/deletion;
S239T/W/Y/V/A/R/N/D/C/Q/E/G/H/I/L/K/M/F/P/deletion;
Q238E/G/H/I/L/K/M/F/P/S/T/W/Y/V/A/R/N/D/C/deletion;
K239M/F/P/S/T/W/Y/V/A/R/N/D/C/Q/E/G/H/I/L/deletion;
L247K/M/F/P/S/T/W/Y/V/A/R/N/D/C/Q/E/G/H/I/deletion;
N248D/C/Q/E/G/H/I/L/K/M/F/P/S/T/W/Y/V/A/R/deletion;
H248I/L/K/M/F/P/S/T/W/Y/V/A/R/N/D/C/Q/E/G/deletion;
F249P/S/T/W/Y/V/A/R/N/D/C/Q/E/G/H/I/L/K/M/deletion;
M250F/P/S/T/W/Y/V/A/R/N/D/C/Q/E/G/H/I/L/K/deletion;
G251H/I/L/K/M/F/P/S/T/W/Y/V/A/R/N/D/C/Q/E/deletion; and
V251A/R/N/D/C/Q/E/G/H/I/L/K/M/F/P/S/T/W/Y/deletion.

Accordingly, another aspect of the present invention contemplates a method for determining whether an HBV strain exhibits reduced sensitivity to a nucleoside or nucleotide analog or other potential anti-HBV agent, said method comprising isolating DNA or corresponding mRNA from said HBV and screening for a mutation in the nucleotide sequence of the envelope genes or DNA polymerase gene selected from, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment rtH90D and rtL/F108L; in even yet another embodiment, rtL157L/M, rtA181V and rtV207I; in even still another embodiment, rtL80V, rtP109S, rtI163V, rtL229M and rtN/H/A/S/Q238K; in another embodiment, rtS78S/T, rtN118N/S, rtN139N/K, rtV142E, rtA181A/T, rtI204M, rtQ/P/S/Stop215Q, rtE218K/E and rtN238N/H; in a further embodiment, sP120T, sM125T and sT127A; in yet another embodiment, sT118R, sM133T, SF134V, sI195M, sS207R and sY225Y/C; in still another embodiment, sS126T, sM133L/M, sS143S/T, sD144A, sG145A and sW172Stop; in even yet another embodiment, sN40S, sC69Stop, sM75I, sL88P, sT118A, sW182STOP, sW196L, sY206H and sY225F; in even still another embodiment, s181M and sP214Q; in another embodiment, sF83S, sL173F and sW199L; in a further embodiment, sI126T, sK160R, sS174N, sA184V, sW196L, sS210N, sF/C220L and sY221C; in yet another embodiment, sC69Stop/C, sC76Y sI110V/I, sY134N, sW172Stop/W, sW196Stop and sS207R; in still another embodiment, rtK32, rtN33, rtP34, rtH35 and rtT37; in even yet another embodiment, rtP59, rtK60, rtF61, rtA62 and rtV63; in even still another embodiment, rtD83, rtV84, rtS85, rtA86, rtY89, rtH90 and rtI/L91; in another embodiment, rtP177, rtF178, rtL179, rtL180, rtA181, rtQ182, rtF183 and rtT184; in a further embodiment, rtM204 and rtY203; in yet another embodiment, rt235, rt236, rt237, rt238 and rt239 in still another embodiment, rt247, rt248, rt249, rt250 and rt251; and in even yet another embodiment, K32M/F/P/S/T/W/Y/V/A/R/N/D/C/Q/E/G/H/I/L/deletion;
N33D/C/Q/E/G/H/I/L/K/M/F/P/S/T/W/Y/V/A/R/deletion;
P34S/T/W/Y/V/A/R/N/D/C/Q/E/G/H/I/L/K/M/F/deletion;
H35I/L/K/M/F/P/S/T/W/Y/V/A/R/N/D/C/Q/E/G/deletion;
T37W/Y/V/A/R/N/D/C/Q/E/G/H/I/L/K/M/F/P/S/deletion;
P59S/T/W/Y/V/A/R/N/D/C/Q/E/G/H/I/L/K/M/F/deletion;
K60M/F/P/S/T/W/Y/V/A/R/N/D/C/Q/E/G/H/I/L/deletion;
F61P/S/T/W/Y/V/A/R/N/D/C/Q/E/G/H/I/L/K/M/deletion;
A62R/N/D/C/Q/E/G/H/I/L/K/M/F/P/S/T/W/Y/V/deletion;
V63A/R/N/D/C/Q/E/G/H/I/L/K/M/F/P/S/T/W/Y/deletion;
D83C/Q/E/G/H/I/L/K/M/F/P/S/T/W/Y/V/A/R/N/deletion;
V84A/R/N/D/C/Q/E/G/H/I/L/K/M/F/P/S/T/W/Y/deletion;
S85T/W/Y/V/A/R/N/D/C/Q/E/G/H/I/L/K/M/F/P/deletion;
A86R/N/D/C/Q/E/G/H/I/L/K/M/F/P/S/T/W/Y/V/deletion;
Y89V/A/R/N/D/C/Q/E/G/H/I/L/K/M/F/P/S/T/W/deletion;
H90I/L/K/M/F/P/S/T/W/Y/V/A/R/N/D/C/Q/E/G/deletion;
I/L91K/M/F/P/S/T/W/Y/V/A/R/N/D/C/Q/E/G/H/deletion;
P177S/T/W/Y/V/A/R/N/D/C/Q/E/G/H/I/L/K/M/F/deletion;
F178P/S/T/W/Y/V/A/R/N/D/C/Q/E/G/H/I/L/K/M/deletion;
L179K/M/F/P/S/T/W/Y/V/A/R/N/D/C/Q/E/G/H/I/deletion;
L180K/M/F/P/S/T/W/Y/V/A/R/N/D/C/Q/E/G/H/I/deletion;
A181R/N/D/C/Q/E/G/H/I/L/K/M/F/P/S/T/W/Y/V/deletion;
Q183E/G/H/I/L/K/M/F/P/S/T/W/Y/V/A/R/N/D/C/deletion;

F183P/S/T/W/Y/V/A/R/N/D/C/Q/E/G/H/I/L/K/M/deletion; T184W/Y/V/A/R/N/D/C/Q/E/G/H/I/L/K/M/F/P/S/deletion; Y203V/A/R/N/D/C/Q/E/G/H/I/L/K/M/F/P/S/T/W/deletion; M204F/P/S/T/W/Y/V/A/R/N/D/C/Q/E/G/H/I/L/K/deletion; L235K/M/F/P/S/T/W/Y/V/A/R/N/D/C/Q/E/G/H/I/deletion; N236D/C/Q/E/G/H/I/L/K/M/F/P/S/T/W/Y/V/A/R/deletion; T237W/Y/V/A/R/N/D/C/Q/E/G/H/I/L/K/M/F/P/S/deletion; P237S/T/W/Y/V/A/R/N/D/C/Q/E/G/H/I/L/K/M/F/deletion; N238D/C/Q/E/G/H/I/L/K/M/F/P/S/T/W/Y/V/A/R/deletion; H238I/L/K/M/F/P/S/T/W/Y/V/A/R/N/D/C/Q/E/G/deletion; A238R/N/D/C/Q/E/G/H/I/L/K/M/F/P/S/T/W/Y/V/deletion; S239T/W/Y/V/A/R/N/D/C/Q/E/G/H/J/L/K/M/F/P/deletion; Q238E/G/H/I/L/K/M/F/P/S/T/W/Y/V/A/R/N/D/C; K239M/F/P/S/T/W/Y/V/A/R/N/D/C/Q/E/G/H/I/L; L247K/M/F/P/S/T/W/Y/V/A/R/N/D/C/Q/E/G/H/I; N248D/C/Q/E/G/H/I/L/K/M/F/P/S/T/W/Y/V/A/R; H248I/L/K/M/F/P/SIT/W/Y/V/A/R/N/D/C/Q/E/G; F249P/S/T/W/Y/V/A/R/N/D/C/Q/E/G/H/I/L/K/M; M250F/P/S/T/W/Y/V/A/R/N/D/C/Q/E/G/H/I/L/K; G251H/I/L/K/M/F/P/S/T/W/Y/V/A/R/N/D/C/QE; and V251A/R/N/D/C/Q/E/G/H/I/L/K/M/F/P/S/T/W/Y/deletion or combinations thereof or an equivalent one or more other mutation is indicative of a variant wherein said variant exhibits a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

The detection of amino acid variants of DNA polymerase is conveniently accomplished by reference to the amino acid sequence shown in Formulae I and II. The polymorphisms shown represent the variations shown in various databases for active pathogenic HBV strains. Where an HBV variant comprises an amino acid different to what is represented, then such an isolate is considered a putative HBV variant having an altered DNA polymerase activity.

The present invention further contemplates agents which inhibit ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV resistant HBV variants. Such agents are particularly useful if long term treatment by ADV, LMV, FTC and/or TFV and/or optionally other nucleoside analogs or nucleotide analogs such as TFV is contemplated by the clinician. The agents may be DNA or RNA or proteinaceous or non-proteinaceous chemical molecules. Natural product screening such as from plants, coral and microorganisms is also contemplated as a useful potential source of masking agents as is the screening of combinatorial or chemical libraries. The agents may be in isolated form or in the form of a pharmaceutical composition or formulation and may be administered in place of or sequentially or simultaneously with a nucleoside or nucleotide analog. Furthermore, rationale drug design is contemplated including solving the crystal or NMR structure of, for example, HBV DNA polymerase and designing agents which can bind to the enzyme's active site. This approach may also be adapted to other HBV components.

Accordingly, another aspect of the present invention contemplates a method for detecting an agent which exhibits inhibitory activity to an HBV which exhibits resistance or decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof, said method comprising:

generating a genetic construct comprising a replication competent-effective amount of the genome from said HBV contained in a plasmid vector and then transfecting said cells with said construct;

contacting said cells, before, during and/or after transfection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said agent.

Still another aspect of the present invention provides a method for detecting an agent which exhibits inhibitory activity to an HBV which exhibits resistance or decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof, said method comprising:

generating a genetic construct comprising a replication competent-effective amount of the genome from said HBV contained in or fused to an amount of a baculovirus genome effective to infect cells and then infecting said cells with said construct;

contacting said cells, before, during and/or after infection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said agent.

Preferably, the HBV genome is stably integrated into the cells' genome.

Particularly useful cells are 2.2.15 cells (Price et al., *Proc. Natl. Acad. Sci. USA* 86(21): 8541-8544, 1989 or AD cells (also known as HepAD32 cells or HepAD79 cells [Ying et al., *Viral Hepat.* 7(2): 161-165, 2000.

Whilst the baculovirus vector is a particularly useful in the practice of the present invention, the subject invention extends to a range of other vectors such as but not limited to adenoviral vectors.

The present invention further extends to cell lines (e.g. 2.2.15 or AD cells) carrying genetic constructs comprising all or a portion of an HBV genome or a gene or part of a gene therefrom.

The present invention also provides for the use of the subject HBV variants to screen for anti-viral agents. These anti-viral agents inhibit the virus. The term "inhibit" includes antagonizing or otherwise preventing infection, replication, assembly and/or release or any intermediate step. Preferred anti-viral agents include nucleoside or nucleotide analogs or anti-HBV agents, however, the present invention extends to non-nucleoside molecules.

In addition, rational drug design is also contemplated to identify or generate chemical molecules which either mimic a nucleoside or which interact with a particular nucleotide sequence or a particular nucleotide. Combinatorial chemistry and two hybrid screening are some of a number of techniques which can be employed to identify potential therapeutic or diagnostic agents.

In one example, the crystal structure or the NMR structure of polymerase or the surface antigen is used to rationally design small chemical molecules likely to interact with key regions of the molecule required for function and/or antigenicity. Such agents may be useful as inhibitors of polymerase activity and/or may alter an epitope on the surface antigen.

Several models of the HBV polymerase have been prepared due to the similarity with reverse transcriptase from HIV (Das et al, *J. Virol* 75(10): 4771-4779, 2001; Bartholomeusz et al., *Intervirology* 40(5-6): 337-342 1997; Allen et al., *Hepatology* 27(6): 1670-1677, 1998). The models of the HBV polymerase can be used for the rational drug design of new agents effective against HBV encoding the resistant mutations as well as wild type virus. The rational drug that is designed may be based on a modification of an existing antiviral agent such as the agent used in the selection of the HBV encoding the mutations associated with resistance. Viruses or clones expressing HBV genomic material encoding the mutations may also be used to screen for new antiviral agents.

In an alternative embodiment, the present invention also contemplates a method for detecting an agent which exhibits inhibitory activity to an HBV polymerase in an in vitro polymerase assay. The HBV polymerase activity can be examined using established assays (Gaillard et al., *Antimicrob Agents Chemother.* 46(4): 1005-1013, 2002; Xiong et al., *Hepatology* 28(6): 1669-1673, 1998).

As indicated above, microarray technology is also a useful means of identifying agents which are capable of interacting with defined HBV internal or external components. For example, arrays of HBV DNA polymerase or peptide fragments thereof carrying different amino acid variants may be used to screen for agents which are capable of binding or otherwise interacting with these molecules. This is a convenient way of determining the differential binding patterns of agents between HBV variants. Arrays of antibodies may also be used to screen for altered HBsAg molecules. Microarrays are also useful in proteomic analysis to identify molecules such as antibodies, interferons or cytokines which have an ability to interact with an HBV component. Microarrays of DNA and RNA molecules may also be employed to identify sense and antisense molecules for genetic regions on the HBV genome or transcripts thereof.

The above methods are particularly useful in identifying an inhibitor of an HBV resistant to or exhibiting reduced sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof. The present invention extends, therefore, to compositions of the inhibitors. The inhibitors may also be in the form of antibodies or genetic molecules such as ribozymes, antisense molecules and/or sense molecules for co-suppression or the induction of RNAi or may be other nucleoside or nucleotide analogs or other anti-HBV agents or derivatives of known analogs. Reference to RNAi includes reference to short, interfering RNAs (siRNA).

The term "composition" includes a "pharmaceutical composition" or a formulation.

The inhibitor is referred to below as an "active ingredient" or "active compound" and may be selected from the list of inhibitors given above.

The composition may include an antigenic component of the HBV, a defective HBV variant or an agent identified through natural product screening or rational drug design (including combinatorial chemistry).

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The pharmaceutical composition may also comprise genetic molecules such as a vector capable of transfecting target cells where the vector carries a nucleic acid molecule capable of encoding an aspartyl protease inhibitor. The vector may, for example, be a viral vector.

Pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

When the active ingredient is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 200 mg of active compound. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and a flavouring. Of course, any material used in preparing any dosage unit form should be pharmaceutically pure and substantially non-toxic in the amounts employed. In addition, the active compound(s) may be incorporated into sustained-release preparations and formulations.

As stated above, the present invention further extends to an isolated HBsAg from the HBV variants herein described. More particularly, the present invention provides an HBsAg or a recombinant form thereof or derivative or chemical equivalent thereof. The isolated surface component and, more particularly, isolated surface antigen or its recombinant, derivative or chemical equivalents are useful in the development of biological compositions such as vaccine formulations.

Yet another aspect of the present invention provides a composition comprising a variant HBV resistant to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or an HBV surface antigen from said variant HBV or a recombinant or derivative form thereof or its chemical equivalent and one or more pharmaceutically acceptable carriers and/or diluents. Such a composition may be regarded as a therapeutic composition and is useful in generating an immune response including a humoral response. Generally, the HBV variants are "defective" and in themselves are unable to cause a sustained infection in a subject.

As indicated above, antibodies may be generated to the mutant HBV agents and used for passive or direct vaccination against infection by these viruses. The antibodies may be generated in humans or non-human animals. In the case of the latter, the non-human antibodies may need to be deimmunized or more specifically humanized prior to use. Deimmunized may include, for example, grafting complimentarity determining regions (CDRs) from the variable region of a murine or non-human animal anti-HBV antibody onto a human consensus fragment antibody binding (Fab) polypeptide. Alternatively, amino acids defining epitopes in the variable region of the antibody may be mutated so that the epitopes are no longer recognized by the human MHC II complex.

Insofar as ribozyme, antisense or co-suppression (RNAi) or siRNA or complexes thereof repression is concerned, this is conveniently aimed at post-transcription gene silencing. DNA or RNA may be administered or a complex comprising RNAi or a chemical analog thereof specific for HBV mRNA may be employed.

All such molecules may be incorporated into pharmaceutical compositions.

In another embodiment, the present invention provides a biological composition comprising a variant HBV or an HBsAg or L, M or S proteins from said variant HBV or a recombinant or derivative form thereof or its chemical equivalent.

Generally, if an HBV is used, it is first attenuated. The biological composition according to this aspect of the present invention generally further comprises one or more pharmaceutically acceptable carriers and/or diluents.

The biological composition may comprise HBsAg or like molecule from one HBV variant or the composition may be a cocktail of HbsAgs or L, M or S proteins or like molecules from a range of ADV- and/or LMV- and/or, FTC- and/or TFV-resistant HBV variants. Similar inclusions apply where the composition comprises an HBV.

The present invention is further directed to the use of defective HBV variants in the manufacture of therapeutic vaccines to vaccinate individuals against infection by HBV strains having a particular nucleotide sequence or encoding a particular polymerase or surface antigen or L, M or S proteins.

Examples of suitable vaccine candidates are defective forms of HBV variants comprising a mutation selected from, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment rtH90D and rtL/F108L; in even yet another embodiment, rtL157L/M, rtA181V and rtV207I; in even still another embodiment, rtL80V, rtP109S, rtI163V, rtL229M and rtN/H/A/S/Q238K; in another embodiment, rtS78S/T, rtN118N/S, rtN139N/K, rtV142E, rtA181A/T, rtI204M, rtQ/P/S/Stop215Q, rtE218K/E and rtN238N/H; in a further embodiment, sP120T, sM125T and sT127A; in yet another embodiment, sT118R, sM133T, SF134V, sI195M, sS207R and sY225Y/C; in still another embodiment, sS126T, sM133L/M, sS143S/T, sD144A, sG145A and sW172Stop; in even yet another embodiment, sN40S, sC69Stop, sM75I, sL88P, sT118A, sW182STOP, sW196L, sY206H and sY225F; in even still another embodiment, s181M and sP214Q; in another embodiment, sF83S, sL173F and sW199L; in a further embodiment, sI126T, sK160R, sS174N, sA184V, sW196L, sS210N, sF/C220L and sY221C; in yet another embodiment, sC69Stop/C, sC76Y sI110V/I, sY134N, sW172Stop/W, sW196Stop and sS207R; in still another embodiment, rtK32, rtN33, rtP34, rtH35 and rtT37; in even yet another embodiment, rtP59, rtK60, rtF61, rtA62 and rtV63; in even still another embodiment, rtD83, rtV84, rtS85, rtA86, rtY89, rtH90 and rtI/L91; in another embodiment, rtP177, rtF178, rtL179, rtL180, rtA181, rtQ182, rtF183 and rtT184; in a further embodiment, rtM204 and rtY203; in yet another embodiment, rt235, rt236, rt237, rt238 and rt239 in still another embodiment, rt247, rt248, rt249, rt250 and rt251; and in even yet another embodiment, K32M/F/P/S/T/W/Y/V/A/R/N/D/C/Q/E/G/H/I/L/deletion;

N33D/C/Q/E/G/H/I/L/K/M/F/P/SIT/W/Y/V/A/R/deletion;

P34S/T/W/Y/V/A/R/N/D/C/Q/E/G/H/I/L/K/M/F/deletion;

H35I/L/K/M/F/P/S/T/W/Y/V/A/R/N/D/C/Q/E/G/deletion;

T37W/Y/V/A/R/N/D/C/Q/E/G/H/J/L/K/M/F/P/S/deletion;

P59S/T/W/Y/V/A/R/N/D/C/Q/E/G/H/I/L/K/M/F/deletion;

K60M/F/P/S/T/W/Y/V/A/R/N/D/C/Q/E/G/H/I/L/deletion;

F61P/S/T/W/Y/V/A/R/N/D/C/Q/E/G/H/I/L/K/M/deletion;

A62R/N/D/C/Q/E/G/H/I/L/K/M/F/P/S/T/W/Y/V/deletion;

V63A/R/N/D/C/Q/E/G/H/I/L/K/M/F/P/S/T/W/Y/deletion;

D83C/Q/E/G/H/I/L/K/M/F/P/S/T/W/Y/V/A/R/N/deletion;

V84A/R/N/D/C/Q/E/G/H/I/L/K/M/F/P/S/T/W/Y/deletion;

S85T/W/Y/V/A/R/N/D/C/Q/E/G/H/I/L/K/M/F/P/deletion;

A86R/N/D/C/Q/E/G/H/I/L/K/M/F/P/S/T/W/Y/V/deletion;

Y89V/A/R/N/D/C/Q/E/G/H/I/L/K/M/F/P/S/T/W/deletion;

H90I/L/K/M/F/P/S/T/W/Y/V/A/R/N/D/C/Q/E/G/deletion;

I/L91K/M/F/P/S/T/W/Y/V/A/R/N/D/C/Q/E/G/H/deletion;

P177S/T/W/Y/V/A/R/N/D/C/Q/E/G/H/I/L/K/M/F/deletion;

F178P/S/T/W/Y/V/A/R/N/D/C/Q/E/G/H/I/L/K/M/deletion;

L179K/M/F/P/S/T/W/Y/V/A/R/N/D/C/Q/E/G/H/I/deletion;

L180K/M/F/P/S/T/W/Y/V/A/R/N/D/C/Q/E/G/H/I/deletion;

A181R/N/D/C/Q/E/G/H/I/L/K/M/F/P/S/T/W/Y/V/deletion;

Q183 E/G/H/I/L/K/M/F/P/S/T/W/Y/V/A/R/N/D/C/deletion;

F183P/S/T/W/Y/V/A/R/N/D/C/Q/E/G/H/I/L/K/M/deletion;

T184W/Y/V/A/R/N/D/C/Q/E/G/H/I/L/K/M/F/P/S/deletion;

Y203V/A/R/N/D/C/Q/E/G/H/I/L/K/M/F/P/S/T/W/deletion;

M204F/P/S/T/W/Y/V/A/R/N/D/C/Q/E/G/H/I/L/K/deletion;

L235K/M/F/P/S/T/W/Y/V/A/R/N/D/C/Q/E/G/H/I/deletion;

N236D/C/Q/E/G/H/I/L/K/M/F/P/S/T/W/Y/V/A/R/deletion;

T237W/Y/V/A/R/N/D/C/Q/E/G/H/I/L/K/M/F/P/S/deletion;

P23-7S/T/W/Y/V/A/R/N/D/C/Q/E/G/H/I/L/K/M/F/deletion;

N238D/C/Q/E/G/H/I/L/K/M/F/P/S/T/W/Y/V/A/R/deletion;

H238I/L/K/M/F/P/S/T/W/Y/V/A/R/N/D/C/Q/E/G/deletion;

A238R/N/D/C/Q/E/G/H/I/L/K/M/F/P/S/T/W/Y/V/deletion;

S239T/W/Y/V/A/R/N/D/C/Q/E/G/H/I/L/K/M/F/P/deletion;

Q238E/G/H/I/L/K/M/F/P/S/T/W/Y/V/A/R/N/D/C/deletion;

K239M/F/P/S/T/W/Y/V/A/R/N/D/C/Q/E/G/H/I/L/deletion;

L247K/M/F/P/S/T/W/Y/V/A/R/N/D/C/Q/E/G/H/I/deletion;

N248D/C/Q/E/G/H/I/L/K/M/F/P/S/T/W/Y/V/A/R/deletion;

H248I/L/K/M/F/P/S/T/W/Y/V/A/R/N/D/C/Q/E/G/deletion;

F249P/S/T/W/Y/V/A/R/N/D/C/Q/E/G/H/I/L/K/M/deletion;

M250F/P/S/T/W/Y/V/A/R/N/D/C/Q/E/G/H/I/L/K/deletion;

G251H/I/L/K/M/F/P/S/T/W/Y/V/A/R/N/D/C/Q/E; and

V251A/R/N/D/C/Q/E/G/H/I/L/K/M/F/P/S/T/W/Y/deletion or a combination of two or more mutations.

In one embodiment, for example, an HBV variant may be identified having a particular mutation in its polymerase conferring resistance or decreased sensitivity to a nucleoside analog. This variant may then be mutated to render it defective, i.e. attenuated or unable to cause infection. Such a defective, nucleoside analog-resistant virus may then be used as a therapeutic vaccine against virulent viruses having the same mutation in its polymerase.

The subject invention extends to kits for assays for variant HBV resistant to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV. Such kits may, for example, contain the reagents from PCR or other nucleic acid hybridization technology or reagents for immunologically based detection techniques. A particularly useful assay includes the reagents and components required for immobilized oligonucleotide- or oligopeptide-mediated detection systems.

Still another aspect of the present invention contemplates a method for determining the potential for an HBV to exhibit reduced sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and domains A through to E or a region proximal thereto of said DNA polymerase and associated with resistance or decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV, wherein the presence of such a mutation is an indication of the likelihood of resistance to said ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV.

An assessment of a potential viral variant is important for selection of an appropriate therapeutic protocol. Such an assessment is suitably facilitated with the assistance of a computer programmed with software, which inter alia adds index values ($I_Vs$) for at least two features associated with the viral variants to provide a potency value ($P_A$) corresponding to the resistance or sensitivity of a viral variant to a particular chemical compound or immunological agent. The $I_Vs$ can be selected from (a) the ability to exhibit resistance for reduced sensitivity to a particular compound or immunological agent;

(b) an altered DNA polymerase from wild-type HBV; (c) an altered surface antigen from wild-type HBV; or (d) morbidity or recovery potential of a patient. Thus, in accordance with the present invention, $I_Fs$ for such features are stored in a machine-readable storage medium, which is capable of processing the data to provide a $P_A$ for a particular viral variant or a biological specimen comprising same.

Thus, in another aspect, the invention contemplates a computer program product for assessing the likely usefulness of a viral variant or biological sample comprising same for determining an appropriate therapeutic protocol in a subject, said product comprising:
(1) code that receives as input $I_Fs$ for at least two features associated with said viral agents or biological sample comprising same, wherein said features are selected from:
  (a) the ability to exhibit resistance for reduced sensitivity to a particular compound or immunological agent;
  (b) an altered DNA polymerase from wild-type HBV;
  (c) an altered surface antigen from wild-type HBV;
  (d) morbidity or recovery potential of a patient; or
  (e) altered replication capacity (increased or decreased);
(2) code that adds said $I_Fs$ to provide a sum corresponding to a $P_V$ for said viral variants or biological samples; and
(3) a computer readable medium that stores the codes.

In a related aspect, the invention extends to a computer for assessing the likely usefulness of a viral variant or biological sample comprising same in a subject, wherein said computer comprises:
(1) a machine-readable data storage medium comprising a data storage material encoded with machine-readable data, wherein said machine-readable data comprise $I_Fs$ for at least two features associated with said viral variant or biological sample; wherein said features are selected from:—
  (a) the ability to exhibit resistance for reduced sensitivity to a particular compound or immunological agent;
  (b) an altered DNA polymerase from wild-type HBV;
  (c) an altered surface antigen from wild-type HBV;
  (d) morbidity or recovery potential of a patient; or
  (e) altered replication capacity (increased or decreased);
(2) a working memory for storing instructions for processing said machine-readable data;
(3) a central-processing unit coupled to said working memory and to said machine-readable data storage medium, for processing said machine readable data to provide a sum of said $I_Fs$ corresponding to a $P_V$ for said compound(s); and
(4) an output hardware coupled to said central processing unit, for receiving said $P_V$.

Figure 19:
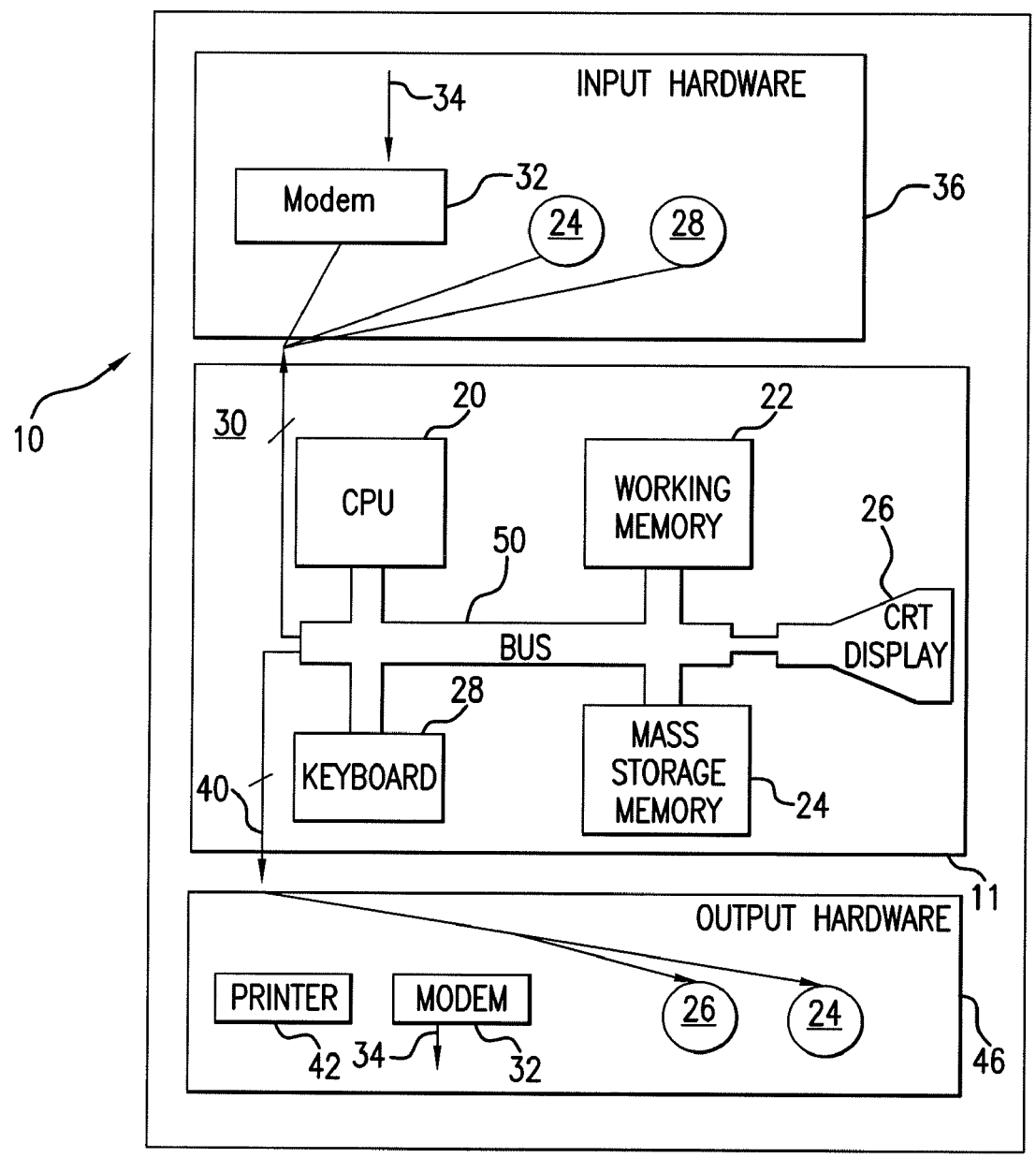
FIG. 19 is a diagrammatic representation of a system used to carry out the instructions encoded by the storage medium.

Any general or special purpose computer system is contemplated by the present invention and includes a processor in electrical communication with both a memory and at least one input/output device, such as a terminal. FIG. 19 shows a generally suitable computer system. Such a system may include, but is not limited, to personal computers, workstations or mainframes. The processor may be a general purpose processor or microprocessor or a specialized processor executing programs located in RAM memory. The programs may be placed in RAM from a storage device, such as a disk or pre-programmed ROM memory. The RAM memory in one embodiment is used both for data storage and program execution. The computer system also embraces systems where the processor and memory reside in different physical entities but which are in electrical communication by means of a network.

In an alternative embodiment, the program screens for a mutation selected from, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment rtH90D and rtL/F108L; in even yet another embodiment, rtL157L/M, rtA181V and rtV207I; in even still another embodiment, rtL80V, rtP109S, rtI163V, rtL229M and rtN/H/A/S/Q238K; in another embodiment, rtS78S/T, rtN118N/S, rtN139N/K, rtV142E, rtA181A/T, rtI204M, rtQ/P/S/Stop215Q, rtE218K/E and rtN238N/H; in a further embodiment, sP120T, sM125T and sT127A; in yet another embodiment, sT118R, sM133T, SF134V, sI195M, sS207R and sY225Y/C; in still another embodiment, sS126T, sM133L/M, sS143S/T, sD144A, sG145A and sW172Stop; in even yet another embodiment, sN40S, sC69Stop, sM75I, sL88P, sT118A, sW182STOP, sW196L, sY206H and sY225F; in even still another embodiment, s181M and sP214Q; in another embodiment, sF83S, sL173F and sW199L; in a further embodiment, sI126T, sK160R, sS174N, sA184V, sW196L, sS210N, sF/C220L and sY221C; in yet another embodiment, sC69Stop/C, sC76Y sI110V/I, sY134N, sW172Stop/W, sW196Stop and sS207R; in still another embodiment, rtK32, rtN33, rtP34, rtH35 and rtT37; in even yet another embodiment, rtP59, rtK60, rtF61, rtA62 and rtV63; in even still another embodiment, rtD83, rtV84, rtS85, rtA86, rtY89, rtH90 and rtI/L91; in another embodiment, rtP177, rtF178, rtL179, rtL180, rtA181, rtQ182, rtF183 and rtT184; in a further embodiment, rtM204 and rtY203; in yet another embodiment, rt235, rt236, rt237, rt238 and rt239 in still another embodiment, rt247, rt248, rt249, rt250 and rt251; and in even yet another embodiment, K32M/F/P/S/T/W/Y/V/A/R/N/D/C/Q/E/G/H/I/L/deletion;

N33D/C/Q/E/G/H/I/L/K/M/F/P/S/T/W/Y/V/A/R/deletion;

P34S/T/W/Y/V/A/R/N/D/C/Q/E/G/H/I/L/K/M/F/deletion;

H35I/L/K/M/F/P/S/T/W/Y/V/A/R/N/D/C/Q/E/G/deletion;

T37W/Y/V/A/R/N/D/C/Q/E/G/H/I/L/K/M/F/P/S/deletion;

P59S/T/W/Y/V/A/R/N/D/C/Q/E/G/H/I/L/K/M/F/deletion;

K60M/F/P/S/T/W/Y/V/A/R/N/D/C/Q/E/G/H/I/L/deletion;

F61P/S/T/W/Y/V/A/R/N/D/C/Q/E/G/H/I/L/K/M/deletion;

A62R/N/D/C/Q/E/G/H/I/L/K/M/F/P/S/T/W/Y/V/deletion;

V63A/R/N/D/C/Q/E/G/H/I/L/K/M/F/P/S/T/W/Y/deletion;

D83C/Q/E/G/H/I/L/K/M/F/P/S/T/W/Y/V/A/R/N/deletion;

V84A/R/N/D/C/Q/E/G/H/I/L/K/M/F/P/S/T/W/Y/deletion;

S85T/W/Y/V/A/R/N/D/C/Q/E/G/H/I/L/K/M/F/P/deletion;

A86R/N/D/C/Q/E/G/H/I/L/K/M/F/P/S/T/W/Y/V/deletion;

Y89V/A/R/N/D/C/Q/E/G/H/I/L/K/M/F/P/S/T/W/deletion;

H90I/L/K/M/F/P/S/T/W/Y/V/A/R/N/D/C/Q/E/G/deletion;

I/L91K/M/F/P/S/T/W/Y/V/A/R/N/D/C/Q/E/G/H/deletion;

P177S/T/W/Y/V/A/R/N/D/C/Q/E/G/H/I/L/K/M/F/deletion;

F178P/S/T/W/Y/V/A/R/N/D/C/Q/E/G/H/I/L/K/M/deletion;

L179K/M/F/P/S/T/W/Y/V/A/R/N/D/C/Q/E/G/H/I/deletion;

L180K/M/F/P/S/T/W/Y/V/A/R/N/D/C/Q/E/G/H/I/deletion;

A181R/N/D/C/Q/E/G/H/I/L/K/M/F/P/S/T/W/Y/V/deletion;

Q183 E/G/H/I/L/K/M/F/P/S/T/W/Y/V/A/R/N/D/C/deletion;
F183P/S/T/W/Y/V/A/R/N/D/C/Q/E/G/H/I/L/K/M/deletion;
T184W/Y/V/A/R/N/D/C/Q/E/G/H/I/L/K/M/F/P/S/deletion;
Y203V/A/R/N/D/C/Q/E/G/H/I/L/K/M/F/P/S/T/W/deletion;
M204F/P/S/T/W/Y/V/A/R/N/D/C/Q/E/G/H/I/L/K/deletion;
L235K/M/F/P/S/T/W/Y/V/A/R/N/D/C/Q/E/G/H/I/deletion;
N236D/C/Q/E/G/H/I/L/K/M/F/P/S/T/W/Y/V/A/R/deletion;
T237W/Y/V/A/R/N/D/C/Q/E/G/H/I/L/K/M/F/P/S/deletion;
P237S/T/W/Y/V/A/R/N/D/C/Q/E/G/H/I/L/K/M/F/deletion;
N238D/C/Q/E/G/H/I/L/K/M/F/P/S/T/W/Y/V/A/R/deletion;
H238I/L/K/M/F/P/S/T/W/Y/V/A/R/N/D/C/Q/E/G/deletion;
A238R/N/D/C/Q/E/G/H/I/L/K/M/F/P/S/T/W/Y/V/deletion;
S239T/W/Y/V/A/R/N/D/C/Q/E/G/H/I/L/K/M/F/P/deletion;
Q238E/G/H/I/L/K/M/F/P/S/T/W/Y/V/A/R/N/D/C/deletion;
K239M/F/P/S/T/W/Y/V/A/R/N/D/C/Q/E/G/H/I/L/deletion;
L247K/M/F/P/S/T/W/Y/V/A/R/N/D/C/Q/E/G/H/I/deletion;
N248D/C/Q/E/G/H/I/L/K/M/F/P/S/T/W/Y/V/A/R/deletion;
H248I/L/K/M/F/P/S/T/W/Y/V/A/R/N/D/C/Q/E/G/deletion;
F249P/S/T/W/Y/V/A/R/N/D/C/Q/E/G/H/I/L/K/M/deletion;
M250F/P/S/T/W/Y/V/A/R/N/D/C/Q/E/G/H/I/L/K/deletion;
G251H/I/L/K/M/F/P/S/T/W/Y/V/A/R/N/D/C/Q/E; and
V251A/R/N/D/C/Q/E/G/H/I/L/K/M/F/P/S/T/W/Y/deletion
or a combination of two or more mutations.

The present invention is further described by the following non-limiting Examples.

Example 1

Overlapping Genome of HBV

The overlapping genome of HBV is represented in FIG. 1. The gene encoding DNA polymerase (P), overlaps the viral envelope genes, Pre-S1 and Pre-S2, and partially overlaps the X and core (C) genes. The HBV envelope comprises small, middle and large proteins HBV surface antigens. The large protein component is referred to as the HBV surface antigen (HBsAg) and is encoded by the S gene sequence. The Pre-S1 and Pre-S2 gene sequences encode the other envelope components.

Example 2

Patients and Treatment

Patient A, a 48 year old Lebanese woman was initially referred for evaluation of thrombocytopenia and hepatosplenomegaly. At this time the patient had abnormal LFT's (ALT 67 U/L, normal <55) and the HBV DNA was 61 pg/ml (231 days prior to the start of treatment). The patient was HBsAg and HBeAg positive. The ALT's fluctuated between 50-70 IU/L from (−231 to −35 days pretreatment). ADV was commenced on Day 0 in a clinical trial on 30 mg/day. HBV DNA levels were reduced with ADV treatment. The ADV treatment was reduced to 10 mg/day (144 days post-treatment). There was a problem with the randomization treatment protocol. The patient was on antiviral treatment for 1 month only during the second year of the treatment period. The study was completed on Day 679 post ADV treatment. The patient was not on ADV treatment until the open label ADV was recommenced on Day 875 from the start of the initial ADV treatment. This second period of ADV treatment was given for 108 days (day 983 post initial ADV treatment). The HBV DNA levels remained at 7-10 pg/ml ($1.96\times10^5$ to $2.8\times10^5$ copies/ml). At Day 983, ADV treatment was stopped and the patient was treated with LMV.

Patient B is a male liver transplant patient. The patient has been on both sequential and combination antiviral therapy including HBIG, FCV+HBIG, LMV+HBIG, LMV, LMV+GCV, LMV+FCV+GCV, LMV+GCV and finally LMV+ADV. The patient has been on long term ADV+LMV treatment for over 795 days.

Patient C, is a 58 year old male. Prior to ADV treatment the patient had abnormal LFT's (ALT 240 IU/L, normal <55) and the HBV DNA was $2\times10^7$ copies/ml. ADV was commenced on Day 0 in a clinical trial on 10 mg/day for two years. The average ALT during the two year clinical trial period was 114 IU/L. However, the ALT was rising and at 630 days after the start of ADV treatment the ALT remained high 407 IU/L. Open label ADV was commenced on Day 668 from the start of the initial ADV treatment. This second period of ADV treatment was given for 71 days. The HBV DNA levels remained high during open label ADV treatment ($3.7\times10^6$ to $1.5\times10^7$ copies/ml). The peak ALT during open label ADV treatment was 517 IU/L (Day 738). The next day (Day 739), ADV treatment was stopped and the patient was treated with LMV.

Example 3

Detection of Viral Markers

Hepatitis B surface antigen (HBsAg), hepatitis B e antigen (HBeAg), anti-HBe and hepatitis B core antigen (HBcAg) specific IgG and IgM were measured using commercially available immunoassays (Abbott Laboratories, North Chicago, Ill., USA). Hepatitis B viral DNA levels were measured using a capture hybridization assay according to the manufacturer's directions (Digene Hybrid Capture II, Digene Diagnostics Inc., Beltsville, Md.). The manufacturers stated cut-off for detecting HBV viremia in clinical specimens was $0.7\times10^6$ copies/ml or 2.5 pg/ml, [Hendricks et al., *Am J Clin Pathol* 104: 537-46, 1995]. HBV DNA levels can also be quantitated using other commercial kits such as Cobas amplification HBV monitor kit (Roche).

Example 4

Sequencing of HBV DNA

HBV DNA was extracted from 100 μl of serum as described previously by Aye et al., *J. Hepatol.* 26: 1148-1153, 1997. Oligonucleotides were synthesized by Geneworks, Adelaide, Australia. Amplification of the HBV polymerase gene has been described by Aye et al., 1997, supra.

The specific amplified products were purified using PCR purification columns from MO BIO Laboratories Inc (La Jolla, Calif.) and directly sequenced using Big Dye terminator Cycle sequencing Ready Reaction Kit (Perkin Elmer, Cetus Norwalk, Conn.). The PCR primers were used as sequencing primers, OS1 5'-GCC TCA TTT TGT GGG TCA CCA TA-31 (nt 1408-1430) [SEQ ID NO:3], TTA3 5'-AAA TTC GCA GTC CCC AAA-3'(nt2128-2145) [SEQ ID NO:4], JM 5'-TTG GGG TGG AGC CCT CAG GCT-3'

(nt1676-1696) [SEQ ID NO:5], TTA4 5'-GAA AAT TGG TAA CAG CGG-3'(nt 2615-2632) [SEQ ID NO:6], OS2 5'TCT CTG ACA TAC TTT CCA AT 3'(nt 2798-2817) [SEQ ID NO:7], to sequence the internal regions of the PCR products.

Example 5

Analysis of HBV DNA

Patient A: During ADV treatment, unique HBV mutations were detected by sequencing (Tables 4 and 5) This includes the unique mutation at rtY135C in addition to the mutation at rtT128N that was present prior to ADV treatment. A number of other unique changes were also detected in the polymerase and in the overlapping envelope gene (Table 5, FIGS. 4, 5 and 6). The unique change in the HBsAg include sP120T. These unique changes were compared to reference sequences from each of the seven genotypes A-G as well as a consensus sequence from pretreatment samples to determine unique changes.

Patient B: The HBV mutations prior to ADV treatment and during ADV treatment are listed in Table 6 and 7 and FIGS. 7, 8, and 9. The unique changes in the rt region of the HBV DNA polymerase include rtN/S/T/I/V53D, rtY126Q, rtL180M, rtS202G, rtI204V and rtI235I/M. The unique changes in the HBsAg include sT118R, sM133T, sF134V, sI195M, sS207R, sY225Y/C.

Patient C: The HBV mutations prior to ADV treatment and during ADV treatment are listed in Tables 8 and 9 and FIGS. 10, 11 and 12. The unique changes in the rt region of the HBV DNA polymerase include rtN53D, rtS116P, rtF151F/T, rtN236T and rtN238D. The unique changes in the HBsAg include sG145A and sW172stop.

Patient D: The HBV mutations during ADV treatment is listed in Table 10 and FIGS. 13, 14 and 15. The unique changes in the HBV DNA polymerase include rtS78T, rtV84M, rtY126C, rtV191I, rtM204I and rtV214A. The unique changes in the surface include sN40S and sC69 Stop. A number of unique changes were detected after the stop codon mutation at codon 69 of the S gene including sM75I, sL88P, sT118A, sW182stop, sW196L, sY206H and sY225F.

Patient E: The HBV mutations during ADV treatment is listed in Table 11 and FIGS. 16, 17 and 18. The unique changes in the HBV DNA polymerase include rtH90D and rtL/F108L.

The unique changes in the surface include sI81M and sP214Q. A six nucleotide insertion was also detected resulting in a two amino acid insertion in the HBV polymerase and envelope gene at codons rt131 and s122, respectively. This insertion was previously detected in pre-ADV samples.

Example 6

Adefovir Dipivoxil (ADV)

Figure 2:
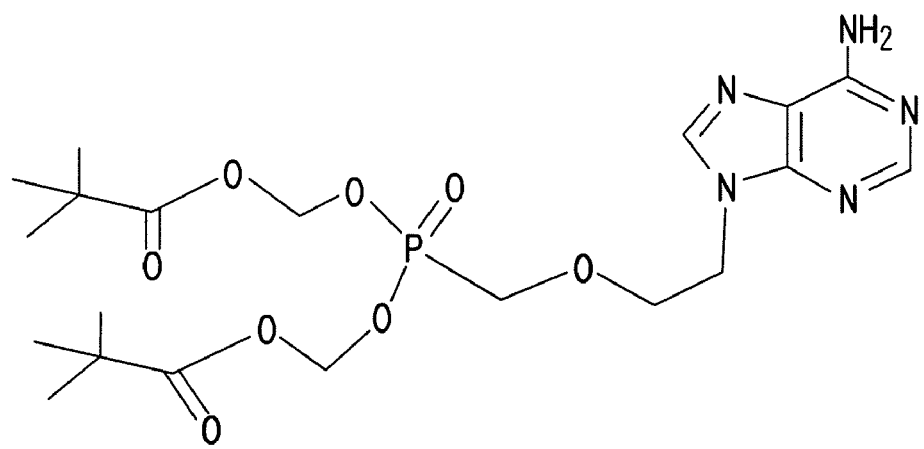
FIG. 2 is a diagrammatic representation of the chemical structure of ADV.
Figure 3:
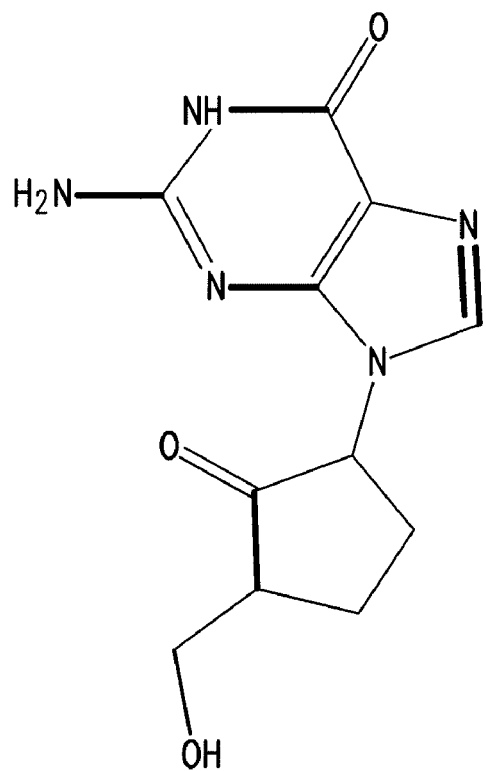
FIG. 3 is a diagrammatic representation of a computer system for determining the potency value ($P_A$) of a variant HBV.

ADV (formerly Bis-pom PMEA)) is a potent inhibitor of HBV replication. The structure of ADV is shown in FIG. 2 and its synthesis is described by Benzaria et al, *J Med. Chem.* 39: 4958-4965, 1996).

Example 7

HBV rt Mutants

The HBV polymerase has similarities to other polymerases including HIV. Thus, mutations associated with resistance to antiviral agents may occur within the polymerase in functionally important regions such as the nucleotide triphosphate binding pocket that may also include the interaction between the DNA primer and template strand, magnesium ions and nucleoside triphosphates or nucleoside/nucleotide analogs (and there various phosphroylated forms). Codons which are proposed to be mutated during anti-viral selection pressure are rtK32, rt N33, rtP34, rtH35 and rtT37 (that are upstream from the F domain); rt P59, rtK60, rtF61, rtA62 and rtV63 (between the F and A domains), rtD83, rtV84, rtS85, rtA86, rt Y89, rt H90 and rtI/L91 (within the A domain and the region immediately prior to and after), rtP177, rtF178, rt L179, rtL180, rtA181, rtQ182, rtF183 and rtT184 (B domain); rtM204 and rtY203 (C Domain), rtL235, rtN236, rtP/T237, rtN/H/A/S/Q238 and rtK239 (D Domain), rLt247, rtN/H248, rtF249, rtM250 and rtG251 (E Domain). The codons are defined in Table 12 and examples of various mutants are given in Tables 13 and 14.

Example 8

Patient F

The HBV mutations during ADV treatment of Patient F are listed in Table 15 and FIGS. 20, 21 and 22. The unique changes in the HBV DNA polymerase includes rtL157L/M, rtA181V, rtV207I, and rtN236T. The unique changes in the surface includes sF83 S, sL173F and sW199L.

Example 9

Patient G

The HBV mutations during ADV treatment of Patient G are listed in Table 16 and FIGS. 23, 24 and 25. The unique changes in the HBV DNA polymerase includes rtL80V, rtP109S, rtI163V, rtM204I, rtL229M and rtN/H/A/S/Q238K. The unique changes in the surface includes sI126T, sK160R, sS174N, sA184V, sW196L, sS210N, sF/C220L and sY221C.

Example 10

Patient H

The HBV mutations during ADV treatment in Patient H are listed in Table 17 and FIGS. 26, 27 and 28. The unique changes in the HBV DNA polymerase includes rtS78S/T, rtN118N/S, rtN139N/K, rtV142E, rtA181A/T, rtI204M, rtQ/P/S/Stop215Q, rtE218K/E, and rtN238N/H. The unique changes in the surface include sC69Stop/C, sC76Y sI110V/I, sY134N, sW172Stop/W, sW196Stop and sS207R.

Example 11

In Vitro Analysis of ADV Resistance

The sensitivity/resistance profile of HBV mutants to ADV was examined in vitro using recombinant HBV/baculovirus. The procedure for analyzing the resistance profile is outlined in the following Examples 12-20.

Example 12

Cell Culture

Sf21 insect cells were maintained in supplemented Grace's insect medium further supplemented with 10% v/v heat-inactivated fetal bovine serum (Gibco BRL, Gaithersburg, Md.) in humidified incubator at 28° C. with $CO_2$. HepG2 cells were maintained in minimal essential medium supplemented with 10% v/v heat-inactivated fetal bovine serum (MEM-FBS). HepG2 cells were grown in humidified 37° C. incubators at 5% v/v $CO_2$.

Example 13

Preparation of HBV/baculovirus Transfer Vector with Specific Point Mutations

The recombinant HBV/baculovirus system used for antiviral testing has been previously described (Delaney et al., *Antimicrob Agents Chemother* 45(6): 1705-1013, 2001). In brief, the recombinant transfer vector was created by excising a fragment containing the 1.3×HBV genome construct and cloning it into the multiple cloning region of a baculovirus vector pBlueBac4.5 (Invitrogen, Carlsbad, Calif.). Point mutations were created by site directed mutagenesis using the commercial kits according to the manufacturer's specifications (QuikChange, Stratagene). HBV/baculovirus recombinant clones encoding the reverse transcriptase mutations rtA181T/N236T/N238D and rtN236T/N236D in combination with the precore mutation at G1896A (pcW28 stop) or wild-type with respect to codon pcW28, were prepared by site-directed mutagenesis. The nucleotide sequence of the plasmid and the point mutations generated by site directed mutagenesis were confirmed by sequencing using the ABI Prism Big Dye Terminator Cycle Sequencing Ready Reaction Kit according to the manufacturer's specifications (Perkin Elmer, Cetus Norwalk, Conn.).

Example 14

Generation of Recombinant Baculoviruses Containing the 1.3 HBV Construct

Purified recombinant transfer vector and linear AcMNPV baculovirus DNA were co-transfected into Sf21 cells using the BacNBlue transfection kit from Invitrogen (Carlsbad, Calif.); recombinant viruses were isolated by plaque assay according to the manufacturer's instructions. A series of recombinant viruses were amplified from isolated plaques by infecting 100-mm dishes of Sf21 cells. Viral DNA was extracted from amplified viruses using standard procedures. Purified viral DNA was digested with restriction enzymes and then fractionated by electrophoresis in a 1% v/v agarose gel. Southern blotting was performed to determine which virus isolates contained the intact 1.3 HBV construct. A Boehringer Mannheim Random Prime DNA Labeling kit (Indianapolis, Ind.) was used to generate [$P^{32}$]-radiolabeled probes. A full-length double-stranded HBV genome was used as a template for all radiolabeled probes. Viral DNA sequence was confirmed by PCR amplification of the polymerase catalytic region using the sense primer 5'-GCC TCA TTT TGT GGG TCA CCA TA-3' [SEQ ID NO:8], (nucleotide 1408 to 1430 according to HBV Genebank Accession number M38454) and the antisense primer 5'-TCT CTG ACA TAC TTT CCA AT-3' [SEQ ID NO:9] (nucleotides 2817 to 2798 according to HBV Genebank Accession number M38454). The following primers were utilized for the sequencing of internal regions 5'-TGC ACG ATT CCT GCT CAA-3' [SEQ ID NO:10] (nucleotides 2345-2362 according to HBV Genebank Accession number M38454) and 5'-TTT CTC AAA GGT GGA GAC AG-3' [SEQ ID NO:11] (nucleotides 1790-1810 according to HBV Genebank Accession number M38454).

Example 15

Preparative Baculovirus Amplification and Purification

Baculoviruses were amplified by infecting suspension cultures of Sf21 cells in log phase at a multiplicity of infection (moi) of 0.5 pfu/cell. Infections were allowed to proceed until a majority of the cells in the flasks showed visible signs of infection (four to five days). Virions were concentrated from infected Sf21 medium by centrifugation at 80,000×g and purified through a 20-60% w/v sucrose gradient. Purified virus was titrated in quadruplicate in Sf21 cells by end-point dilution. An aliquot of each high titer stock was used for DNA extraction. The polymerase gene was amplified and sequenced to confirm the presence of the site-directed mutagenesis as in Example 14.

Example 16

Infection of HepG2 Cells with Recombinant HBV Expressing Baculovirus

HepG2 cells were seeded at approximately 20-40% confluency and then were grown for 16-24 hours before infection. On the day of infection, triplicate plates of cells were trypsinized, and viable cell number was determined with a hemocytometer using Trypan blue exclusion. Average cell counts were calculated and used to determine the volume of high-titer viral stock necessary to infect cells at the indicated moi. HepG2 cells were washed one time with serum-free MEM to remove traces of serum. Baculovirus was diluted into MEM without serum to achieve the appropriate moi using volumes of 1.0, 0.5, and 0.25 ml to infect 100-mm, 60 mm, and 35-mm dishes, respectively. Baculovirus was adsorbed to HepG2 cells for one hour at 37° C. with gentle rocking every 15 minutes to ensure that the inoculum was evenly distributed. The inoculum was then aspirated and HepG2 cells were washed two times with phosphate-buffered saline and refed MEM-FBS with or without various concentrations of agents.

Example 17

Detection of Intracellular Replicative Intermediates

HBV core particles were isolated from the cytoplasmic fraction of HepG2 cells lysed in 0.5% w/v NP-40. Cytoplasmic extracts were adjusted to 10 mmol/l McC12 and unprotected DNA was removed by an incubation to 500 g/ml Proteinase K for 1.5 hours at 37° C. HBV DNA in the samples were then extracted using commercial DNA extraction kits such as Qiagen (DNA extraction) or in-house methods using sequential phenol and chloroform extractions, and the nucleic acids were recovered by ethanol precipitation. Nucleic acids were resuspended in 50 µl/l TE (10 mmol/l Tris, 1 mmol/l ethylenediaminetetraacetic acid), normalized by OD260, and digested with 100 g/ml RNase (Boehringer Mannheim, Indianapolis, Ind.) for one hour at 37° C. before analysis by real-time PCR or electrophoresis and Southern blotting. After southern blot analysis a BioRad GS-670 imaging densitometer and the Molecular Analyst software (BioRad, Hecules Calif.) was used to analyze suitable exposures of Southern blots. Densitometry data was fitted to logistic dose response curves using the TableCurve 2D software package from Jandel Scientific. Logistic dose response equations were used to calculate $IC_{50}$ and $IC_{90}$ values and coefficients of variation.

Example 18

Real-Time PCR

For the real-time PCR based assay for HBV, HBV DNA was extracted from 200 µl of serum using the QIAamp DNA Mini Kit according to the manufacturer's instructions (QIAGEN GmbH, Hildens, Germany). Primers and a molecular beacon were designed for conserved nucleic acid sequences within the precore domain of the HBV genome to amplify and detect a 216-nucleotide product. Amplification was performed in a 50-µl reaction mixture containing 1.0 Taqman buffer A (Applied Biosystems, Foster City, Calif.), 3.0 mM MgCl, 0.4 µmol of each primer per µL, forward primer, PC1 (5'-GGGAGGAGATTAGGTTAA-3' [SEQ ID NO:12]) and reverse primer, PC2 (5'-GGCAAAAAC-GAGAGTAACTC-3' [SEQ ID NO:13]), 0.4 µmol of the HBV-specific molecular beacon per µL, (5'-FAM-CGCGTC-CTACTGTTCAAGCCTCCAAGCTGT GACGCG-DAB-CYL-3' [SEQ ID NO:14]; where FAM represents fluorophore 6-carboxyfluorescein and DABCYL, 4-dimethylaminophenylazobenzoic acid, a quenching chromophore) and 1.25 U of AmpliTaq Gold DNA polymerase (Perkin-Elmer). PCR was performed using the ABI PRISM 7700 spectrofluorometric thermocycler (Applied Biosystems). The PCR program consisted of an initial cycle (95° C. for 10 minutes) followed by 45 amplification cycles (94° C. for 15 secs, 50° C. for 30 secs, 72° C. for 30 secs). The instrument detected and recorded the fluorescence spectrum of each reaction tube during the annealing phase.

An external standard was constructed by ligation of a 1.3 kB wild-type HBV plasmid (genotype D) into the pBlueBac plasmid vector (Hershey Medical Center, Hershey, Pa.). Quantification of the DNA concentration of the plasmid was determined by spectrophotometry. Duplicates of serial 10-fold dilutions of the plasmid ranging from $10_8$ copies/ml to 100 copies/ml were included in each run in order to generate a standard curve. The copy number in each experimental reaction was determined by interpolation of the derived threshold cycle ($C_T$).

Example 19

ADV Treatments

ADV was resuspended in sterile water, aliquoted, and frozen at −20° C. to avoid repeated freezing and thawing of the drug. Medium containing ADV was prepared daily as needed using fresh aliquots of 3TC. In experiments in which ADV treatment was initiated after viral infection, HepG2 cells were exposed to the indicated concentration of ADV immediately after infection with HBV baculovirus. In experiments utilizing pretreatment with ADV, cells were fed medium containing ADV 16 hours prior to HBV baculovirus infection, HBV baculovirus infection was also carried out in medium containing ADV, and cells were refed fresh medium containing ADV immediately after completion of the infection and washing procedures.

Example 20

Antiviral Testing Performed with Wild-Type and HBV/Baculovirus Encoding rtA181T/N236T/N238D and rtN236T/N236D The in vitro antiviral drug cross-resistance testing of the HBV mutants is shown in Table 18. The laboratory reference strain of HBV (genotype D subtype ayw) containing the introduced D domain mutations demonstrated increased $IC_{50}$ values against ADV (Table 18). The rt N236T/N238D mutation was associated with a twenty-three fold increase in $IC_{50}$ against ADV. This was reduced to a five-fold increase when the rtA181T was also present and this triple HBV polymerase mutant was resistant to LMV.

TABLE 4

Clinical, virological and HBV sequencing data summary for Patient A while on open label ADV.

| Days post-ADV treatment | HBV DNA copies/ml (pg/ml) | ALT IU/L | Treatment protocol | Key polymerase mutations detected by sequencing[1] |
|---|---|---|---|---|
| −230 | 1.7 $10^6$ (61) | 67 U/L | pre-therapy | rtT/N128T/N<br>rtQ/H/R215Q/stop |
| 875 | | | ADV recommenced | |
| 904 | 1.55 × $10^6$ | | | |
| 932 | 2.97 × $10^6$ | | | |
| 959 | 1.76 × $10^6$ | | | |
| 983 | 1.64 × $10^6$ | 65 | end ADV | rtT128N<br>rtY135C |

[1]Nomenclature according to Stuyver et al., 2001, supra

TABLE 5

Summary of HBV mutations in patient A treated with ADV

| Sample name | Days post-ADV treatment | Genotype | Polymerase* | Surface |
|---|---|---|---|---|
| ILA1 | −230 | D | rtA/S21A/S<br>rtT/N128T/N**<br>rtQ/H/R215Q/stop | sP120P/T<br>sI208I/L |
| ILA2 | 904 | D | rtA/S21S<br>rtF122L<br>rtR126H<br>rtT/N128T/N<br>rtQ130P<br>rtN131D<br>rtQstop/215Q<br>rtH248N | sP/T120P<br>sT125M<br>sI/I208I/L |
| ILA3 | 932 | D | rtA/S21S<br>rtF122L<br>rtR126H<br>rtT/N128T/N<br>rtQ130P<br>rtN131D<br>rtQstop/215Q<br>rtH248N | sP/T120P<br>sT125M<br>sI/1208I/L |
| ILA4 | 983 | D | rtS21A<br>rtL122F<br>rtN124H<br>rtH126R<br>rtT128N<br>rtP130Q<br>rtD131N<br>rtY135C | sP120T<br>sM125T<br>sT127A |

*Nomenclature according to Stuyver et al., 2001, supra.
**Mutations in bold have not been detected in reference HBV genotypes, mutations not in bold are changes from the previous sample that are present in reference genotypes.

TABLE 6

Clinical, virological and HBV sequencing data summary for Patient B while on open label ADV.

| Days post-ADV treatment | HBV DN copies/ml (pg/ml) | ALT IU/L | Treatment protocol | Key polymerase mutations detected by sequencing[1] |
|---|---|---|---|---|
| −867(S0) | 183 | 298 | pre-therapy | rtN/S/T/I/V53D |
| | | | | rtV153G |
| | | | | rtQ/E215S |
| | | | | rtN248H |
| −8(S6) | 955 | 427 | pre-ADV on LMV | rtI/L80L |
| | | | | rtY126Q |
| | | | | rtL180M |
| | | | | rtS202G |
| | | | | rtI204V |
| 76(S8) | not detected | 150 | on ADV (20 mg) and LMV | rtN/S/T/I/V53D |
| | | | | rtY126Q |
| | | | | rtL180M |
| | | | | rtS202G |
| | | | | rtI204V |
| 637(S12) | not detected | 36 | on ADV (5 mg) and LMV | rtN/S/T/I/V53D |
| | | | | rtY126Q |
| | | | | rtL180M |
| | | | | rtS202G |
| | | | | rtI204V |
| 872(S15) | not detected | 67 | on ADV (5 mg) and LMV | rtN/S/T/I/V53D |
| | | | | rtY126Q |
| | | | | rtL180M |
| | | | | rtS202G |
| | | | | rtI204V |
| | | | | rtI235I/M |

[1]Nomenclature according to Stuyver et al., 2001, supra

TABLE 7

Summary of HBV mutations in Patient B treated with ADV

| Sample name | Days post-ADV treatment | Genotype | Polymerase* | Surface |
|---|---|---|---|---|
| S0 | −867 | D | rtN/S/T/I/V53D | sM/K/L133T |
| | | | rtV153G | sF134V |
| | | | rtQ/E215S | sS207R |
| | | | rtN248H | sL21V/L |
| S6 | −8 | D | rtI/L80L | sT118R |
| | | | rtY126Q | sM133T |
| | | | rtL180M | sF134V |
| | | | rtS202G | sI195M |
| | | | rtI204V | sS207R |
| S8 | 76 | D | rtN/S/T/I/V53D | sT118R |
| | | | rtY126Q | sM133T |
| | | | rtL180M | sF134V |
| | | | rtS202G | sI195M |
| | | | rtI204V | sS207R |
| S12 | 637 | D | rtN/S/T/I/V53D | sT118R |
| | | | rtY126Q | sM133T |
| | | | rtL180M | sF134V |
| | | | rtS202G | sI195M |
| | | | I204V | sS207R |
| S15 | 872 | D | rtN/S/T/I/V53D | sT118R |
| | | | rtY126Q | sM133T |
| | | | rtL180M | sF134V |
| | | | rtS202G | sI195M |
| | | | rtI204V | sS207R |
| | | | rtI235I/M | sY225Y/C |

*Nomenclature according to Stuyver et al., 2001, supra
**Mutations in bold have not been detected in reference HBV genotypes, mutations not in bold are changes from the previous sample that are present in reference genotypes.

TABLE 8

Clinical, virological and HBV sequencing data summary for Patient C while on open label ADV.

| Days post-ADV treatment | HBV DNA copies/ml (pg/ml) | ALT IU/L | Treatment protocol | Key polymerase mutations detected by sequencing[1] |
|---|---|---|---|---|
| −26 | $2 \times 10^7$ | | pre-therapy | rtN53D |
| | | | | rtS116P |
| | | | | rtD/N/S134V |
| | | | | rtN238D |
| 0 | | 240 | ADV commenced clinical trial | |
| 29 | | 160 | | |
| 630 | | 407 | | |
| 668 | | | Open label ADV | |
| 701 | $1.5 \times 10^7$ | 226 | | |
| 730 | $3.7 \times 10^6$ | 361 | | rtN53D |
| | | | | rtS116P |
| | | | | rtF151S/T |
| | | | | rtA181T |
| | | | | rtN236T |
| | | | | rtN238D |
| 738 | | 517 | | |
| 739 | | | end ADV, start LMV | |

[1]Nomenclature according to Stuyver et al., 2001, supra

TABLE 9

Summary of HBV mutations in Patient C treated with ADV

| Sample name | Days post-ADV treatment | Genotype | Polymerase* | Surface |
|---|---|---|---|---|
| DRJ1299 | −26 | D | rtN53D** | T126S |
| | | | rtY54H | S204G |
| | | | rtS57P | L209V |
| | | | rtL91I | S210R |
| | | | rtS116P | |
| | | | rtF122L | |
| | | | rtY124H | |
| | | | rtD/N/S134V | |
| | | | rtK212R | |
| | | | rtL217R | |
| | | | rtS219A | |
| | | | rtN238D | |
| DRJ1 | 730 | D | rtN53D | sS126T |
| | | | rtY54H | sM133L/M |
| | | | rtS57P | sS143S/T |
| | | | rtL91I | sD144A |
| | | | rtS116P | sG145A |
| | | | rtF122L | sW172Stop |
| | | | rtY124H | |
| | | | rtV134D | |
| | | | rtY141Y/F | |
| | | | rtL145M | |
| | | | rtF151T/F | |
| | | | rtA181T | |
| | | | rtK212R | |
| | | | rtL217R | |
| | | | rtS219A | |
| | | | rtN236T | |
| | | | rtN238D | |

*Nomenclature according to Stuyver et al., 2001, supra.
**Mutations in bold have not been detected in reference HBV genotypes, mutations not in bold are changes from the previous sample that are present in reference genotypes.

TABLE 10

Summary of HBV mutations in Patient D treated with ADV

| Sample Name | Genotype | Polymerase* | Surface |
|---|---|---|---|
| 02575908 | D | rtS78T | sN40S |
|  |  | rtV84M | sC69stop |
|  |  | rtY126C | sM75I |
|  |  | rtV191I | sL88P |
|  |  | rtM204I | sT118A |
|  |  | rtV214A | sW182STOP |
|  |  |  | sW196L |
|  |  |  | sY206H |
|  |  |  | sY225F |

*Nomenclature according to Stuyver et al., 2001, supra.
**Mutations in bold have not been detected in reference HBV genotypes, mutations not in bold are changes from the previous sample that are present in reference genotypes.

TABLE 11

Summary of HBV mutations in Patient E treated with ADV

| Sample Name | Genotype | Polymerase* | Surface |
|---|---|---|---|
| 8123/02 | A | rtH90D | sI81M |
|  |  | rtL/F108L | sY/S100Y |
|  |  | 6 nt insertion/duplication after codon rt131(aaQ&N) | 6 nt insertion/duplication after codon s122 (aaT & K) |
|  |  |  | sP214Q |

*Nomenclature according to Stuyver et al., 2001, supra.
**Mutations in bold have not been detected in reference HBV genotypes, mutations not in bold are changes from the previous sample that are present in reference genotypes.

TABLE 12

Codons where mutations occur following exposure to nucleoside or nucleotide analogs

| Region/Domain | Original amino acid in reverse transcriptase (rt) and codon position | Nucleotide | | | |
|---|---|---|---|---|---|
| prior to F | K32 | AAG | AAA | | |
|  | N33 | AAT | | | |
|  | P34 | CCT | | | |
|  | H35 | CAC | | | |
|  | T37 | ACC | | | |

TABLE 12-continued

Codons where mutations occur following exposure to nucleoside or nucleotide analogs

| Region/Domain | Original amino acid in reverse transcriptase (rt) and codon position | Nucleotide | | | |
|---|---|---|---|---|---|
| F TO A | P59 | CCA | | | |
|  | K60 | AAA | | | |
|  | F61 | TTC | | | |
|  | A62 | GCA | | | |
|  | V63 | GTC | | | |
| A | D83 | GAT | | | |
|  | V84 | GTG | | | |
|  | S85 | TCT | | | |
|  | A86 | GCG | | | |
|  | Y89 | TAT | | | |
|  | H90 | CAT | | | |
|  | I/L91 | ATT | CTT | | |
| B | P177 | CCG | | | |
|  | F178 | TTT | | | |
|  | L179 | CTC | | | |
|  | L180 | CTG | | | |
|  | A181 | TTG | | | |
|  | Q182 | CAG | | | |
|  | F183 | TTT | | | |
|  | T184 | ACT | | | |
| C | Y203 | TAT | | | |
|  | M204 | ATG | | | |
| D | L235 | TTG | TTA | | |
|  | N236 | AAC | AAT | | |
|  | T237 | ACT | ACC | | |
|  | P237 | CCT | CCC | | |
|  | N238 | AAT | AAC | | |
|  | H238 | CAC | | | |
|  | A238 | GCT | | | |
|  | S238 | TCT | | | |
|  | Q238 | CAG | | | |
|  | K239 | AAA | AAG | | |
| E | L247 | CTT | TTA | CTA | CTC | CTG |
|  | N248 | AAC | AAT | | |
|  | H248 | CAT | CAC | | |
|  | F249 | TTC | TTT | | |
|  | M250 | ATG | | | |
|  | G251 | GGT | GGA | GGC | GGG |
|  | V251 | GTC | | | |

TABLE 13

Target amino acid sites in rt with codons and mutations leading to amino acid changes.

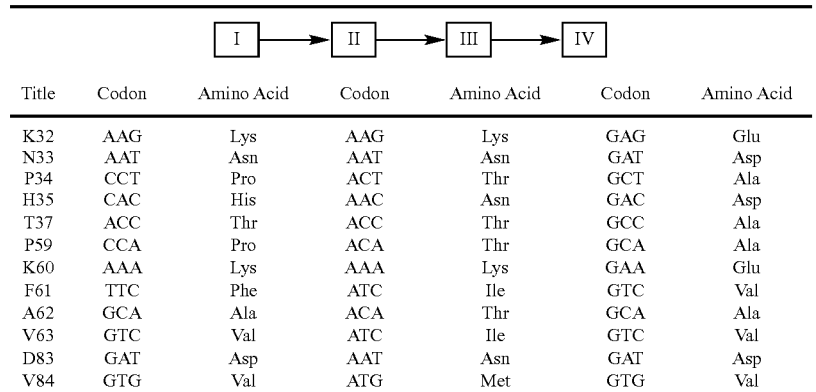

| Title | Codon | Amino Acid | Codon | Amino Acid | Codon | Amino Acid |
|---|---|---|---|---|---|---|
| K32 | AAG | Lys | AAG | Lys | GAG | Glu |
| N33 | AAT | Asn | AAT | Asn | GAT | Asp |
| P34 | CCT | Pro | ACT | Thr | GCT | Ala |
| H35 | CAC | His | AAC | Asn | GAC | Asp |
| T37 | ACC | Thr | ACC | Thr | GCC | Ala |
| P59 | CCA | Pro | ACA | Thr | GCA | Ala |
| K60 | AAA | Lys | AAA | Lys | GAA | Glu |
| F61 | TTC | Phe | ATC | Ile | GTC | Val |
| A62 | GCA | Ala | ACA | Thr | GCA | Ala |
| V63 | GTC | Val | ATC | Ile | GTC | Val |
| D83 | GAT | Asp | AAT | Asn | GAT | Asp |
| V84 | GTG | Val | ATG | Met | GTG | Val |

TABLE 13-continued

Target amino acid sites in rt with codons and mutations leading to amino acid changes.

| | | | | | | |
|---|---|---|---|---|---|---|
| S85 | TCT | Ser | ACT | Thr | GCT | Ala |
| A86 | GCG | Ala | ACG | Thr | GCG | Ala |
| Y89 | TAT | Tyr | AAT | Asn | GAT | Asp |
| H90 | CAT | His | AAT | Asn | GAT | Asp |
| I/L91 | ATT | Ile | ATT | Ile | GTT | Val |
| P177 | CCG | Pro | ACG | Thr | GCG | Ala |
| F178 | TTT | Phe | ATT | Ile | GTT | Val |
| L179 | CTC | Leu | ATC | Ile | GTC | Val |
| L180 | CTG | Leu | ATG | Met | GTG | Val |
| A181 | TTG | Leu | ATG | Met | GTG | Val |
| Q183 | CAG | Gln | AAG | Lys | GAG | Glu |
| F183 | TTT | Phe | ATT | Ile | GTT | Val |
| T184 | ACT | Thr | ACT | Thr | GCT | Ala |
| Y203 | TAT | Tyr | AAT | Asn | GAT | Asp |
| M204 | ATG | Met | ATG | Met | GTG | Val |
| L235 | TTG | Leu | ATG | Met | GTG | Val |
| N236 | AAC | Asn | AAC | Asn | GAC | Asp |
| T237 | ACT | Thr | ACT | Thr | GCT | Ala |
| P237 | CCT | Pro | ACT | Thr | GCT | Ala |
| N238 | AAT | Asn | AAT | Asn | GAT | Asp |
| H238 | GAG | His | AAC | Asn | GAG | Asp |
| A238 | GCT | Ala | ACT | Thr | GCT | Ala |
| S239 | TCT | Ser | ACT | Thr | GCT | Ala |
| Q238 | CAG | Gln | AAG | Lys | GAG | Glu |
| K239 | AAA | Lys | AAA | Lys | GAA | Glu |
| L247 | CTT | Leu | ATT | Ile | GTT | Val |
| N248 | AAC | Asn | AAC | Asn | GAC | Asp |
| H248 | CAT | His | AAT | Asn | GAT | Asp |
| F249 | TTC | Phe | ATC | Ile | GTC | Val |
| M250 | ATG | Met | ATG | Met | GTG | Val |
| G251 | GGT | Gly | AGT | Ser | GGT | Gly |
| V251 | GTC | Val | ATC | Ile | GTC | Val |

(II)

| | Codon | Amino Acid | Codon | Amino Acid | Codon | Amino Acid |
|---|---|---|---|---|---|---|
| K32 | CAG | Gln | TAG | Stop | AAG | Lys |
| N33 | CAT | His | TAT | Tyr | AAT | Asn |
| P34 | CCT | Pro | TCT | Ser | CAT | His |
| H35 | CAC | His | TAC | Tyr | CAC | His |
| T37 | CCC | Pro | TCC | Ser | AAC | Asn |
| P59 | CCA | Pro | TCA | Ser | CAA | Gln |
| K60 | CAA | Gln | TAA | Stop | AAA | Lys |
| F61 | CTC | Leu | TTC | Phe | TAC | Tyr |
| A62 | CCA | Pro | TCA | Ser | GAA | Glu |
| V63 | CTC | Leu | TTC | Phe | GAC | Asp |
| D83 | CAT | His | TAT | Tyr | GAT | Asp |
| V84 | CTG | Leu | TTG | Leu | GAG | Glu |
| S85 | CCT | Pro | TCT | Ser | TAT | Tyr |
| A86 | CCG | Pro | TCG | Ser | GAG | Glu |
| Y89 | CAT | His | TAT | Tyr | TAT | Try |
| H90 | CAT | His | TAT | Tyr | CAT | His |
| I/L91 | CTT | Leu | TTT | Phe | AAT | Asn |
| P177 | CCG | Pro | TCG | Ser | CAG | Gln |
| F178 | CTT | Leu | TTT | Phe | TAT | Tyr |
| L179 | CTC | Leu | TTC | Phe | CAC | His |
| L180 | CTG | Leu | TTG | Leu | CAG | Gln |
| A181 | CTG | Leu | TTG | Leu | TAG | Stop |
| Q183 | CAG | Gln | TAG | Stop | CAG | Gln |
| F183 | CTT | Leu | TTT | Phe | TAT | Tyr |
| T184 | CCT | Pro | TCT | Ser | AAT | Asn |
| Y203 | CAT | His | TAT | Try | TAT | Try |
| M204 | CTG | Leu | TTG | Leu | AAG | Lys |
| L235 | CTG | Leu | TTG | Leu | TAG | Stop |
| N236 | CAC | His | TAC | Tyr | AAC | Asn |
| T237 | CCT | Pro | TCT | Ser | AAT | Asn |
| P237 | CCT | Pro | TCT | Ser | CAT | His |
| N238 | CAT | His | TAT | Tyr | AAT | Asn |
| H238 | CAC | His | TAC | Tyr | CAC | His |
| A238 | CCT | Pro | TCT | Ser | GAT | Asp |
| S239 | CCT | Pro | TCT | Ser | TAT | Tyr |
| Q238 | CAG | Gln | TAG | Stop | CAG | Gln |
| K239 | CAA | Gln | TAA | Stop | AAA | Lys |
| L247 | CTT | Leu | TTT | Phe | CAT | His |
| N248 | CAC | His | TAC | Tyr | AAC | Asn |
| H248 | CAT | His | TAT | Tyr | CAT | His |

TABLE 13-continued

Target amino acid sites in rt with codons and mutations leading to amino acid changes.

| | | | | | | | |
|---|---|---|---|---|---|---|---|
| F249 | CTC | Leu | TTC | Phe | TAC | Tyr | |
| M250 | CTG | Leu | TTG | Leu | AAG | Lys | |
| G251 | CGT | Arg | TGT | Cys | GAT | Asp | |
| V251 | CTC | Leu | TTC | Phe | GAC | Asp | |

(III)

| | Codon | Amino Acid | Codon | Amino Acid | Codon | Amino Acid |
|---|---|---|---|---|---|---|
| K32 | AGG | Arg | ACG | Thr | ATG | Met |
| N33 | AGT | Ser | ACT | Thr | ATT | Ile |
| P34 | CGT | Arg | CCT | Pro | CTT | Leu |
| H35 | CGC | Arg | CCC | Pro | CTC | Leu |
| T37 | AGC | Ser | ACC | Thr | ATC | Ile |
| P59 | CGA | Arg | CCA | Pro | CTA | Leu |
| K60 | AGA | Arg | ACA | Thr | ATA | Ile |
| F61 | TGC | Cys | TCC | Ser | TTC | Phe |
| A62 | GGA | Gly | GCA | Ala | GTA | Val |
| V63 | GGC | Gly | GCC | Ala | GTC | Val |
| D83 | GGT | Gly | GCT | Ala | GTT | Val |
| V84 | GGG | Gly | GCG | Ala | GTG | Val |
| S85 | TGT | Cys | TCT | Ser | TTT | Phe |
| A86 | GGG | Gly | GCG | Ala | GTG | Val |
| Y89 | TGT | Cys | TCT | Ser | TTT | Phe |
| H90 | CGT | Arg | CCT | Pro | CTT | Leu |
| I/L91 | AGT | Ser | ACT | Thr | ATT | Ile |
| P177 | CGG | Arg | CCG | Pro | CTG | Leu |
| F178 | TGT | Cys | TCT | Ser | TTT | Phe |
| L179 | CGC | Arg | CCC | Pro | CTC | Leu |
| L180 | CGG | Arg | CCG | Pro | CTG | Leu |
| A181 | TGG | Trp | TCG | Ser | TTG | Leu |
| Q183 | CGG | Arg | CCG | Pro | CTG | Leu |
| F183 | TGT | Cys | TCT | Ser | TTT | Phe |
| T184 | AGT | Ser | ACT | Thr | ATT | Ile |
| Y203 | TGT | Cys | TCT | Ser | TTT | Phe |
| M204 | AGG | Arg | ACG | Thr | ATG | Met |
| L235 | TGG | Trp | TCG | Ser | TTG | Leu |
| N236 | AGC | Ser | ACC | Thr | ATC | Ile |
| T237 | AGT | Ser | ACT | Thr | ATT | Ile |
| P237 | CGT | Arg | CCT | Pro | CTT | Leu |
| N238 | AGT | Ser | ACT | Thr | ATT | Ile |
| H238 | CGC | Arg | CCC | Pro | CTC | Leu |
| A238 | GGT | Gly | GCT | Ala | GTT | Val |
| S239 | TGT | Cys | TCT | Ser | TTT | Phe |
| Q238 | CGG | Arg | CCG | Pro | CTG | Leu |
| K239 | AGA | Arg | ACA | Thr | ATA | Ile |
| L247 | CGT | Arg | CCT | Pro | CTT | Leu |
| N248 | AGC | Ser | ACC | Thr | ATC | Ile |
| H248 | CGT | Arg | CCT | Pro | CTT | Leu |
| F249 | TGC | Cys | TCC | Ser | TTC | Phe |
| M250 | AGG | Arg | ACG | Thr | ATG | Met |
| G251 | GGT | Gly | GCT | Ala | GTT | Val |
| V251 | GGC | Gly | GCC | Ala | GTC | Val |

(IV)

| | Codon | Amino Acid | Codon | Amino Acid | Codon | Amino Acid | Codon | Amino Acid |
|---|---|---|---|---|---|---|---|---|
| K32 | AAA | Lys | AAG | Lys | AAC | Asn | AAT | Asn |
| N33 | AAA | Lys | AAG | Lys | AAC | Asn | AAT | Asn |
| P34 | CCA | Pro | CCG | Pro | CCC | Pro | CCT | Pro |
| H35 | CAA | Gln | CAG | Gln | CAC | His | CAT | His |
| T37 | ACA | Thr | ACG | Thr | ACC | Thr | ACT | Thr |
| P59 | CCA | Pro | CCG | Pro | CCC | Pro | CCT | Pro |
| K60 | AAA | Lys | AAG | Lys | AAC | Asn | AAT | Asn |
| F61 | TTA | Leu | TTG | Leu | TTC | Phe | TTT | Phe |
| A62 | GCA | Ala | GCG | Ala | GCC | Ala | GCT | Ala |
| V63 | GTA | Val | GTG | Val | GTC | Val | GTT | Val |
| D83 | GAA | Glu | GAG | Glu | GAC | Asp | GAT | Asp |
| V84 | GTA | Val | GTG | Val | GTC | Val | GTT | Val |
| S85 | TCA | Ser | TCG | Ser | TCC | Ser | TCT | Ser |
| A86 | GCA | Ala | GCG | Ala | GCC | Ala | GCT | Ala |
| Y89 | TAA | Stop | TAG | Stop | TAC | Tyr | TAT | Tyr |
| H90 | CAA | Gln | CAG | Gln | CAC | His | CAT | His |
| I/L91 | ATA | Ile | ATG | Met | ATC | Ile | ATT | Ile |
| P177 | CCA | Pro | CCG | Pro | CCC | Pro | CCT | Pro |
| F178 | TTA | Leu | TTG | Leu | TTC | Phe | TTT | Phe |

TABLE 13-continued

Target amino acid sites in rt with codons and mutations leading to amino acid changes.

| | | | | | | | | |
|---|---|---|---|---|---|---|---|---|
| L179 | CTA | Leu | CTG | Leu | CTC | Leu | CTT | Leu |
| L180 | CTA | Leu | CTG | Leu | CTC | Leu | CTT | Leu |
| A181 | TTA | Leu | TTG | Leu | TTC | Phe | TTT | Phe |
| Q183 | CAA | Gln | CAG | Gln | CAC | His | CAT | His |
| F183 | TTA | Leu | TTG | Leu | TTC | Phe | TTT | Phe |
| T184 | ACA | Thr | ACG | Thr | ACC | Thr | ACT | Thr |
| Y203 | TAA | Stop | TAG | Stop | TAC | Tyr | TAT | Tyr |
| M204 | ATA | Ile | ATG | Met | ATC | Ile | ATT | Ile |
| L235 | TTA | Leu | TTG | Leu | TTC | Phe | TTT | Phe |
| N236 | AAA | Lys | AAG | Lys | AAC | Asn | AAT | Asn |
| T237 | ACA | Thr | ACG | Thr | ACC | Thr | ACT | Thr |
| P237 | CCA | Pro | CCG | Pro | CCC | Pro | CCT | Pro |
| N238 | AAA | Lys | AAG | Lys | AAC | Asn | AAT | Asn |
| H238 | CAA | Gln | CAG | Gln | CAC | His | CAT | His |
| A238 | GCA | Ala | GCG | Ala | GCC | Ala | GCT | Ala |
| S239 | TCA | Ser | TCG | Ser | TCC | Ser | TCT | Ser |
| Q238 | CAA | Gln | CAG | Gln | CAC | His | CAT | His |
| K239 | AAA | Lys | AAG | Lys | AAC | Asn | AAT | Asn |
| L247 | CTA | Leu | CTG | Leu | CTC | Leu | CTT | Leu |
| N248 | AAA | Lys | AAG | Lys | AAC | Asn | AAT | Asn |
| H248 | CAA | Gln | CAG | Gln | CAC | His | CAT | His |
| F249 | TTA | Leu | TTG | Leu | TTC | Phe | TTT | Phe |
| M250 | ATA | Ile | ATG | Met | ATC | Ile | ATT | Ile |
| G251 | GGA | Gly | GGG | Gly | GGC | Gly | GGT | Gly |
| V251 | GTA | Val | GTG | Val | GTC | Val | GTT | Val |

TABLE 14

Amino acid mutations at target sites in rt

| Target | Mutation |
|---|---|
| K32 | M/F/P/S/T/W/Y/V/A/R/N/D/C/Q/E/G/H/I/L |
| N33 | D/C/Q/E/G/H/I/L/K/M/F/P/S/T/W/Y/V/A/R |
| P34 | S/T/W/Y/V/A/R/N/D/C/Q/E/G/H/I/L/K/M/F |
| H35 | I/L/K/M/F/P/S/T/W/Y/V/A/R/N/D/C/Q/E/G |
| T37 | W/Y/V/A/R/N/D/C/Q/E/G/H/I/L/K/M/F/P/S |
| P59 | S/T/W/Y/V/A/R/N/D/C/Q/E/G/H/I/L/K/M/F |
| K60 | M/F/P/S/T/W/Y/V/A/R/N/D/C/Q/E/G/H/I/L |
| F61 | P/S/T/W/Y/V/A/R/N/D/C/Q/E/G/H/I/L/K/M |
| A62 | R/N/D/C/Q/E/G/H/I/L/K/M/F/P/S/T/W/Y/V |
| V63 | A/R/N/D/C/Q/E/G/H/I/L/K/M/F/P/S/T/W/Y |
| D83 | C/Q/E/G/H/I/L/K/M/F/P/S/T/W/Y/V/A/R/N |
| V84 | A/R/N/D/C/Q/E/G/H/I/L/K/M/F/P/S/T/W/Y |
| S85 | T/W/Y/V/A/R/N/D/C/Q/E/G/H/I/L/K/M/F/P |
| A86 | R/N/D/C/Q/E/G/H/I/L/K/M/F/P/S/T/W/Y/V |
| Y89 | V/A/R/N/D/C/Q/E/G/H/I/L/K/M/F/P/S/T/W |
| H90 | I/L/K/M/F/P/S/T/W/Y/V/A/R/N/D/C/Q/E/G |
| I/L91 | K/M/F/P/S/T/W/Y/V/A/R/N/D/C/Q/E/G/H |
| P177 | S/T/W/Y/V/A/R/N/D/C/Q/E/G/H/I/L/K/M/F |
| F178 | P/S/T/W/Y/V/A/R/N/D/C/Q/E/G/H/I/L/K/M |
| L179 | K/M/F/P/S/T/W/Y/V/A/R/N/D/C/Q/E/G/H/I |
| L180 | K/M/F/P/S/T/W/Y/V/A/R/N/D/C/Q/E/G/H/I |
| A181 | R/N/D/C/Q/E/G/H/I/L/K/M/F/P/S/T/W/Y/V |
| Q183 | E/G/H/I/L/K/M/F/P/S/T/W/Y/V/A/R/N/D/C |
| F183 | P/S/T/W/Y/V/A/R/N/D/C/Q/E/G/H/I/L/K/M |
| T184 | W/Y/V/A/R/N/D/C/Q/E/G/H/I/L/K/M/F/P/S |
| Y203 | V/A/R/N/D/C/Q/E/G/H/I/L/K/M/F/P/S/T/W |
| M204 | F/P/S/T/W/Y/V/A/R/N/D/C/Q/E/G/H/I/L/K |
| L235 | K/M/F/P/S/T/W/Y/V/A/R/N/D/C/Q/E/G/H/I |
| N236 | D/C/Q/E/G/H/I/L/K/M/F/P/S/T/W/Y/V/A/R |
| T237 | W/Y/V/A/R/N/D/C/Q/E/G/H/I/L/K/M/F/P/S |
| P237 | S/T/W/Y/V/A/R/N/D/C/Q/E/G/H/I/L/K/M/F |
| N238 | D/C/Q/E/G/H/I/L/K/M/F/P/S/T/W/Y/V/A/R |
| H238 | I/L/K/M/F/P/S/T/W/Y/V/A/R/N/D/C/Q/E/G |
| A238 | R/N/D/C/Q/E/G/H/I/L/K/M/F/P/S/T/W/Y/V |
| S239 | T/W/Y/V/A/R/N/D/C/Q/E/G/H/I/L/K/M/F/P |
| Q238 | E/G/H/I/L/K/M/F/P/S/T/W/Y/V/A/R/N/D/C |
| K239 | M/F/P/S/T/W/Y/V/A/R/N/D/C/Q/E/G/H/I/L |
| L247 | K/M/F/P/S/T/W/Y/V/A/R/N/D/C/Q/E/G/H/I |
| N248 | D/C/Q/E/G/H/I/L/K/M/F/P/S/T/W/Y/V/A/R |
| H248 | I/L/K/M/F/P/S/T/W/Y/V/A/R/N/D/C/Q/E/G |
| F249 | P/S/T/W/Y/V/A/R/N/D/C/Q/E/G/H/I/L/K/M |

TABLE 14-continued

Amino acid mutations at target sites in rt

| Target | Mutation |
|---|---|
| M250 | F/P/S/T/W/Y/V/A/R/N/D/C/Q/E/G/H/I/L/K |
| G251 | H/I/L/K/M/F/P/S/T/W/Y/V/A/R/N/D/C/Q/E |
| V251 | A/R/N/D/C/Q/E/G/H/I/L/K/M/F/P/S/T/W/Y |

TABLE 15

Summary of HBV mutations in Patient F treated with ADV

| Sample Name | Genotype | Polymerase* | Surface |
|---|---|---|---|
| CAP 01564808 | A | rtL157L/M<br>rtA181V<br>rtV207I<br>rtN236T | sF83S<br>sL173F<br>sW199L |

*Nomenclature according to Stuyver et al., 2001, supra.

**Mutations in bold have not been detected in reference HBV genotypes, mutations not in bold are changes from the previous sample that are present in reference genotypes.

TABLE 16

Summary of HBV mutations in Patient G treated with ADV

| Sample Name | Genotype | Polymerase* | Surface |
|---|---|---|---|
| KAN 02510355 | C | rtL80V<br>rtP109S<br>rtI163V<br>rtM204I<br>rtL229M<br>rtN/H/A/S/Q238K | sI126T<br>sK160R<br>sS174N<br>sA184V<br>sW196L<br>sS210N<br>sF/C220L<br>sY221C |

*Nomenclature according to Stuyver et al., 2001, supra.

**Mutations in bold have not been detected in reference HBV genotypes, mutations not in bold are changes from the previous sample that are present in reference genotypes.

TABLE 17

Summary of HBV mutations in Patient H treated with ADV

| Sample Name | Genotype | Polymerase* | Surface |
|---|---|---|---|
| LAV0303 | D | rtS78S/T | sC69Stop/C |
|  |  | rtN118N/S | sC76Y |
|  |  | rtN139N/K | sI110V/I |
|  |  | rtV142E | sY134N |
|  |  | rtA181A/T | sW172Stop/W |
|  |  | rtI204M | sW196Stop |
|  |  | rtQ/P/S/Stop215Q | sS207R |
|  |  | rtE218K/E |  |
|  |  | rtN238N/H |  |

*Nomenclature according to Stuyver et al., 2001, supra.
**Mutations in bold have not been detected in reference HBV genotypes, mutations not in bold are changes from the previous sample that are present in reference genotypes.

TABLE 18

In vitro drug susceptibility of the HBV reference laboratory strain and patient-derived HBV isolate

| | In vitro Susceptibility $IC_{50}$ (fold change from wild-type) | | |
|---|---|---|---|
| | Real-time PCR | Southern Blot | |
| Mutation | Adefovir | Adefovir | Lamivudine |
| Wild-type (pPC) | 1 | 1 | 1 |
| rt N236T/N238D | 23 | NA[1] | NA[1] |
| rt A181T/N236T/N238D | 5.1 | 7.3 | >100 |
| rt L180M/M204V[2] | NT[5] | 0.9 | >2500 |

[1]NA, not analyzed.
[2]Data from Delaney et al., 2001, supra

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Allen et al., *Hepatology* 27(6): 1670-1677, 1998
Aye et al., *J. Hepatol.* 26: 1148-1153, 1997
Bartholomeusz et al., *Intervirology* 40(5-6): 337-342 1997
Benhamou et al., *Lancet* 358: 718-723, 2001
Benzaria et al., *J Med. Chem.* 39: 4958-4965, 1996
Boyd et al, *Antiviral Chem Chemother.* 32: 358-363, 1987
Calio et al., *Antiviral Res.* 23: 77-89, 1994
Das et al., *J. Virol.* 75(10): 4771-4779, 2001
Delaney et al., *Antimicrob Agents Chemother* 45(6): 1705-1013, 2001
Dienstag et al., *New England J Med* 333: 1657-1661, 1995
Frick et al., *Antimicrob. Agents Chemother.* 377: 2285-2292, 1993
Gaillard et al., *Antimicrob Agents Chemother.* 46(4): 1005-1013, 2002
Gilson et al., *J Viral Hepat* 6: 387-395, 1999
Heathcote et al., *Hepatology* 28: A620, 1998
Hendricks et al., *Am J Clin Pathol* 104: 537-46, 1995
Kruger et al., *Hepatology* 22: 219A, 1994
Main et al., *J Viral Hepatitis* 3: 211-215, 1996
Norder et al., (*J. Gen. Virol.* 74: 341-1348, 1993
Perrillo et al., *Hepatology* 32: 129-134, 2000
Peters et al., *Transplantation* 68: 1912-1914, 1999
Price et al., *Proc. Natl. Acad. Sci. USA* 86(21): 8541-8544, 1989
Ren and Nassal, *J. Virol.* 75(3): 1104-1116, 2001
Severini et al., *Antimicrobial Agents Chemother.* 39: 430-435, 1995
Stuyver et al., *Hepatology* 33: 751-757, 2001
Summers and Mason, *Cell* 29: 403-415, 1982
Suo et al., *J Biol. Chem.* 273(42): 27250-27258. 1998
Vere Hodge, *Antiviral Chem Chemother* 4: 67-84, 1993
Xiong et al., *Hepatology.* 28(6): 1669-73, 1998
Ying et al., *J. Viral Hepat.* 7(2): 161-165, 2000
Ying et al., *J. Viral Hepat.* 7(1): 79-83, 2000
Ying et al., *Viral Hepat.* 7(2): 161-165, 2000

The invention claimed is:

1. A method for determining the potential for a hepatitis B virus variant to exhibit reduced sensitivity to a substituted acyclic nucleoside phosphonate selected from the group consisting of adefovir and tenofovir, comprising:
   (a) isolating DNA or corresponding mRNA from said hepatitis B virus; and
   (b) screening for a mutation in the nucleotide sequence encoding a hepatitis B virus DNA polymerase resulting in an amino acid substitution in the reverse transcriptase (rt) of said DNA polymerase, wherein said mutation is rtA181V, and wherein the presence of said mutation is an indication of resistance to said substituted acyclic nucleoside phosphonate adefovir or tenofovir.

2. The method of claim 1, wherein said substituted acyclic nucleoside phosphonate is adefovir.

3. The method of claim 1, further comprising screening for a mutation of rtN236T in said hepatitis B virus DNA polymerase, wherein the presence of said rtN236T mutation further indicates resistance to adefovir or tenofovir.

* * * * *

SEQUENCE LISTING

```
<160> NUMBER OF SEQ ID NOS: 59

<210> SEQ ID NO 1
<211> LENGTH: 76
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa = L or R or I
<220> FEATURE:
<221> NAME/KEY: MISC_FEATURE
<222> LOCATION: (3)..(3)
<223> OTHER INFORMATION: Xaa = E or D
<220> FEATURE:
<221> NAME/KEY: MISC_FEATURE
<222> LOCATION: (9)..(9)
<223> OTHER INFORMATION: Xaa = T or D or A or N or Y
<220> FEATURE:
<221> NAME/KEY: MISC_FEATURE
<222> LOCATION: (10)..(10)
<223> OTHER INFORMATION: Xaa = E or D
```

```
<220> FEATURE:
<221> NAME/KEY: MISC_FEATURE
<222> LOCATION: (13)..(13)
<223> OTHER INFORMATION: Xaa = E or K or Q
<220> FEATURE:
<221> NAME/KEY: MISC_FEATURE
<222> LOCATION: (15)..(15)
<223> OTHER INFORMATION: Xaa = H or R or N
<220> FEATURE:
<221> NAME/KEY: MISC_FEATURE
<222> LOCATION: (18)..(18)
<223> OTHER INFORMATION: Xaa = I or T
<220> FEATURE:
<221> NAME/KEY: MISC_FEATURE
<222> LOCATION: (23)..(23)
<223> OTHER INFORMATION: Xaa = A or S
<220> FEATURE:
<221> NAME/KEY: MISC_FEATURE
<222> LOCATION: (26)..(26)
<223> OTHER INFORMATION: Xaa = T or R
<220> FEATURE:
<221> NAME/KEY: MISC_FEATURE
<222> LOCATION: (40)..(40)
<223> OTHER INFORMATION: Xaa = A or T or S
<220> FEATURE:
<221> NAME/KEY: MISC_FEATURE
<222> LOCATION: (43)..(43)
<223> OTHER INFORMATION: Xaa = R or T
<220> FEATURE:
<221> NAME/KEY: MISC_FEATURE
<222> LOCATION: (45)..(45)
<223> OTHER INFORMATION: Xaa = V or G
<220> FEATURE:
<221> NAME/KEY: MISC_FEATURE
<222> LOCATION: (55)..(55)
<223> OTHER INFORMATION: Xaa = S or I or T or N or V
<220> FEATURE:
<221> NAME/KEY: MISC_FEATURE
<222> LOCATION: (56)..(56)
<223> OTHER INFORMATION: Xaa = T or S or H or Y
<220> FEATURE:
<221> NAME/KEY: MISC_FEATURE
<222> LOCATION: (57)..(57)
<223> OTHER INFORMATION: Xaa = R or H or K or Q
<220> FEATURE:
<221> NAME/KEY: MISC_FEATURE
<222> LOCATION: (69)..(69)
<223> OTHER INFORMATION: Xaa = Q or P

<400> SEQUENCE: 1

Leu Xaa Xaa Asp Trp Gly Pro Cys Xaa Xaa His Gly Xaa His Xaa Ile
1               5                   10                  15

Arg Xaa Pro Arg Thr Pro Xaa Arg Val Xaa Gly Gly Val Phe Leu Val
            20                  25                  30

Asp Lys Asn Pro His Asn Thr Xaa Glu Ser Xaa Leu Xaa Val Asp Phe
        35                  40                  45

Ser Gln Phe Ser Arg Gly Xaa Xaa Xaa Val Ser Trp Pro Lys Phe Ala
    50                  55                  60

Val Pro Asn Leu Xaa Ser Leu Thr Asn Leu Leu Ser
65                  70                  75

<210> SEQ ID NO 2
<211> LENGTH: 181
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa = N or D
<220> FEATURE:
<221> NAME/KEY: MISC_FEATURE
```

```
<222> LOCATION: (17)..(17)
<223> OTHER INFORMATION: Xaa = I or P
<220> FEATURE:
<221> NAME/KEY: MISC_FEATURE
<222> LOCATION: (29)..(29)
<223> OTHER INFORMATION: Xaa = I or V
<220> FEATURE:
<221> NAME/KEY: MISC_FEATURE
<222> LOCATION: (35)..(35)
<223> OTHER INFORMATION: Xaa = S or D
<220> FEATURE:
<221> NAME/KEY: MISC_FEATURE
<222> LOCATION: (44)..(44)
<223> OTHER INFORMATION: Xaa = T or N
<220> FEATURE:
<221> NAME/KEY: MISC_FEATURE
<222> LOCATION: (46)..(46)
<223> OTHER INFORMATION: Xaa = R or N
<220> FEATURE:
<221> NAME/KEY: MISC_FEATURE
<222> LOCATION: (47)..(47)
<223> OTHER INFORMATION: Xaa = N or I
<220> FEATURE:
<221> NAME/KEY: MISC_FEATURE
<222> LOCATION: (48)..(48)
<223> OTHER INFORMATION: Xaa = any amino acid
<220> FEATURE:
<221> NAME/KEY: MISC_FEATURE
<222> LOCATION: (50)..(50)
<223> OTHER INFORMATION: Xaa = N or Y or H
<220> FEATURE:
<221> NAME/KEY: MISC_FEATURE
<222> LOCATION: (52)..(52)
<223> OTHER INFORMATION: Xaa = H or Y
<220> FEATURE:
<221> NAME/KEY: MISC_FEATURE
<222> LOCATION: (53)..(53)
<223> OTHER INFORMATION: Xaa = G or R
<220> FEATURE:
<221> NAME/KEY: MISC_FEATURE
<222> LOCATION: (54)..(56)
<223> OTHER INFORMATION: Xaa = any amino acid
<220> FEATURE:
<221> NAME/KEY: MISC_FEATURE
<222> LOCATION: (57)..(57)
<223> OTHER INFORMATION: Xaa = D or N
<220> FEATURE:
<221> NAME/KEY: MISC_FEATURE
<222> LOCATION: (60)..(60)
<223> OTHER INFORMATION: Xaa = D or N
<220> FEATURE:
<221> NAME/KEY: MISC_FEATURE
<222> LOCATION: (61)..(61)
<223> OTHER INFORMATION: Xaa = S or Y
<220> FEATURE:
<221> NAME/KEY: MISC_FEATURE
<222> LOCATION: (65)..(65)
<223> OTHER INFORMATION: Xaa = N or Q
<220> FEATURE:
<221> NAME/KEY: MISC_FEATURE
<222> LOCATION: (71)..(71)
<223> OTHER INFORMATION: Xaa = L or M
<220> FEATURE:
<221> NAME/KEY: MISC_FEATURE
<222> LOCATION: (75)..(75)
<223> OTHER INFORMATION: Xaa = K or Q
<220> FEATURE:
<221> NAME/KEY: MISC_FEATURE
<222> LOCATION: (77)..(77)
<223> OTHER INFORMATION: Xaa = Y or F
<220> FEATURE:
<221> NAME/KEY: MISC_FEATURE
<222> LOCATION: (79)..(79)
<223> OTHER INFORMATION: Xaa = R or W
<220> FEATURE:
<221> NAME/KEY: MISC_FEATURE
<222> LOCATION: (84)..(84)
<223> OTHER INFORMATION: Xaa = Y or L
<220> FEATURE:
```

```
<221> NAME/KEY: MISC_FEATURE
<222> LOCATION: (85)..(85)
<223> OTHER INFORMATION: Xaa = S or A
<220> FEATURE:
<221> NAME/KEY: MISC_FEATURE
<222> LOCATION: (89)..(89)
<223> OTHER INFORMATION: Xaa = I or V
<220> FEATURE:
<221> NAME/KEY: MISC_FEATURE
<222> LOCATION: (95)..(95)
<223> OTHER INFORMATION: Xaa = I or L
<220> FEATURE:
<221> NAME/KEY: MISC_FEATURE
<222> LOCATION: (99)..(99)
<223> OTHER INFORMATION: Xaa = V or G
<220> FEATURE:
<221> NAME/KEY: MISC_FEATURE
<222> LOCATION: (114)..(114)
<223> OTHER INFORMATION: Xaa = C or L
<220> FEATURE:
<221> NAME/KEY: MISC_FEATURE
<222> LOCATION: (115)..(115)
<223> OTHER INFORMATION: Xaa = A or S
<220> FEATURE:
<221> NAME/KEY: MISC_FEATURE
<222> LOCATION: (116)..(116)
<223> OTHER INFORMATION: Xaa = V or M
<220> FEATURE:
<221> NAME/KEY: MISC_FEATURE
<222> LOCATION: (117)..(117)
<223> OTHER INFORMATION: Xaa = V or T
<220> FEATURE:
<221> NAME/KEY: MISC_FEATURE
<222> LOCATION: (118)..(118)
<223> OTHER INFORMATION: Xaa = R or C
<220> FEATURE:
<221> NAME/KEY: MISC_FEATURE
<222> LOCATION: (122)..(122)
<223> OTHER INFORMATION: Xaa = F or P
<220> FEATURE:
<221> NAME/KEY: MISC_FEATURE
<222> LOCATION: (125)..(125)
<223> OTHER INFORMATION: Xaa = L or V
<220> FEATURE:
<221> NAME/KEY: MISC_FEATURE
<222> LOCATION: (126)..(126)
<223> OTHER INFORMATION: Xaa = A or V
<220> FEATURE:
<221> NAME/KEY: MISC_FEATURE
<222> LOCATION: (128)..(128)
<223> OTHER INFORMATION: Xaa = S or A
<220> FEATURE:
<221> NAME/KEY: MISC_FEATURE
<222> LOCATION: (133)..(133)
<223> OTHER INFORMATION: Xaa = V or L or M
<220> FEATURE:
<221> NAME/KEY: MISC_FEATURE
<222> LOCATION: (138)..(138)
<223> OTHER INFORMATION: Xaa = K or R
<220> FEATURE:
<221> NAME/KEY: MISC_FEATURE
<222> LOCATION: (139)..(139)
<223> OTHER INFORMATION: Xaa = S or T
<220> FEATURE:
<221> NAME/KEY: MISC_FEATURE
<222> LOCATION: (140)..(140)
<223> OTHER INFORMATION: Xaa = V or G
<220> FEATURE:
<221> NAME/KEY: MISC_FEATURE
<222> LOCATION: (141)..(141)
<223> OTHER INFORMATION: Xaa = Q or E
<220> FEATURE:
<221> NAME/KEY: MISC_FEATURE
<222> LOCATION: (143)..(143)
<223> OTHER INFORMATION: Xaa = L or S or R
<220> FEATURE:
<221> NAME/KEY: MISC_FEATURE
<222> LOCATION: (145)..(145)
<223> OTHER INFORMATION: Xaa = S or F
```

```
<220> FEATURE:
<221> NAME/KEY: MISC_FEATURE
<222> LOCATION: (147)..(147)
<223> OTHER INFORMATION: Xaa = F or Y
<220> FEATURE:
<221> NAME/KEY: MISC_FEATURE
<222> LOCATION: (148)..(148)
<223> OTHER INFORMATION: Xaa = T or A
<220> FEATURE:
<221> NAME/KEY: MISC_FEATURE
<222> LOCATION: (149)..(149)
<223> OTHER INFORMATION: Xaa = A or S
<220> FEATURE:
<221> NAME/KEY: MISC_FEATURE
<222> LOCATION: (150)..(150)
<223> OTHER INFORMATION: Xaa = V or I
<220> FEATURE:
<221> NAME/KEY: MISC_FEATURE
<222> LOCATION: (151)..(151)
<223> OTHER INFORMATION: Xaa = T or C
<220> FEATURE:
<221> NAME/KEY: MISC_FEATURE
<222> LOCATION: (152)..(152)
<223> OTHER INFORMATION: Xaa = N or S
<220> FEATURE:
<221> NAME/KEY: MISC_FEATURE
<222> LOCATION: (153)..(153)
<223> OTHER INFORMATION: Xaa = F or V
<220> FEATURE:
<221> NAME/KEY: MISC_FEATURE
<222> LOCATION: (156)..(156)
<223> OTHER INFORMATION: Xaa = S or D
<220> FEATURE:
<221> NAME/KEY: MISC_FEATURE
<222> LOCATION: (157)..(157)
<223> OTHER INFORMATION: Xaa = L or V
<220> FEATURE:
<221> NAME/KEY: MISC_FEATURE
<222> LOCATION: (164)..(164)
<223> OTHER INFORMATION: Xaa = N or Q
<220> FEATURE:
<221> NAME/KEY: MISC_FEATURE
<222> LOCATION: (179)..(179)
<223> OTHER INFORMATION: Xaa = V or I

<400> SEQUENCE: 2

Ser Xaa Leu Ser Trp Leu Ser Leu Asp Val Ser Ala Ala Phe Tyr His
1               5                   10                  15

Xaa Pro Leu His Pro Ala Ala Met Pro His Leu Leu Xaa Gly Ser Ser
            20                  25                  30

Gly Leu Xaa Arg Tyr Val Ala Arg Leu Ser Ser Xaa Ser Xaa Xaa Xaa
        35                  40                  45

Asn Xaa Gln Xaa Xaa Xaa Xaa Xaa Leu His Xaa Xaa Cys Ser Arg
    50                  55                  60

Xaa Leu Tyr Val Ser Leu Xaa Leu Leu Tyr Xaa Thr Xaa Gly Xaa Lys
65                  70                  75                  80

Leu His Leu Xaa Xaa His Pro Ile Xaa Leu Gly Phe Arg Lys Xaa Pro
                85                  90                  95

Met Gly Xaa Gly Leu Ser Pro Phe Leu Leu Ala Gln Phe Thr Ser Ala
            100                 105                 110

Ile Xaa Xaa Xaa Xaa Xaa Arg Ala Phe Xaa His Cys Xaa Xaa Phe Xaa
        115                 120                 125

Tyr Met Asp Asp Xaa Val Leu Gly Ala Xaa Xaa Xaa Xaa His Xaa Glu
130                 135                 140

Xaa Leu Xaa Xaa Xaa Xaa Xaa Xaa Leu Leu Xaa Xaa Gly Ile His
145                 150                 155                 160

Leu Asn Pro Xaa Lys Thr Lys Arg Trp Gly Tyr Ser Leu Asn Phe Met
            165                 170                 175
```

Gly Tyr Xaa Ile Gly
            180

<210> SEQ ID NO 3
<211> LENGTH: 23
<212> TYPE: DNA
<213> ORGANISM: artificial sequence
<220> FEATURE:
<223> OTHER INFORMATION: Synthetic oligonucleotide

<400> SEQUENCE: 3
gcctcatttt gtgggtcacc ata                                            23

<210> SEQ ID NO 4
<211> LENGTH: 18
<212> TYPE: DNA
<213> ORGANISM: artificial sequence
<220> FEATURE:
<223> OTHER INFORMATION: Synthetic oligonucleotide

<400> SEQUENCE: 4
aaattcgcag tccccaaa                                                  18

<210> SEQ ID NO 5
<211> LENGTH: 21
<212> TYPE: DNA
<213> ORGANISM: artificial sequence
<220> FEATURE:
<223> OTHER INFORMATION: Synthetic oligonucleotide

<400> SEQUENCE: 5
ttggggtgga gccctcaggc t                                              21

<210> SEQ ID NO 6
<211> LENGTH: 18
<212> TYPE: DNA
<213> ORGANISM: artificial sequence
<220> FEATURE:
<223> OTHER INFORMATION: Synthetic oligonucleotide

<400> SEQUENCE: 6
gaaaattggt aacagcgg                                                  18

<210> SEQ ID NO 7
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 7
tctctgacat actttccaat                                                20

<210> SEQ ID NO 8
<211> LENGTH: 23
<212> TYPE: DNA
<213> ORGANISM: artificial sequence
<220> FEATURE:
<223> OTHER INFORMATION: Synthetic oligonucleotide

<400> SEQUENCE: 8
gcctcatttt gtgggtcacc ata                                            23

<210> SEQ ID NO 9
<211> LENGTH: 20

```
<212> TYPE: DNA
<213> ORGANISM: artificial sequence
<220> FEATURE:
<223> OTHER INFORMATION: Synthetic oligonucleotide

<400> SEQUENCE: 9
tctctgacat actttccaat                                                    20

<210> SEQ ID NO 10
<211> LENGTH: 18
<212> TYPE: DNA
<213> ORGANISM: artificial sequence
<220> FEATURE:
<223> OTHER INFORMATION: Synthetic oligonucleotide

<400> SEQUENCE: 10
tgcacgattc ctgctcaa                                                      18

<210> SEQ ID NO 11
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 11
tttctcaaag gtggagacag                                                    20

<210> SEQ ID NO 12
<211> LENGTH: 18
<212> TYPE: DNA
<213> ORGANISM: artificial sequence
<220> FEATURE:
<223> OTHER INFORMATION: Synthetic oligonucleotide

<400> SEQUENCE: 12
gggaggagat taggttaa                                                      18

<210> SEQ ID NO 13
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 13
ggcaaaaacg agagtaactc                                                    20

<210> SEQ ID NO 14
<211> LENGTH: 42
<212> TYPE: DNA
<213> ORGANISM: artificial sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: n = L

<400> SEQUENCE: 14
cgcgtcctac tgttcaagcc tccaagctgt gacgcgdabc yn                           42

<210> SEQ ID NO 15
<211> LENGTH: 280
<212> TYPE: DNA
<213> ORGANISM: artificial sequence
<220> FEATURE:
```

<223> OTHER INFORMATION: Synthetic oligonucleotide
<220> FEATURE:
<221> NAME/KEY: misc_feature
<222> LOCATION: (215)..(215)
<223> OTHER INFORMATION: n = any nucleotide

<400> SEQUENCE: 15

```
tggctcagtt tactagtgcc atttgttcag tggttcgtag ggctttcccc cactgtttgg      60
ctttcagtta tatggatgat gtggtattgg gggccaagtc tgtayagcay cttgagtccc     120
tttttaccgc tgttaccaat tttcttttgt ctttgggtat acatttaaac cctaacaaaa     180
ctaaaagatg gggttactct ttacatttca tgggntatgt cattggatgt tatgggtcat     240
tgccacaaga tcacatcata cagaaaatca aagatggttt                           280
```

<210> SEQ ID NO 16
<211> LENGTH: 242
<212> TYPE: DNA
<213> ORGANISM: artificial sequence
<220> FEATURE:
<223> OTHER INFORMATION: Synthetic oligonucleotide

<400> SEQUENCE: 16

```
tggctcagtt tactagtgcc atttgttcag tggttcgtag ggctttcccc cactgtttgg      60
ctttcagtta tatggatgat gtggtattgg gggccaagtc tgtacagcat cttgagtccc     120
tttttaccgc tgttaccaat tttcttttgt ctttgggtat acatttaaac cctaacaaaa     180
caaagagatg gggttactct ctaaatttta tgggttatgt cattggatgt tatgggtcct     240
tg                                                                    242
```

<210> SEQ ID NO 17
<211> LENGTH: 277
<212> TYPE: DNA
<213> ORGANISM: artificial sequence
<220> FEATURE:
<223> OTHER INFORMATION: Synthetic oligonucleotide

<400> SEQUENCE: 17

```
tggctcagtt tactagtgcc atttgttcag tggttcgtag ggctttcccc cactgtttgg      60
ctttcagtta tatggatgat gtggtattgg gggccaagtc tgtacagcat cttgagtccc     120
tttttaccgc tgttaccaat tttcttttgt ctttgggtat acatttaaac cctaacaaaa     180
caaagagatg gggttactct ctaaatttta tgggttatgt cattggatgt tatgggtcct     240
tgccacaaga acacatcata caaaaaatca aagaatg                              277
```

<210> SEQ ID NO 18
<211> LENGTH: 237
<212> TYPE: DNA
<213> ORGANISM: artificial sequence
<220> FEATURE:
<223> OTHER INFORMATION: Synthetic oligonucleotide

<400> SEQUENCE: 18

```
tggctcagtt tactagtgcc atttgttcag tggttcgtag ggctttcccc cactgtttgg      60
ctttcagtta tatggatgat gtggtattgg gggccaagtc tgtacagcat cttgagtccc     120
tttttaccgc tgttaccaat tttcttttgt ctttgggcat acatttaaac cctaacaaaa     180
ctaaaagatg ggggtactct ttaaatttca tgggatatgt cattggatgg tatgggg        237
```

<210> SEQ ID NO 19
<211> LENGTH: 336

```
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid
<220> FEATURE:
<221> NAME/KEY: MISC_FEATURE
<222> LOCATION: (38)..(38)
<223> OTHER INFORMATION: Xaa = any amino acid
<220> FEATURE:
<221> NAME/KEY: MISC_FEATURE
<222> LOCATION: (46)..(46)
<223> OTHER INFORMATION: Xaa = any amino acid
<220> FEATURE:
<221> NAME/KEY: MISC_FEATURE
<222> LOCATION: (50)..(50)
<223> OTHER INFORMATION: Xaa = any amino acid
<220> FEATURE:
<221> NAME/KEY: MISC_FEATURE
<222> LOCATION: (101)..(101)
<223> OTHER INFORMATION: Xaa = any amino acid
<220> FEATURE:
<221> NAME/KEY: MISC_FEATURE
<222> LOCATION: (208)..(208)
<223> OTHER INFORMATION: Xaa = any amino acid
<220> FEATURE:
<221> NAME/KEY: MISC_FEATURE
<222> LOCATION: (295)..(295)
<223> OTHER INFORMATION: Xaa = any amino acid

<400> SEQUENCE: 19

Lys Leu Ala Ser Lys Ser Ala Ser Ser Ile Xaa Gln Ser Pro Val Arg
1               5                   10                  15

Xaa Ala Ala Tyr Pro Ala Val Ser Thr Phe Glu Lys His Ser Ser Ser
                20                  25                  30

Gly His Ala Val Glu Xaa His Asn Leu Pro Pro Asn Ser Xaa Arg Ser
            35                  40                  45

Gln Xaa Glu Arg Pro Val Phe Pro Cys Trp Trp Leu Gln Phe Arg Asn
    50                  55                  60

Ser Lys Pro Cys Ser Asp Tyr Cys Leu Ser His Ile Val Asn Leu Leu
65                  70                  75                  80

Glu Asp Trp Gly Pro Cys Ala Glu His Gly Glu His His Ile Arg Ile
                85                  90                  95

Pro Arg Thr Pro Xaa Arg Val Thr Gly Gly Val Phe Leu Val Asp Lys
            100                 105                 110

Asn Pro His Asn Thr Ala Glu Ser Arg Leu Val Val Asp Phe Ser Gln
        115                 120                 125

Phe Ser Arg Gly Asn Tyr Arg Val Ser Trp Pro Lys Phe Ala Val Pro
    130                 135                 140

Asn Leu Gln Ser Leu Thr Asn Leu Leu Ser Ser Asn Leu Ser Trp Leu
145                 150                 155                 160

Ser Leu Asp Val Ser Ala Ala Phe Tyr His Leu Pro Leu His Pro Ala
                165                 170                 175

Ala Met Pro His Leu Leu Val Gly Ser Ser Gly Leu Ser Arg Tyr Val
            180                 185                 190

Ala Arg Leu Ser Ser Asn Ser Arg Ile Phe Asn His Gln Arg Gly Xaa
        195                 200                 205

Met Gln Asn Leu His Asp Tyr Cys Ser Arg Asn Leu Tyr Val Ser Leu
```

-continued

```
                210                 215                 220
Leu Leu Leu Tyr Gln Thr Phe Gly Arg Lys Leu His Leu Tyr Ser His
225                 230                 235                 240

Pro Ile Ile Leu Gly Phe Arg Lys Ile Pro Met Gly Val Gly Leu Ser
                245                 250                 255

Pro Phe Leu Leu Ala Gln Phe Thr Ser Ala Ile Cys Ser Val Val Arg
                260                 265                 270

Arg Ala Phe Pro His Cys Leu Ala Phe Ser Tyr Met Asp Asp Val Val
                275                 280                 285

Leu Gly Ala Lys Ser Val Xaa His Leu Glu Ser Leu Phe Thr Ala Val
                290                 295                 300

Thr Asn Phe Leu Leu Ser Leu Gly Ile His Leu Asn Pro Asn Lys Thr
305                 310                 315                 320

Lys Arg Trp Gly Tyr Ser Leu His Phe Met Gly Tyr Val Ile Gly Cys
                325                 330                 335

<210> SEQ ID NO 20
<211> LENGTH: 340
<212> TYPE: PRT
<213> ORGANISM: artificial sequence
<220> FEATURE:
<223> OTHER INFORMATION: Synthetic peptide

<400> SEQUENCE: 20

His Thr Thr Asn Phe Ala Ser Lys Ser Ala Ser Cys Leu His Gln Ser
1               5                   10                  15

Pro Val Arg Lys Ala Ala Tyr Pro Ala Val Ser Thr Phe Glu Lys His
                20                  25                  30

Ser Ser Ser Gly His Ala Val Glu Phe His Asn Leu Pro Pro Asn Ser
                35                  40                  45

Ala Arg Ser Gln Ser Glu Arg Pro Val Phe Pro Cys Trp Trp Leu Gln
50                  55                  60

Phe Arg Asn Ser Lys Pro Cys Ser Asp Tyr Cys Leu Ser Leu Ile Val
65                  70                  75                  80

Asn Leu Leu Glu Asp Trp Gly Pro Cys Ala Glu His Gly Glu His His
                85                  90                  95

Ile Arg Ile Pro Arg Thr Pro Ser Arg Val Thr Gly Gly Val Phe Leu
                100                 105                 110

Val Asp Lys Asn Pro His Asn Thr Ala Glu Ser Arg Leu Val Val Asp
                115                 120                 125

Phe Ser Gln Phe Ser Arg Gly Asn Tyr Arg Val Ser Trp Pro Lys Phe
130                 135                 140

Ala Val Pro Asn Leu Gln Ser Leu Thr Asn Leu Leu Ser Ser Asn Leu
145                 150                 155                 160

Ser Trp Leu Ser Leu Asp Val Ser Ala Ala Phe Tyr His Leu Pro Leu
                165                 170                 175

His Pro Ala Ala Met Pro His Leu Leu Val Gly Ser Ser Gly Leu Ser
                180                 185                 190

Arg Tyr Val Ala Arg Leu Ser Ser Asn Ser Arg Ile Leu Asn Asn Gln
                195                 200                 205

His Gly Thr Met Pro Asp Leu His Asp Tyr Cys Ser Arg Asn Leu Tyr
                210                 215                 220

Val Ser Leu Leu Leu Leu Tyr Gln Thr Phe Gly Arg Lys Leu His Leu
225                 230                 235                 240

Tyr Ser His Pro Ile Ile Leu Gly Phe Arg Lys Ile Pro Met Gly Val
```

```
                  245                 250                 255
Gly Leu Ser Pro Phe Leu Ala Gln Phe Thr Ser Ala Ile Cys Ser
            260                 265                 270

Val Val Arg Arg Ala Phe Pro His Cys Leu Ala Phe Ser Tyr Met Asp
        275                 280                 285

Asp Val Val Leu Gly Ala Lys Ser Val Gln His Leu Glu Ser Leu Phe
    290                 295                 300

Thr Ala Val Thr Asn Phe Leu Leu Ser Leu Gly Ile His Leu Asn Pro
305                 310                 315                 320

Asn Lys Thr Lys Arg Trp Gly Tyr Ser Leu Asn Phe Met Gly Tyr Val
                325                 330                 335

Ile Gly Cys Tyr
            340

<210> SEQ ID NO 21
<211> LENGTH: 344
<212> TYPE: PRT
<213> ORGANISM: artificial sequence
<220> FEATURE:
<223> OTHER INFORMATION: Synthetic peptide

<400> SEQUENCE: 21

Leu Ala Gln Gly Ile Leu Gln Asn Phe Ala Ser Lys Ser Ala Ser Cys
1               5                   10                  15

Leu His Gln Ser Pro Val Arg Lys Ala Ala Tyr Pro Ala Val Ser Thr
            20                  25                  30

Phe Glu Lys His Ser Ser Ser Gly His Ala Val Glu Phe His Asn Leu
        35                  40                  45

Pro Pro Asn Ser Ala Arg Ser Gln Ser Glu Arg Pro Val Phe Pro Cys
    50                  55                  60

Trp Trp Leu Gln Phe Arg Asn Ser Lys Pro Cys Ser Asp Tyr Cys Leu
65                  70                  75                  80

Ser Leu Ile Val Asn Leu Leu Glu Asp Trp Gly Pro Cys Ala Glu His
                85                  90                  95

Gly Glu His His Ile Arg Ile Pro Arg Thr Pro Ser Arg Val Thr Gly
            100                 105                 110

Gly Val Phe Leu Val Asp Lys Asn Pro His Asn Thr Ala Glu Ser Arg
        115                 120                 125

Leu Val Val Asp Phe Ser Gln Phe Ser Arg Gly Asn Tyr Arg Val Ser
    130                 135                 140

Trp Pro Lys Phe Ala Val Pro Asn Leu Gln Ser Leu Thr Asn Leu Leu
145                 150                 155                 160

Ser Ser Asn Leu Ser Trp Leu Ser Leu Asp Val Ser Ala Ala Phe Tyr
                165                 170                 175

His Leu Pro Leu His Pro Ala Ala Met Pro His Leu Leu Val Gly Ser
            180                 185                 190

Ser Gly Leu Ser Arg Tyr Val Ala Arg Leu Ser Ser Asn Ser Arg Ile
        195                 200                 205

Leu Asn Asn Gln His Gly Thr Met Pro Asp Leu His Asp Tyr Cys Ser
    210                 215                 220

Arg Asn Leu Tyr Val Ser Leu Leu Leu Leu Tyr Gln Thr Phe Gly Arg
225                 230                 235                 240

Lys Leu His Leu Tyr Ser His Pro Ile Ile Leu Gly Phe Arg Lys Ile
                245                 250                 255

Pro Met Gly Val Gly Leu Ser Pro Phe Leu Leu Ala Gln Phe Thr Ser
```

```
                    260                 265                 270
Ala Ile Cys Ser Val Val Arg Arg Ala Phe Pro His Cys Leu Ala Phe
            275                 280                 285
Ser Tyr Met Asp Asp Val Val Leu Gly Ala Lys Ser Val Gln His Leu
        290                 295                 300
Glu Ser Leu Phe Thr Ala Val Thr Asn Phe Leu Leu Ser Leu Gly Ile
305                 310                 315                 320
His Leu Asn Pro Asn Lys Thr Lys Arg Trp Gly Tyr Ser Leu Asn Phe
                325                 330                 335
Met Gly Tyr Val Ile Gly Cys Tyr
            340

<210> SEQ ID NO 22
<211> LENGTH: 336
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (24)..(24)
<223> OTHER INFORMATION: Xaa =any amino acid

<400> SEQUENCE: 22

Ala Ser Lys Ser Ala Ser Ser Ile Tyr Gln Ser Pro Val Gly Thr Ala
1               5                   10                  15

Ala Tyr Pro Ala Val Ser Thr Xaa Glu Lys His Ser Ser Ser Gly His
            20                  25                  30

Ala Val Glu Leu His Asn Leu Pro Pro Asn Ser Glu Arg Ser Gln Gly
        35                  40                  45

Glu Arg Pro Val Phe Pro Cys Trp Trp Leu Gln Phe Arg Asn Ser Lys
    50                  55                  60

Pro Cys Ser Asp Tyr Cys Leu Ser His Ile Val Asn Leu Leu Glu Asp
65                  70                  75                  80

Trp Gly Pro Cys Ala Glu His Gly Glu His His Ile Arg Ile Pro Arg
                85                  90                  95

Thr Pro Ala Arg Val Thr Gly Gly Val Phe Leu Val Asp Lys Asn Pro
            100                 105                 110

His Asn Thr Ala Glu Ser Arg Leu Val Val Asp Phe Ser Gln Phe Ser
        115                 120                 125

Arg Gly Asn Tyr Arg Val Ser Trp Pro Lys Phe Ala Val Pro Asn Leu
    130                 135                 140

Gln Ser Leu Thr Asn Leu Leu Ser Ser Asn Leu Ser Trp Leu Ser Leu
145                 150                 155                 160

Asp Val Ser Ala Ala Phe Tyr His Leu Pro Leu His Pro Ala Ala Met
                165                 170                 175

Pro His Leu Leu Val Gly Ser Ser Gly Leu Ser Arg Tyr Val Ala Arg
            180                 185                 190

Leu Ser Ser Asn Ser Arg Ile Phe Asn His Gln Arg Gly Asn Met Gln
        195                 200                 205

Asn Leu His Asp Cys Cys Ser Arg Asn Leu Tyr Val Ser Leu Leu Leu
    210                 215                 220

Leu Tyr Gln Thr Phe Gly Arg Lys Leu His Leu Tyr Ser His Pro Ile
225                 230                 235                 240

Ile Leu Gly Phe Arg Lys Ile Pro Met Gly Val Gly Leu Ser Pro Phe
                245                 250                 255
```

```
Leu Leu Ala Gln Phe Thr Ser Ala Ile Cys Ser Val Val Arg Arg Ala
                260                 265                 270

Phe Pro His Cys Leu Ala Phe Ser Tyr Met Asp Asp Val Val Leu Gly
            275                 280                 285

Ala Lys Ser Val Gln His Leu Glu Ser Leu Phe Thr Ala Val Thr Asn
        290                 295                 300

Phe Leu Leu Ser Leu Gly Ile His Leu Asn Pro Asn Lys Thr Lys Arg
305                 310                 315                 320

Trp Gly Tyr Ser Leu Asn Phe Met Gly Tyr Val Ile Gly Trp Tyr Gly
                325                 330                 335

<210> SEQ ID NO 23
<211> LENGTH: 226
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (120)..(120)
<223> OTHER INFORMATION: Xaa = any amino acid
<220> FEATURE:
<221> NAME/KEY: MISC_FEATURE
<222> LOCATION: (208)..(208)
<223> OTHER INFORMATION: Xaa = any amino acid

<400> SEQUENCE: 23

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Ala Gly Xaa Cys Arg Thr Cys Thr Thr Thr Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Xaa
        195                 200                 205

Leu Ser Pro Phe Leu Pro Leu Leu Pro Ile Phe Phe Cys Leu Trp Val
    210                 215                 220

Tyr Ile
225
```

<210> SEQ ID NO 24
<211> LENGTH: 309
<212> TYPE: PRT
<213> ORGANISM: artificial sequence
<220> FEATURE:
<223> OTHER INFORMATION: Synthetic peptide

<400> SEQUENCE: 24

```
Pro Pro Pro Ala Ser Thr Asn Arg Gln Ser Gly Arg Gln Pro Thr Pro
1               5                   10                  15

Leu Ser Pro Pro Leu Arg Asn Thr His Pro Gln Ala Met Gln Trp Asn
            20                  25                  30

Ser Thr Thr Phe His Gln Thr Leu Gln Asp Pro Arg Val Arg Gly Leu
        35                  40                  45

Tyr Phe Pro Ala Gly Gly Ser Ser Gly Thr Val Asn Pro Val Leu
    50                  55                  60

Thr Thr Ala Ser Pro Leu Ser Ser Ile Phe Ser Arg Ile Gly Asp Pro
65                  70                  75                  80

Ala Leu Asn Met Glu Asn Ile Thr Ser Gly Phe Leu Gly Pro Leu Leu
                85                  90                  95

Val Leu Gln Ala Gly Phe Phe Leu Leu Thr Arg Ile Leu Thr Ile Pro
            100                 105                 110

Gln Ser Leu Asp Ser Trp Trp Thr Ser Leu Asn Phe Leu Gly Gly Thr
        115                 120                 125

Thr Val Cys Leu Gly Gln Asn Ser Gln Ser Pro Thr Ser Asn His Ser
    130                 135                 140

Pro Thr Ser Cys Pro Pro Thr Cys Pro Gly Tyr Arg Trp Met Cys Leu
145                 150                 155                 160

Arg Arg Phe Ile Ile Phe Leu Phe Ile Leu Leu Leu Cys Leu Ile Phe
                165                 170                 175

Leu Leu Val Leu Leu Asp Tyr Gln Gly Met Leu Pro Val Cys Pro Leu
            180                 185                 190

Ile Pro Gly Ser Ser Thr Thr Ser Thr Gly Pro Cys Arg Thr Cys Met
        195                 200                 205

Thr Thr Ala Gln Gly Thr Ser Met Tyr Pro Ser Cys Cys Cys Thr Lys
    210                 215                 220

Pro Ser Asp Gly Asn Cys Thr Cys Ile Pro Ile Pro Ser Ser Trp Ala
225                 230                 235                 240

Phe Gly Lys Phe Leu Trp Glu Trp Ala Ser Ala Arg Phe Ser Trp Leu
                245                 250                 255

Ser Leu Leu Val Pro Phe Val Gln Trp Phe Val Gly Leu Ser Pro Thr
            260                 265                 270

Val Trp Leu Ser Val Ile Trp Met Met Trp Tyr Trp Gly Pro Ser Leu
        275                 280                 285

Tyr Ser Ile Leu Ser Pro Phe Leu Pro Leu Leu Pro Ile Phe Phe Cys
    290                 295                 300

Leu Trp Val Tyr Ile
305
```

<210> SEQ ID NO 25
<211> LENGTH: 309
<212> TYPE: PRT
<213> ORGANISM: artificial sequence
<220> FEATURE:
<223> OTHER INFORMATION: Synthetic peptide

<400> SEQUENCE: 25

```
Pro Pro Pro Ala Ser Thr Asn Arg Gln Ser Gly Arg Gln Pro Thr Pro
1               5                   10                  15

Leu Ser Pro Pro Leu Arg Asn Thr His Pro Gln Ala Met Gln Trp Asn
            20                  25                  30

Ser Thr Thr Phe His Gln Thr Leu Gln Asp Pro Arg Val Arg Gly Leu
        35                  40                  45

Tyr Phe Pro Ala Gly Gly Ser Ser Gly Thr Val Asn Pro Val Leu
50                  55                  60

Thr Thr Ala Ser Pro Leu Ser Ser Ile Phe Ser Arg Ile Gly Asp Pro
65              70                  75                  80

Ala Leu Asn Met Glu Asn Ile Thr Ser Gly Phe Leu Gly Pro Leu Leu
                85                  90                  95

Val Leu Gln Ala Gly Phe Phe Leu Leu Thr Arg Ile Leu Thr Ile Pro
                100                 105                 110

Gln Ser Leu Asp Ser Trp Trp Thr Ser Leu Asn Phe Leu Gly Gly Thr
            115                 120                 125

Thr Val Cys Leu Gly Gln Asn Ser Gln Ser Pro Thr Ser Asn His Ser
130                 135                 140

Pro Thr Ser Cys Pro Pro Thr Cys Pro Gly Tyr Arg Trp Met Cys Leu
145                 150                 155                 160

Arg Arg Phe Ile Ile Phe Leu Phe Ile Leu Leu Leu Cys Leu Ile Phe
                165                 170                 175

Leu Leu Val Leu Leu Asp Tyr Gln Gly Met Leu Pro Val Cys Pro Leu
            180                 185                 190

Ile Pro Gly Ser Ser Thr Thr Ser Thr Gly Pro Cys Arg Thr Cys Met
            195                 200                 205

Thr Thr Ala Gln Gly Thr Ser Met Tyr Pro Ser Cys Cys Cys Thr Lys
210                 215                 220

Pro Ser Asp Gly Asn Cys Thr Cys Ile Pro Ile Pro Ser Ser Trp Ala
225                 230                 235                 240

Phe Gly Lys Phe Leu Trp Glu Trp Ala Ser Ala Arg Phe Ser Trp Leu
                245                 250                 255

Ser Leu Leu Val Pro Phe Val Gln Trp Phe Val Gly Leu Ser Pro Thr
            260                 265                 270

Val Trp Leu Ser Val Ile Trp Met Met Trp Tyr Trp Gly Pro Ser Leu
            275                 280                 285

Tyr Ser Ile Leu Ser Pro Phe Leu Pro Leu Leu Pro Ile Phe Phe Cys
290                 295                 300

Leu Trp Val Tyr Ile
305
```

<210> SEQ ID NO 26
<211> LENGTH: 309
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (21)..(21)
<223> OTHER INFORMATION: Xaa = any amino acid
<220> FEATURE:
<221> NAME/KEY: MISC_FEATURE
<222> LOCATION: (46)..(46)
<223> OTHER INFORMATION: Xaa = any amino acid

<400> SEQUENCE: 26

Pro Pro Pro Pro Ser Thr Asn Arg Gln Ser Gly Arg Gln Pro Thr Pro

```
1               5                   10                  15
Leu Ser Pro Pro Xaa Arg Asn Thr His Pro Gln Ala Met Gln Trp Asn
            20                  25                  30

Ser Thr Thr Phe His Gln Thr Leu Lys Asp Pro Arg Val Xaa Gly Leu
        35                  40                  45

Tyr Phe Pro Ala Gly Gly Ser Ser Gly Thr Val Asn Pro Val Pro
    50                  55                  60

Thr Thr Ala Ser Pro Ile Ser Ser Ile Phe Ser Arg Ile Gly Asp Pro
65                  70                  75                  80

Ala Leu Asn Met Glu Asn Ile Thr Ser Gly Phe Leu Gly Pro Leu Leu
                85                  90                  95

Val Leu Gln Ala Gly Phe Phe Leu Leu Thr Arg Ile Leu Thr Ile Pro
            100                 105                 110

Gln Ser Leu Asp Ser Trp Trp Thr Ser Leu Asn Phe Leu Gly Gly Thr
        115                 120                 125

Thr Val Cys Leu Gly Gln Asn Ser Gln Ser Pro Thr Ser Asn His Ser
    130                 135                 140

Pro Thr Ser Cys Pro Pro Thr Cys Pro Gly Tyr Arg Trp Met Cys Leu
145                 150                 155                 160

Arg Arg Phe Ile Ile Phe Leu Phe Ile Leu Leu Leu Cys Leu Ile Phe
                165                 170                 175

Leu Leu Val Leu Leu Asp Tyr Gln Gly Met Leu Pro Val Cys Pro Leu
            180                 185                 190

Ile Pro Gly Ser Ser Thr Thr Ser Ala Gly Thr Cys Arg Thr Cys Thr
        195                 200                 205

Thr Ala Ala Gln Gly Thr Ser Met Tyr Pro Ser Cys Cys Cys Thr Lys
    210                 215                 220

Pro Ser Asp Gly Asn Cys Thr Cys Ile Pro Ile Pro Ser Ser Trp Ala
225                 230                 235                 240

Phe Gly Lys Phe Leu Trp Glu Trp Ala Ser Ala Arg Phe Ser Trp Leu
                245                 250                 255

Ser Leu Leu Val Pro Phe Val Gln Trp Phe Val Gly Leu Ser Pro Thr
            260                 265                 270

Val Trp Leu Ser Val Ile Trp Met Met Trp Tyr Trp Gly Pro Ser Leu
        275                 280                 285

Tyr Ser Ile Leu Ser Pro Phe Leu Pro Leu Leu Pro Ile Phe Phe Cys
    290                 295                 300

Leu Trp Ala Tyr Ile
305
```

<210> SEQ ID NO 27
<211> LENGTH: 656
<212> TYPE: DNA
<213> ORGANISM: artificial sequence
<220> FEATURE:
<223> OTHER INFORMATION: Synthetic oligonucleotide
<220> FEATURE:
<221> NAME/KEY: misc_feature
<222> LOCATION: (561)..(561)
<223> OTHER INFORMATION: n = any nucleotide

<400> SEQUENCE: 27
cgcagagtct agactcgtgg tggacttctc tcaattttcg agggggggact accgtgtgtc    60 ttggccaaaa ttcgcagtcc ccaacctcca atcactcacc aacctcctgt cctccaactt   120
gtcctggtta tcgctggatg tgtctgcggc gttttatcat cttcctcttc atcctgctgc   180

| | |
|---|---:|
| tatgcctcat cttcttgttg gttcttctgg actgtcaagg tatgttgccc gtttgtcctc | 240 |
| taattccagg atcctcaacc accagcacgg gaccatgccg aacctgcacg actcctgctc | 300 |
| aaggaacctc tacggttccc tcatgttgct gtaccaaacc ttcggacgga aattgcacct | 360 |
| gtattcccat cccatcatcc tgggctttcg gaaaattcct atgggagtgg gcctcagccc | 420 |
| gtttctcctg gctcagttta ctagtgccat ttgttcagtg gttcgtaggg ctttccccca | 480 |
| ctgtctggct tttagttata tggatgatgt ggtattgggg gccaagtctg tatcgcatct | 540 |
| tgagtccctt tttaccgctg ntaccaattt tcttttgtct tgggtatac atttaaaccc | 600 |
| taacaaaaca aaaagatggg gttactccct acattttatg ggctatgtca ttggat | 656 |

<210> SEQ ID NO 28
<211> LENGTH: 625
<212> TYPE: DNA
<213> ORGANISM: artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n = any nucleotide

<400> SEQUENCE: 28

| | |
|---|---:|
| ttactcaccn acctcctgtc ctccaacttg tcctggttat cgctggatgt gtctgcggcg | 60 |
| ttttatcatc ttcctcttca tcctgctgct atgcctcatc ttcttgttgg ttcttctgga | 120 |
| ctgtcaaggt atgttgcccg tttgtcctct aattccagga tcctcaacca ccagcagggg | 180 |
| accatgccga acctgcacga ctcctgctca aggaacctct acggttccct catgttgctg | 240 |
| taccaaacct tcggacggaa attgcacctg tattcccatc ccatcatcct gggctttcgg | 300 |
| aaaattccta tgggagtggg cctcagcccg tttctcatgg ctcagtttac tagtgccatt | 360 |
| tgttcagtgg ttcgtagggc tttcccccac tgtctggctt ttggttatgt ggatgatgtg | 420 |
| gtattggggg ccaagtctgt atcgcatctt gagtcccttt ttaccgctgt taccaattt | 480 |
| cttttgtctt gggtataca tttaaatcct aacaaaacaa aaagatgggg ttactcccta | 540 |
| cattttatgg gctatgtcat ggatgtcat gggtccttgc acaagaaca catcagacaa | 600 |
| aaaatcaaag aatgttttag aaaac | 625 |

<210> SEQ ID NO 29
<211> LENGTH: 1033
<212> TYPE: DNA
<213> ORGANISM: artificial sequence
<220> FEATURE:
<223> OTHER INFORMATION: Synthetic oligonucleotide

<400> SEQUENCE: 29

| | |
|---|---:|
| tgccccttct gcctccacca atcgccagtc aggaaggcag cctaccccgc tgtctccacc | 60 |
| tttgagagac actcatcctc aggccatgca gtggaactca acaaccttcc accaaactct | 120 |
| gcaagatccc agagtgaaag gcctgtattt ccctgctggt ggctccagtt caggaacagt | 180 |
| aaaccctgtt ccgactactg cctctcactc atcgtcaatc ttctcgagga ttggggtccc | 240 |
| tgcgctgaac atggagaaca tcacatcagg actcctagga ccccttctcg tgttacaggc | 300 |
| ggggttttc ttgttgacaa gaatcctcac aataccgcag agtctagact cgtggtggac | 360 |
| ttctctcaat tttcgagggg ggactaccgt gtgtcttggc caaaattcgc agtccccaac | 420 |
| ctccaatcac tcaccaacct cctgtcctcc aacttgtcct ggttatcgct ggatgtgtct | 480 |
| gcggcgtttt atcatcttcc tcttcatcct gctgctatgc ctcatcttct gttggttct | 540 |

```
tctggactgt caaggtatgt tgcccgtttg tcctctaatt ccaggatcct caaccaccag      600
caggggacca tgccgaacct gcacgactcc tgctcaagga acctctacgg ttccctcatg      660
ttgctgtacc aaaccttcgg acggaaattg cacctgtatt cccatcccat catcctgggc      720
tttcggaaaa ttcctatggg agtgggcctc agcccgtttc tcatggctca gtttactagt      780
gccatttgtt cagtggttcg tagggctttc ccccactgtc tggcttttgg ttatgtggat      840
gatgtggtat tgggggccaa gtctgtatcg catcttgagt ccctttttac cgctgttacc      900
aattttcttt tgtctttggg tatacattta aatcctaaca aaacaaaaag atggggttac      960
tccctacatt ttatgggcta tgtcattgga tgtcatgggt ccttgccaca agaacacatc     1020
agacaaaaaa tca                                                        1033

<210> SEQ ID NO 30
<211> LENGTH: 1100
<212> TYPE: DNA
<213> ORGANISM: artificial sequence
<220> FEATURE:
<223> OTHER INFORMATION: Synthetic oligonucleotide

<400> SEQUENCE: 30
ttttggggag ccctcaggct cagggcatat tacaaactct gccagcaaat ccacctcctg       60
cctccaccaa tcgccagtca ggaaggcagc ctaccccgct gtctccacct ttgagagaca      120
ctcatcctca ggccatgcag tggaactcaa caaccttcca ccaaactctg caagatccca      180
gagtgaaagg cctgtatttc cctgctggtg gctccagttc aggaacagta aaccctgttc      240
cgactactgc ctctcactca tcgtcaatct tctcgaggat tggggtccct gcgctgaaca      300
tggagaacat cacatcagga ctcctaggac cccttctcgt gttacaggcg ggttttttct      360
tgttgacaag aatcctcaca ataccgcaga gtctagactc gtggtggact tctctcaatt      420
ttcgaggggg gactaccgtg tgtcttggcc aaaattcgca gtccccaacc tccaatcact      480
caccaacctc ctgtcctcca acttgtcctg gttatcgctg gatgtgtctg cggcgtttta      540
tcatcttcct cttcatcctg ctgctatgcc tcatcttctt gttggttctt ctggactgtc      600
aaggtatgtt gcccgtttgt cctctaattc aggatcctc aaccaccagc aggggaccat      660
gccgaacctg cacgactcct gctcaaggaa cctctacggt tccctcatgt tgctgtacca      720
aaccttcgga cggaaattgc acctgtattc ccatcccatc atcctgggct ttcggaaaat      780
tcctatggga gtgggcctca gcccgtttct catggctcag tttactagtg ccatttgttc      840
agtggttcgt agggctttcc cccactgtct ggcttttggt tatgtggatg atgtggtatt      900
gggggccaag tctgtatcgc atcttgagtc ccttttttacc gctgttacca atttttctttt      960 gtctttgggt atacatttaa atcctaacaa aacaaaaaga tggggttact ccctacattt     1020
tatgggctat gtcattggat gtcatgggtc cttgccacaa gaacacatca gacaaaaaat     1080
caaagaatgt tttagaaaac                                                 1100

<210> SEQ ID NO 31
<211> LENGTH: 987
<212> TYPE: DNA
<213> ORGANISM: artificial sequence
<220> FEATURE:
<223> OTHER INFORMATION: Synthetic oligonucleotide
<220> FEATURE:
<221> NAME/KEY: misc_feature
<222> LOCATION: (329)..(329)
<223> OTHER INFORMATION: n = any nucleotide
<220> FEATURE:
```

```
<221> NAME/KEY: misc_feature
<222> LOCATION: (943)..(943)
<223> OTHER INFORMATION: n = any nucleotide

<400> SEQUENCE: 31
tacaaacttt gccagcaaat ccacctcctg cctccaccaa tcgccagtca ggaaggcagc    60 ctacccgct  gtctccacct ttgagagaca ctcatcctca ggccatgcag tggaactcaa    120
caaccttcca ccaaactctg caagatccca gagtgaaagg cctgtatttc cctgctggtg   180
gctccagttc aggaacagta aaccctgttc cgactactgc ctctcactca tcgtcaatct   240
tctcgaggat tggggtccct gcgctgaaca tggagaacat cacatcagga ctcctaggac   300
cccttctcgt gttacaggcg gggttttttnt tgttgacaag aatcctcaca ataccgcaga   360
gtctagactc gtggtggact tctctcaatt ttcgaggggg gactaccgtg tgtcttggcc   420
aaaattcgca gtccccaacc tccaatcact caccaacctc ctgtcctcca acttgtcctg   480
gttatcgctg gatgtgtctg cggcgtttta tcatcttcct cttcatcctg ctgctatgcc   540
tcatcttctt gttggctcta ctggactgtc aaggtatgtt gcccgtttgt cctctaattc   600
caggatcctc aaccaccagc aggggaccat gccgaacctg cacgactcct gctcaaggaa   660
cctctacggt tccctcatgt tgctgtacca aaccttcgga cggaaattgc acctgtattc   720
ccatcccatc atcctgggct tcggaaaaat tcctatggga gtgggcctca gcccgtttct   780
catggctcag tttactagtg ccatttgttc agtggttcgt agggctttcc cccactgtct   840
ggcttttggt tatgtggatg atgtggtatt gggggccaag tctgtatcgc atcttgagtc   900
cctttttacc gctgttacca attttctttt gtctttgggt atncatttaa atcctaacaa   960
aacaaaaaga tggggttact ccctaca                                       987

<210> SEQ ID NO 32
<211> LENGTH: 350
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (309)..(309)
<223> OTHER INFORMATION: Xaa = any amino acid
<220> FEATURE:
<221> NAME/KEY: MISC_FEATURE
<222> LOCATION: (345)..(345)
<223> OTHER INFORMATION: Xaa = any amino acid

<400> SEQUENCE: 32
```

Ser Gly His Thr Thr Asn Phe Ala Ser Lys Ser Thr Ser Cys Leu His
1               5                   10                  15

Gln Ser Pro Val Arg Lys Ala Ala Tyr Pro Ala Val Ser Thr Phe Glu
            20                  25                  30

Arg His Ser Ser Gly His Ala Val Glu Leu Asn Asn Leu Pro Pro
        35                  40                  45

Asn Ser Ala Arg Ser Gln Ser Glu Arg Pro Val Phe Pro Cys Trp Trp
    50                  55                  60

Leu Gln Phe Arg Asn Ser Lys Pro Cys Ser Asp Tyr Cys Leu Ser Leu
65                  70                  75                  80

Ile Val Asn Leu Leu Glu Asp Trp Gly Pro Cys Ala Glu His Gly Glu
                85                  90                  95

His His Ile Arg Thr Pro Arg Thr Pro Ser Arg Val Thr Gly Gly Val
            100                 105                 110

```
Phe Leu Val Asp Lys Asn Pro His Asn Thr Ala Glu Ser Arg Leu Val
        115                 120                 125

Val Asp Phe Ser Gln Phe Ser Arg Gly Asp Tyr Arg Val Ser Trp Pro
    130                 135                 140

Lys Phe Ala Val Pro Asn Leu Gln Ser Leu Thr Asn Leu Leu Ser Ser
145                 150                 155                 160

Asn Leu Ser Trp Leu Ser Leu Asp Val Ser Ala Ala Phe Tyr His Leu
            165                 170                 175

Pro Leu His Pro Ala Ala Met Pro His Leu Leu Val Gly Ser Ser Gly
        180                 185                 190

Leu Ser Arg Tyr Val Ala Arg Leu Ser Ser Asn Ser Arg Ile Leu Asn
    195                 200                 205

His Gln His Gly Thr Met Pro Asn Leu His Asp Ser Cys Ser Arg Asn
210                 215                 220

Leu Tyr Gly Ser Leu Met Leu Tyr Gln Thr Phe Gly Arg Lys Leu
225                 230                 235                 240

His Leu Tyr Ser His Pro Ile Ile Leu Gly Phe Arg Lys Ile Pro Met
            245                 250                 255

Gly Val Gly Leu Ser Pro Phe Leu Leu Ala Gln Phe Thr Ser Ala Ile
        260                 265                 270

Cys Ser Val Val Arg Arg Ala Phe Pro His Cys Leu Ala Phe Ser Tyr
    275                 280                 285

Met Asp Asp Val Val Leu Gly Ala Lys Ser Val Ser His Leu Glu Ser
    290                 295                 300

Leu Phe Thr Ala Xaa Thr Asn Phe Leu Leu Ser Leu Gly Ile His Leu
305                 310                 315                 320

Asn Pro Asn Lys Thr Lys Arg Trp Gly Tyr Ser Leu His Phe Met Gly
            325                 330                 335

Tyr Val Ile Gly Cys His Gly Ser Xaa Pro Gln Glu His Ile
            340                 345                 350

<210> SEQ ID NO 33
<211> LENGTH: 181
<212> TYPE: PRT
<213> ORGANISM: artificial sequence
<220> FEATURE:
<223> OTHER INFORMATION: Synthetic peptide

<400> SEQUENCE: 33

Ser Asn Leu Ser Trp Leu Ser Leu Asp Val Ser Ala Ala Phe Tyr His
1               5                   10                  15

Leu Pro Leu His Pro Ala Ala Met Pro His Leu Leu Val Gly Ser Ser
            20                  25                  30

Gly Leu Ser Arg Tyr Val Ala Arg Leu Ser Ser Asn Ser Arg Ile Leu
        35                  40                  45

Asn His Gln Gln Gly Thr Met Pro Asn Leu His Asp Ser Cys Ser Arg
    50                  55                  60

Asn Leu Tyr Gly Ser Leu Met Leu Leu Tyr Gln Thr Phe Gly Arg Lys
65                  70                  75                  80

Leu His Leu Tyr Ser His Pro Ile Ile Leu Gly Phe Arg Lys Ile Pro
                85                  90                  95

Met Gly Val Gly Leu Ser Pro Phe Leu Met Ala Gln Phe Thr Ser Ala
            100                 105                 110

Ile Cys Ser Val Val Arg Arg Ala Phe Pro His Cys Leu Ala Phe Gly
        115                 120                 125
```

```
Tyr Val Asp Asp Val Val Leu Gly Ala Lys Ser Val Ser His Leu Glu
    130                 135                 140

Ser Leu Phe Thr Ala Val Thr Asn Phe Leu Leu Ser Leu Gly Ile His
145                 150                 155                 160

Leu Asn Pro Asn Lys Thr Lys Arg Trp Gly Tyr Ser Leu His Phe Met
                165                 170                 175

Gly Tyr Val Ile Gly
            180

<210> SEQ ID NO 34
<211> LENGTH: 340
<212> TYPE: PRT
<213> ORGANISM: artificial sequence
<220> FEATURE:
<223> OTHER INFORMATION: Synthetic peptide

<400> SEQUENCE: 34

Cys Pro Phe Cys Leu His Gln Ser Pro Val Arg Lys Ala Ala Tyr Pro
1               5                   10                  15

Ala Val Ser Thr Phe Glu Arg His Ser Ser Gly His Ala Val Glu
            20                  25                  30

Leu Asn Asn Leu Pro Pro Asn Ser Ala Arg Ser Gln Ser Glu Arg Pro
                35                  40                  45

Val Phe Pro Cys Trp Trp Leu Gln Phe Arg Asn Ser Lys Pro Cys Ser
    50                  55                  60

Asp Tyr Cys Leu Ser Leu Ile Val Asn Leu Leu Glu Asp Trp Gly Pro
65                  70                  75                  80

Cys Ala Glu His Gly Glu His His Ile Arg Thr Pro Arg Thr Pro Ser
                85                  90                  95

Arg Val Thr Gly Gly Val Phe Leu Val Asp Lys Asn Pro His Asn Thr
            100                 105                 110

Ala Glu Ser Arg Leu Val Val Asp Phe Ser Gln Phe Ser Arg Gly Asp
            115                 120                 125

Tyr Arg Val Ser Trp Pro Lys Phe Ala Val Pro Asn Leu Gln Ser Leu
    130                 135                 140

Thr Asn Leu Leu Ser Ser Asn Leu Ser Trp Leu Ser Leu Asp Val Ser
145                 150                 155                 160

Ala Ala Phe Tyr His Leu Pro Leu His Pro Ala Ala Met Pro His Leu
                165                 170                 175

Leu Val Gly Ser Ser Gly Leu Ser Arg Tyr Val Ala Arg Leu Ser Ser
            180                 185                 190

Asn Ser Arg Ile Leu Asn His Gln Gln Gly Thr Met Pro Asn Leu His
    195                 200                 205

Asp Ser Cys Ser Arg Asn Leu Tyr Gly Ser Leu Met Leu Leu Tyr Gln
    210                 215                 220

Thr Phe Gly Arg Lys Leu His Leu Tyr Ser His Pro Ile Ile Leu Gly
225                 230                 235                 240

Phe Arg Lys Ile Pro Met Gly Val Gly Leu Ser Pro Phe Leu Met Ala
                245                 250                 255

Gln Phe Thr Ser Ala Ile Cys Ser Val Val Arg Arg Ala Phe Pro His
            260                 265                 270

Cys Leu Ala Phe Gly Tyr Val Asp Asp Val Val Leu Gly Ala Lys Ser
            275                 280                 285

Val Ser His Leu Glu Ser Leu Phe Thr Ala Val Thr Asn Phe Leu Leu
    290                 295                 300
```

```
Ser Leu Gly Ile His Leu Asn Pro Asn Lys Thr Lys Arg Trp Gly Tyr
305                 310                 315                 320

Ser Leu His Phe Met Gly Tyr Val Ile Gly Cys His Gly Ser Leu Pro
                325                 330                 335

Gln Glu His Ile
            340

<210> SEQ ID NO 35
<211> LENGTH: 340
<212> TYPE: PRT
<213> ORGANISM: artificial sequence
<220> FEATURE:
<223> OTHER INFORMATION: Synthetic peptide

<400> SEQUENCE: 35

Ser Gly His Ile Thr Asn Ser Ala Ser Lys Ser Thr Ser Cys Leu His
1               5                   10                  15

Gln Ser Pro Val Arg Lys Ala Ala Tyr Pro Ala Val Ser Thr Phe Glu
                20                  25                  30

Arg His Ser Ser Gly His Ala Val Glu Leu Asn Asn Leu Pro Pro
                35                  40                  45

Asn Ser Ala Arg Ser Gln Ser Glu Arg Pro Val Phe Pro Cys Trp Trp
            50                  55                  60

Leu Gln Phe Arg Asn Ser Lys Pro Cys Ser Asp Tyr Cys Leu Ser Leu
65                  70                  75                  80

Ile Val Asn Leu Leu Glu Asp Trp Gly Pro Cys Ala Glu His Gly Glu
                85                  90                  95

His His Ile Arg Thr Pro Arg Thr Pro Ser Arg Val Thr Gly Gly Val
            100                 105                 110

Phe Leu Val Asp Lys Asn Pro His Asn Thr Ala Glu Ser Arg Leu Val
            115                 120                 125

Val Asp Phe Ser Gln Phe Ser Arg Gly Asp Tyr Arg Val Ser Trp Pro
130                 135                 140

Lys Phe Ala Val Pro Asn Leu Gln Ser Leu Thr Asn Leu Leu Ser Ser
145                 150                 155                 160

Asn Leu Ser Trp Leu Ser Leu Asp Val Ser Ala Ala Phe Tyr His Leu
                165                 170                 175

Pro Leu His Pro Ala Ala Met Pro His Leu Leu Val Gly Ser Ser Gly
            180                 185                 190

Leu Ser Arg Tyr Val Ala Arg Leu Ser Ser Asn Ser Arg Ile Leu Asn
            195                 200                 205

His Gln Gln Gly Thr Met Pro Asn Leu His Asp Ser Cys Ser Arg Asn
            210                 215                 220

Leu Tyr Gly Ser Leu Met Leu Leu Tyr Gln Thr Phe Gly Arg Lys Leu
225                 230                 235                 240

His Leu Tyr Ser His Pro Ile Ile Leu Gly Phe Arg Lys Ile Pro Met
                245                 250                 255

Gly Val Gly Leu Ser Pro Phe Leu Met Ala Gln Phe Thr Ser Ala Ile
            260                 265                 270

Cys Ser Val Val Arg Arg Ala Phe Pro His Cys Leu Ala Phe Gly Tyr
            275                 280                 285

Val Asp Asp Val Val Leu Gly Ala Lys Ser Val Ser His Leu Glu Ser
            290                 295                 300

Leu Phe Thr Ala Val Thr Asn Phe Leu Leu Ser Leu Gly Ile His Leu
305                 310                 315                 320
```

```
Asn Pro Asn Lys Thr Lys Arg Trp Gly Tyr Ser Leu His Phe Met Gly
            325                 330                 335
Tyr Val Ile Gly
        340

<210> SEQ ID NO 36
<211> LENGTH: 328
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (110)..(110)
<223> OTHER INFORMATION: Xaa = any amino acid
<220> FEATURE:
<221> NAME/KEY: MISC_FEATURE
<222> LOCATION: (314)..(314)
<223> OTHER INFORMATION: Xaa = any amino acid

<400> SEQUENCE: 36

Thr Asn Phe Ala Ser Lys Ser Thr Ser Cys Leu His Gln Ser Pro Val
1               5                   10                  15

Arg Lys Ala Ala Tyr Pro Ala Val Ser Thr Phe Glu Arg His Ser Ser
            20                  25                  30

Ser Gly His Ala Val Glu Leu Asn Asn Leu Pro Pro Asn Ser Ala Arg
        35                  40                  45

Ser Gln Ser Glu Arg Pro Val Phe Pro Cys Trp Trp Leu Gln Phe Arg
    50                  55                  60

Asn Ser Lys Pro Cys Ser Asp Tyr Cys Leu Ser Leu Ile Val Asn Leu
65                  70                  75                  80

Leu Glu Asp Trp Gly Pro Cys Ala Glu His Gly Glu His His Ile Arg
                85                  90                  95

Thr Pro Arg Thr Pro Ser Arg Val Thr Gly Gly Val Phe Xaa Val Asp
            100                 105                 110

Lys Asn Pro His Asn Thr Ala Glu Ser Arg Leu Val Val Asp Phe Ser
            115                 120                 125

Gln Phe Ser Arg Gly Asp Tyr Arg Val Ser Trp Pro Lys Phe Ala Val
    130                 135                 140

Pro Asn Leu Gln Ser Leu Thr Asn Leu Leu Ser Ser Asn Leu Ser Trp
145                 150                 155                 160

Leu Ser Leu Asp Val Ser Ala Ala Phe Tyr His Leu Pro Leu His Pro
                165                 170                 175

Ala Ala Met Pro His Leu Leu Val Gly Ser Thr Gly Leu Ser Arg Tyr
            180                 185                 190

Val Ala Arg Leu Ser Ser Asn Ser Arg Ile Leu Asn His Gln Gln Gly
        195                 200                 205

Thr Met Pro Asn Leu His Asp Ser Cys Ser Arg Asn Leu Tyr Gly Ser
    210                 215                 220

Leu Met Leu Leu Tyr Gln Thr Phe Gly Arg Lys Leu His Leu Tyr Ser
225                 230                 235                 240

His Pro Ile Ile Leu Gly Phe Arg Lys Ile Pro Met Gly Val Gly Leu
                245                 250                 255

Ser Pro Phe Leu Met Ala Gln Phe Thr Ser Ala Ile Cys Ser Val Val
            260                 265                 270

Arg Arg Ala Phe Pro His Cys Leu Ala Phe Gly Tyr Val Asp Asp Val
        275                 280                 285

Val Leu Gly Ala Lys Ser Val Ser His Leu Glu Ser Leu Phe Thr Ala
```

```
            290                 295                 300
Val Thr Asn Phe Leu Leu Ser Leu Gly Xaa His Leu Asn Pro Asn Lys
305                 310                 315                 320

Thr Lys Arg Trp Gly Tyr Ser Leu
                325

<210> SEQ ID NO 37
<211> LENGTH: 197
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (187)..(187)
<223> OTHER INFORMATION: Xaa = any amino acid

<400> SEQUENCE: 37

Gln Ser Leu Asp Ser Trp Trp Thr Ser Leu Asn Phe Arg Gly Gly Thr
1               5                   10                  15

Thr Val Cys Leu Gly Gln Asn Ser Gln Ser Pro Thr Ser Asn His Ser
                20                  25                  30

Pro Thr Ser Cys Pro Pro Thr Cys Pro Gly Tyr Arg Trp Met Cys Leu
            35                  40                  45

Arg Arg Phe Ile Ile Phe Leu Phe Ile Leu Leu Leu Cys Leu Ile Phe
50                  55                  60

Leu Leu Val Leu Leu Asp Cys Gln Gly Met Leu Pro Val Cys Pro Leu
65                  70                  75                  80

Ile Pro Gly Ser Ser Thr Thr Ser Thr Gly Pro Cys Arg Thr Cys Thr
                85                  90                  95

Thr Pro Ala Gln Gly Thr Ser Thr Val Pro Ser Cys Cys Cys Thr Lys
            100                 105                 110

Pro Ser Asp Gly Asn Cys Thr Cys Ile Pro Ile Pro Ser Ser Trp Ala
        115                 120                 125

Phe Gly Lys Phe Leu Trp Glu Trp Ala Ser Ala Arg Phe Ser Trp Leu
    130                 135                 140

Ser Leu Leu Val Pro Phe Val Gln Trp Phe Val Gly Leu Ser Pro Thr
145                 150                 155                 160

Val Trp Leu Leu Val Ile Trp Met Met Trp Tyr Trp Gly Pro Ser Leu
                165                 170                 175

Tyr Arg Ile Leu Ser Pro Phe Leu Pro Leu Xaa Pro Ile Phe Phe Cys
            180                 185                 190

Leu Trp Val Tyr Ile
        195

<210> SEQ ID NO 38
<211> LENGTH: 161
<212> TYPE: PRT
<213> ORGANISM: artificial sequence
<220> FEATURE:
<223> OTHER INFORMATION: Synthetic peptide

<400> SEQUENCE: 38

Pro Pro Thr Cys Pro Gly Tyr Arg Trp Met Cys Leu Arg Arg Phe Ile
1               5                   10                  15

Ile Phe Leu Phe Ile Leu Leu Leu Cys Leu Ile Phe Leu Leu Val Leu
                20                  25                  30

Leu Asp Cys Gln Gly Met Leu Pro Val Cys Pro Leu Ile Pro Gly Ser
            35                  40                  45
```

```
Ser Thr Thr Ser Arg Gly Pro Cys Arg Thr Cys Thr Thr Pro Ala Gln
     50                  55                  60

Gly Thr Ser Thr Val Pro Ser Cys Cys Cys Thr Lys Pro Ser Asp Gly
 65                  70                  75                  80

Asn Cys Thr Cys Ile Pro Ile Pro Ser Ser Trp Ala Phe Gly Lys Phe
                 85                  90                  95

Leu Trp Glu Trp Ala Ser Ala Arg Phe Ser Trp Leu Ser Leu Leu Val
                100                 105                 110

Pro Phe Val Gln Trp Phe Val Gly Leu Ser Pro Thr Val Trp Leu Leu
                115                 120                 125

Val Met Trp Met Met Trp Tyr Trp Gly Pro Ser Leu Tyr Arg Ile Leu
            130                 135                 140

Ser Pro Phe Leu Pro Leu Leu Pro Ile Phe Phe Cys Leu Trp Val Tyr
145                 150                 155                 160

Ile

<210> SEQ ID NO 39
<211> LENGTH: 160
<212> TYPE: PRT
<213> ORGANISM: artificial sequence
<220> FEATURE:
<223> OTHER INFORMATION: Synthetic peptide

<400> SEQUENCE: 39

Pro Thr Cys Pro Gly Tyr Arg Trp Met Cys Leu Arg Arg Phe Ile Ile
  1               5                  10                  15

Phe Leu Phe Ile Leu Leu Leu Cys Leu Ile Phe Leu Leu Val Leu Leu
                 20                  25                  30

Asp Cys Gln Gly Met Leu Pro Val Cys Pro Leu Ile Pro Gly Ser Ser
             35                  40                  45

Thr Thr Ser Arg Gly Pro Cys Arg Thr Cys Thr Thr Pro Ala Gln Gly
     50                  55                  60

Thr Ser Thr Val Pro Ser Cys Cys Cys Thr Lys Pro Ser Asp Gly Asn
 65                  70                  75                  80

Cys Thr Cys Ile Pro Ile Pro Ser Ser Trp Ala Phe Gly Lys Phe Leu
                 85                  90                  95

Trp Glu Trp Ala Ser Ala Arg Phe Ser Trp Leu Ser Leu Leu Val Pro
                100                 105                 110

Phe Val Gln Trp Phe Val Gly Leu Ser Pro Thr Val Trp Leu Leu Val
                115                 120                 125

Met Trp Met Met Trp Tyr Trp Gly Pro Ser Leu Tyr Arg Ile Leu Ser
            130                 135                 140

Pro Phe Leu Pro Leu Leu Pro Ile Phe Phe Cys Leu Trp Val Tyr Ile
145                 150                 155                 160

<210> SEQ ID NO 40
<211> LENGTH: 325
<212> TYPE: PRT
<213> ORGANISM: artificial sequence
<220> FEATURE:
<223> OTHER INFORMATION: Synthetic peptide

<400> SEQUENCE: 40

Leu Gly Ser Pro Gln Ala Gln Gly Ile Leu Gln Thr Leu Pro Ala Asn
  1               5                  10                  15

Pro Pro Pro Ala Ser Thr Asn Arg Gln Ser Gly Arg Gln Pro Thr Pro
                 20                  25                  30
```

```
Leu Ser Pro Pro Leu Arg Asp Thr His Pro Gln Ala Met Gln Trp Asn
            35                  40                  45

Ser Thr Thr Phe His Gln Thr Leu Gln Asp Pro Arg Val Lys Gly Leu
 50                  55                  60

Tyr Phe Pro Ala Gly Gly Ser Ser Gly Thr Val Asn Pro Val Pro
 65                  70                  75                  80

Thr Thr Ala Ser His Ser Ser Ile Phe Ser Arg Ile Gly Val Pro
                85                  90                  95

Ala Leu Asn Met Glu Asn Ile Thr Ser Gly Leu Leu Gly Pro Leu Leu
            100                 105                 110

Val Leu Gln Ala Gly Phe Phe Leu Leu Thr Arg Ile Leu Thr Ile Pro
            115                 120                 125

Gln Ser Leu Asp Ser Trp Trp Thr Ser Leu Asn Phe Arg Gly Gly Thr
            130                 135                 140

Thr Val Cys Leu Gly Gln Asn Ser Gln Ser Pro Thr Ser Asn His Ser
145                 150                 155                 160

Pro Thr Ser Cys Pro Pro Thr Cys Pro Gly Tyr Arg Trp Met Cys Leu
                165                 170                 175

Arg Arg Phe Ile Ile Phe Leu Phe Ile Leu Leu Leu Cys Leu Ile Phe
                180                 185                 190

Leu Leu Val Leu Leu Asp Cys Gln Gly Met Leu Pro Val Cys Pro Leu
            195                 200                 205

Ile Pro Gly Ser Ser Thr Thr Ser Arg Gly Pro Cys Arg Thr Cys Thr
210                 215                 220

Thr Pro Ala Gln Gly Thr Ser Thr Val Pro Ser Cys Cys Cys Thr Lys
225                 230                 235                 240

Pro Ser Asp Gly Asn Cys Thr Cys Ile Pro Ile Pro Ser Ser Trp Ala
                245                 250                 255

Phe Gly Lys Phe Leu Trp Glu Trp Ala Ser Ala Arg Phe Ser Trp Leu
            260                 265                 270

Ser Leu Leu Val Pro Phe Val Gln Trp Phe Val Gly Leu Ser Pro Thr
            275                 280                 285

Val Trp Leu Leu Val Met Trp Met Met Trp Tyr Trp Gly Pro Ser Leu
            290                 295                 300

Tyr Arg Ile Leu Ser Pro Phe Leu Pro Leu Leu Pro Ile Phe Phe Cys
305                 310                 315                 320

Leu Trp Val Tyr Ile
            325

<210> SEQ ID NO 41
<211> LENGTH: 309
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (308)..(308)
<223> OTHER INFORMATION: Xaa = any amino acid

<400> SEQUENCE: 41

Pro Pro Pro Ala Ser Thr Asn Arg Gln Ser Gly Arg Gln Pro Thr Pro
1               5                   10                  15

Leu Ser Pro Pro Leu Arg Asp Thr His Pro Gln Ala Met Gln Trp Asn
            20                  25                  30

Ser Thr Thr Phe His Gln Thr Leu Gln Asp Pro Arg Val Lys Gly Leu
```

```
                35                  40                  45
Tyr Phe Pro Ala Gly Gly Ser Ser Gly Thr Val Asn Pro Val Pro
         50                  55                  60
Thr Thr Ala Ser His Ser Ser Ile Phe Ser Arg Ile Gly Val Pro
65                  70                  75                  80
Ala Leu Asn Met Glu Asn Ile Thr Ser Gly Leu Leu Gly Pro Leu Leu
                 85                  90                  95
Val Leu Gln Ala Gly Phe Phe Leu Leu Thr Arg Ile Leu Thr Ile Pro
                100                 105                 110
Gln Ser Leu Asp Ser Trp Trp Thr Ser Leu Asn Phe Arg Gly Gly Thr
                115                 120                 125
Thr Val Cys Leu Gly Gln Asn Ser Gln Ser Pro Thr Ser Asn His Ser
    130                 135                 140
Pro Thr Ser Cys Pro Pro Thr Cys Pro Gly Tyr Arg Trp Met Cys Leu
145                 150                 155                 160
Arg Arg Phe Ile Ile Phe Leu Phe Ile Leu Leu Leu Cys Leu Ile Phe
                165                 170                 175
Leu Leu Ala Leu Leu Asp Cys Gln Gly Met Leu Pro Val Cys Pro Leu
            180                 185                 190
Ile Pro Gly Ser Ser Thr Thr Ser Arg Gly Pro Cys Arg Thr Cys Thr
                195                 200                 205
Thr Pro Ala Gln Gly Thr Ser Thr Val Pro Ser Cys Cys Cys Thr Lys
        210                 215                 220
Pro Ser Asp Gly Asn Cys Thr Cys Ile Pro Ile Pro Ser Ser Trp Ala
225                 230                 235                 240
Phe Gly Lys Phe Leu Trp Glu Trp Ala Ser Ala Arg Phe Ser Trp Leu
                245                 250                 255
Ser Leu Leu Val Pro Phe Val Gln Trp Phe Val Gly Leu Ser Pro Thr
            260                 265                 270
Val Trp Leu Leu Val Met Trp Met Met Trp Tyr Trp Gly Pro Ser Leu
        275                 280                 285
Tyr Arg Ile Leu Ser Pro Phe Leu Pro Leu Leu Pro Ile Phe Phe Cys
    290                 295                 300
Leu Trp Val Xaa Ile
305

<210> SEQ ID NO 42
<211> LENGTH: 1031
<212> TYPE: DNA
<213> ORGANISM: artificial sequence
<220> FEATURE:
<223> OTHER INFORMATION: Synthetic oligonucleotide

<400> SEQUENCE: 42
tactacaaac cttgccagca atccgcctc ctgcctctac caatcgccag tcaggaaggc      60
agcctacccc tctgactcca cctttgagaa cactcatcc tcaggccatg cagtggaact     120
ccacaaactt ccaccgaact ctacaagatc cagagtgaa aggcctgtat ctccctgctg     180
gtggctccag ttcaggaaca gtaaaccctg ttccgactac tgtctctcac acatcgtcaa     240
tcttatcgag gattgggggac cctgcactga acatggagaa catcacatca ggattcctag     300
gacccctgct cgtgttacag gcggggtttt tcttgttgac aagaatcctc acaataccgc     360
agagtctaga ctcgtggtgg acttctctca attttctagg ggggaccacc gtgtgccttg     420
gccaaaattc gcagtcccca acctccaatc actcaccaac ctcctgtcct ccaacttgtc     480
```

-continued

```
ctggttatcg ctggatgtgt ctgcggcgtt ttatcatatt cctcttcatc ctgctgctat    540
gcctcatctt cttgttggtt cttctggact atcaaggtat gttgcccgtt tgccctctaa    600
ttccaggatc ctcaaccacc agcacgggac catgcagaac ctgcacgact cctgctcaag    660
gaacctctwt gtatccctca tgttgctgta ccaaacctwc ggmcgsaaat tgcacctgta    720
ttcccatccc atcatcctgg gctttcggaa aattcctatg ggagtgggcc tcagcccgtt    780
tctcctgact cagtttacta gtgccatttg ttcagtggtt cgtagggctt ccccccactg    840
tttggctttc agttatatgg atgatgtggt attgggggcc aggtctgtac agcatcgtga    900 ggccctttt  accgctgtta ccaatttct  tttgtctctg gtatacatt  taaccccgga    960 caaaacaaaa agatggggtt actctttaca tttcatgggc tatgtcattg gatgttatgg   1020
gtcattgcca c                                                       1031
```

<210> SEQ ID NO 43
<211> LENGTH: 345
<212> TYPE: PRT
<213> ORGANISM: artificial sequence
<220> FEATURE:
<223> OTHER INFORMATION: Synthetic peptide

<400> SEQUENCE: 43

```
Thr Thr Asn Leu Ala Ser Lys Ser Ala Ser Cys Leu Tyr Gln Ser Pro
1               5                   10                  15

Val Arg Lys Ala Ala Tyr Pro Ser Asp Ser Thr Phe Glu Lys His Ser
            20                  25                  30

Ser Ser Gly His Ala Val Glu Leu His Lys Leu Pro Pro Asn Ser Thr
        35                  40                  45

Arg Ser Gln Ser Glu Arg Pro Val Ser Pro Cys Trp Trp Leu Gln Phe
    50                  55                  60

Arg Asn Ser Lys Pro Cys Ser Asp Tyr Cys Leu Ser His Ile Val Asn
65                  70                  75                  80

Leu Ile Glu Asp Trp Gly Pro Cys Thr Glu His Gly Glu His His Ile
                85                  90                  95

Arg Ile Pro Arg Thr Pro Ala Arg Val Thr Gly Gly Val Phe Leu Val
            100                 105                 110

Asp Lys Asn Pro His Asn Thr Ala Glu Ser Arg Leu Val Val Asp Phe
        115                 120                 125

Ser Gln Phe Ser Arg Gly Asp His Arg Val Pro Trp Pro Lys Phe Ala
    130                 135                 140

Val Pro Asn Leu Gln Ser Leu Thr Asn Leu Leu Ser Ser Asn Leu Ser
145                 150                 155                 160

Trp Leu Ser Leu Asp Val Ser Ala Ala Phe Tyr His Ile Pro Leu His
                165                 170                 175

Pro Ala Ala Met Pro His Leu Leu Val Gly Ser Ser Gly Leu Ser Arg
            180                 185                 190

Tyr Val Ala Arg Leu Pro Ser Asn Ser Arg Ile Leu Asn His Gln His
        195                 200                 205

Gly Thr Met Gln Asn Leu His Asp Ser Cys Ser Arg Asn Leu Tyr Phe
    210                 215                 220

Val Ser Leu Met Leu Leu Tyr Gln Thr Phe Thr Gly Arg Lys Leu His
225                 230                 235                 240

Leu Tyr Ser His Pro Ile Ile Leu Gly Phe Arg Lys Ile Pro Met Gly
                245                 250                 255

Val Gly Leu Ser Pro Phe Leu Leu Thr Gln Phe Thr Ser Ala Ile Cys
```

```
                   260                 265                 270
Ser Val Val Arg Arg Ala Phe Pro His Cys Leu Ala Phe Ser Tyr Met
                275                 280                 285

Asp Asp Val Val Leu Gly Ala Arg Ser Val Gln His Arg Glu Ala Leu
            290                 295                 300

Phe Thr Ala Val Thr Asn Phe Leu Leu Ser Leu Gly Ile His Leu Thr
305                 310                 315                 320

Pro Asp Lys Thr Lys Arg Trp Gly Tyr Ser Leu His Phe Met Gly Tyr
                325                 330                 335

Val Ile Gly Cys Tyr Gly Ser Leu Pro
            340                 345

<210> SEQ ID NO 44
<211> LENGTH: 317
<212> TYPE: PRT
<213> ORGANISM: artificial sequence
<220> FEATURE:
<223> OTHER INFORMATION: Synthetic peptide

<400> SEQUENCE: 44

Leu Gln Thr Leu Pro Ala Asn Pro Pro Ala Ser Thr Asn Arg Gln
1               5                  10                  15

Ser Gly Arg Gln Pro Thr Pro Leu Thr Pro Leu Arg Asn Thr His
            20                  25                  30

Pro Gln Ala Met Gln Trp Asn Ser Thr Asn Phe His Arg Thr Leu Gln
        35                  40                  45

Asp Pro Arg Val Lys Gly Leu Tyr Leu Pro Ala Gly Gly Ser Ser Ser
    50                  55                  60

Gly Thr Val Asn Pro Val Pro Thr Thr Val Ser His Thr Ser Ser Ile
65                  70                  75                  80

Leu Ser Arg Ile Gly Asp Pro Ala Leu Asn Met Glu Asn Ile Thr Ser
                85                  90                  95

Gly Phe Leu Gly Pro Leu Leu Val Leu Gln Ala Gly Phe Phe Leu Leu
            100                 105                 110

Thr Arg Ile Leu Thr Ile Pro Gln Ser Leu Asp Ser Trp Trp Thr Ser
        115                 120                 125

Leu Asn Phe Leu Gly Gly Thr Thr Val Cys Leu Gly Gln Asn Ser Gln
130                 135                 140

Ser Pro Thr Ser Asn His Ser Pro Thr Ser Cys Pro Pro Thr Cys Pro
145                 150                 155                 160

Gly Tyr Arg Trp Met Cys Leu Arg Arg Phe Ile Ile Phe Leu Phe Ile
                165                 170                 175

Leu Leu Leu Cys Leu Ile Phe Leu Leu Val Leu Leu Asp Tyr Gln Gly
            180                 185                 190

Met Leu Pro Val Cys Pro Leu Ile Pro Gly Ser Ser Thr Thr Ser Thr
        195                 200                 205

Gly Pro Cys Arg Thr Cys Thr Thr Pro Ala Gln Gly Thr Ser Met Leu
    210                 215                 220

Tyr Pro Ser Cys Cys Cys Thr Lys Pro Ser Thr Ala Ala Asn Cys Thr
225                 230                 235                 240

Cys Ile Pro Ile Pro Ser Ser Trp Ala Phe Gly Lys Phe Leu Trp Glu
                245                 250                 255

Trp Ala Ser Ala Arg Phe Ser Leu Ser Leu Leu Val Pro Phe Val Gln
            260                 265                 270

Trp Phe Val Gly Leu Ser Pro Thr Val Trp Leu Ser Val Ile Trp Met
```

```
                275                 280                 285
Met Trp Tyr Trp Gly Pro Gly Leu Tyr Ser Ile Val Arg Pro Phe Leu
    290                 295                 300

Pro Leu Leu Pro Ile Phe Phe Cys Leu Trp Val Tyr Ile
305                 310                 315

<210> SEQ ID NO 45
<211> LENGTH: 888
<212> TYPE: DNA
<213> ORGANISM: artificial sequence
<220> FEATURE:
<223> OTHER INFORMATION: Synthetic oligonucleotide

<400> SEQUENCE: 45
tggtcacagt gccaacagtt cctcctcctg cctccaccaa tcggcagtca gggaggcagc      60
ctactcccat ctctccacct ctaagagaca gtcatcctca ggccatggtg gctcagcctg     120
ctggtggctc cagttcagga acactcaacc ctgttcccaa tattgcctct cacatctcgt     180
caatctcctt gaggactggg gaccctgcgc cgaacatgga gaacatcaca tcaggattcc     240 taggaccccct gctcgtgtta caggcggggt ttttcttgtt gacaagaatc ctcacaatac     300
cgcagagtct agactcgtgg tggacttctc tcagttttct aggggatca cccgtgtgtc      360 ttggccaaaa ttcgcagtcc ccaacctcca atcactcacc aacctcctgt cctccaattt     420
gacctggtta tcgctggata tgtctgcggc gttttatcat attcctcttc atcctgccgc     480
tatgcctcat cttcttattg gttcttctgg attatcaagg tatgttgccc gtttgtcctc     540
taattccagg atccacaaca accagtgcgg gaccctgcaa aacctgcacg actcctgctc     600
aaggcaactc tatgttccc tcatgttgct gtacaaaacc tacggatgga aattgcacct     660
gtattcccat cccatcatct tgggctttcg caaaatacct atgggagtgg gcctcagtcc     720
gtttctcttg gctcagtta ctagtgccat ttgttcagtg attcgtaggg ctttcccca       780 ctgtttggct ttcagctata ttgatgatgt ggtactgggg gccaagtctg cacaacatct     840
tgagtccctt tataccgctg ttaccaattt tcttttgtct ttgggtat                  888

<210> SEQ ID NO 46
<211> LENGTH: 295
<212> TYPE: PRT
<213> ORGANISM: artificial sequence
<220> FEATURE:
<223> OTHER INFORMATION: Synthetic peptide

<400> SEQUENCE: 46

Gly His Ser Ala Asn Ser Ser Ser Cys Leu His Gln Ser Ala Val
1               5                   10                  15

Arg Glu Ala Ala Tyr Ser His Leu Ser Thr Ser Lys Arg Gln Ser Ser
                20                  25                  30

Ser Gly His Gly Gly Ser Ala Cys Trp Trp Leu Gln Phe Arg Asn Thr
            35                  40                  45

Gln Pro Cys Ser Gln Tyr Cys Leu Ser His Leu Val Asn Leu Leu Glu
        50                  55                  60

Asp Trp Gly Pro Cys Ala Glu His Gly Glu His His Ile Arg Ile Pro
65                  70                  75                  80

Arg Thr Pro Ala Arg Val Thr Gly Gly Val Phe Leu Val Asp Lys Asn
                85                  90                  95

Pro His Asn Thr Ala Glu Ser Arg Leu Val Val Asp Phe Ser Gln Phe
                100                 105                 110
```

```
Ser Arg Gly Ile Thr Arg Val Ser Trp Pro Lys Phe Ala Val Pro Asn
        115                 120                 125

Leu Gln Ser Leu Thr Asn Leu Leu Ser Ser Asn Leu Thr Trp Leu Ser
    130                 135                 140

Leu Asp Met Ser Ala Ala Phe Tyr His Ile Pro Leu His Pro Ala Ala
145                 150                 155                 160

Met Pro His Leu Leu Ile Gly Ser Ser Gly Leu Ser Arg Tyr Val Ala
                165                 170                 175

Arg Leu Ser Ser Asn Ser Arg Ile His Asn Asn Gln Cys Gly Thr Leu
                180                 185                 190

Gln Asn Leu His Asp Ser Cys Ser Arg Gln Leu Tyr Val Ser Leu Met
            195                 200                 205

Leu Leu Tyr Lys Thr Tyr Gly Trp Lys Leu His Leu Tyr Ser His Pro
    210                 215                 220

Ile Ile Leu Gly Phe Arg Lys Ile Pro Met Gly Val Gly Leu Ser Pro
225                 230                 235                 240

Phe Leu Leu Ala Gln Phe Thr Ser Ala Ile Cys Ser Val Ile Arg Arg
                245                 250                 255

Ala Phe Pro His Cys Leu Ala Phe Ser Tyr Ile Asp Asp Val Val Leu
                260                 265                 270

Gly Ala Lys Ser Ala Gln His Leu Glu Ser Leu Tyr Thr Ala Val Thr
            275                 280                 285

Asn Phe Leu Leu Ser Leu Gly
    290                 295

<210> SEQ ID NO 47
<211> LENGTH: 293
<212> TYPE: PRT
<213> ORGANISM: artificial sequence
<220> FEATURE:
<223> OTHER INFORMATION: Synthetic peptide

<400> SEQUENCE: 47

Val Thr Val Pro Thr Val Pro Pro Ala Ser Thr Asn Arg Gln Ser
1               5                   10                  15

Gly Arg Gln Pro Thr Pro Ile Ser Pro Pro Leu Arg Asp Ser His Pro
                20                  25                  30

Gln Ala Met Val Ala Gln Pro Ala Gly Gly Ser Ser Ser Gly Thr Leu
            35                  40                  45

Asn Pro Val Pro Asn Ile Ala Ser His Ile Ser Ser Ile Ser Leu Arg
        50                  55                  60

Thr Gly Asp Pro Ala Pro Asn Met Glu Asn Ile Thr Ser Gly Phe Leu
65                  70                  75                  80

Gly Pro Leu Leu Val Leu Gln Ala Gly Phe Phe Leu Leu Thr Arg Ile
                85                  90                  95

Leu Thr Ile Pro Gln Ser Leu Asp Ser Trp Trp Thr Ser Leu Ser Phe
            100                 105                 110

Leu Gly Gly Ser Pro Val Cys Leu Gly Gln Asn Ser Gln Ser Pro Thr
        115                 120                 125

Ser Asn His Ser Pro Thr Ser Cys Pro Pro Ile Pro Gly Tyr Arg Trp
    130                 135                 140

Ile Cys Leu Arg Arg Phe Ile Ile Phe Leu Phe Ile Leu Pro Leu Cys
145                 150                 155                 160

Leu Ile Phe Leu Leu Val Leu Leu Asp Tyr Gln Gly Met Leu Pro Val
                165                 170                 175
```

```
Cys Pro Leu Ile Pro Gly Ser Thr Thr Thr Ser Ala Gly Pro Cys Lys
                180                 185                 190

Thr Cys Thr Thr Pro Ala Gln Gly Asn Ser Met Phe Pro Ser Cys Cys
            195                 200                 205

Cys Thr Lys Pro Thr Asp Gly Asn Cys Thr Cys Ile Pro Ile Pro Ser
    210                 215                 220

Ser Trp Ala Phe Ala Lys Tyr Leu Trp Glu Trp Ala Ser Val Arg Phe
225                 230                 235                 240

Ser Trp Leu Ser Leu Leu Val Pro Phe Val Gln Phe Val Gly Leu Ser
                245                 250                 255

Pro Thr Val Trp Leu Ser Ala Ile Leu Met Met Trp Tyr Trp Gly Pro
                260                 265                 270

Ser Leu His Asn Ile Leu Ser Pro Phe Ile Pro Leu Leu Pro Ile Phe
                275                 280                 285

Phe Cys Leu Trp Val
                290

<210> SEQ ID NO 48
<211> LENGTH: 591
<212> TYPE: DNA
<213> ORGANISM: artificial sequence
<220> FEATURE:
<223> OTHER INFORMATION: Synthetic oligonucleotide

<400> SEQUENCE: 48
tcctgtcctc caatttgtcc tggttatcgc tggatgtgtc tgcggcgttt tatgatattc      60
ctcttcatcc tgctgctatg cctcatcttc ttattggttc ttctggatta tcaaggtatg     120
ttgcccgtct gtcctctaat tccaggatca acaacaacca gtacgggacc atgcaaaacc     180
aaaacctgca cgactcctgc tcaaggcaac tctatgtttc cctcatgttg ctgtacaaaa     240
cctacggatg gaaattgcac ctgtattccc atcccatcgt cctgggcttt cgcaaaattc     300
ctatgggagt gggcctcagt ccgtttctct ggctcagtt tactagtgcc atttgttcag     360
tggttcgtag gcttttcccc cactgtttgg ctttcagcta tggatgat gtggtattgg      420 gggccaagtc tgtacagcat cgtgaggccc tttatacagc tgttaccaat tttcttttgt     480
ctctgggtat acatttaaac cctaacaaaa caaaaagatg gggttattcc ctaaacttca     540
tgggttacat aattggaagt tggggaacat tgccacagga tcatattgta c              591

<210> SEQ ID NO 49
<211> LENGTH: 186
<212> TYPE: PRT
<213> ORGANISM: artificial sequence
<220> FEATURE:
<223> OTHER INFORMATION: Synthetic peptide

<400> SEQUENCE: 49

Ser Asn Leu Ser Trp Leu Ser Leu Asp Val Ser Ala Ala Phe Tyr Asp
1               5                  10                  15

Ile Pro Leu His Pro Ala Ala Met Pro His Leu Leu Ile Gly Ser Ser
                20                  25                  30

Gly Leu Ser Arg Tyr Val Ala Arg Leu Ser Ser Asn Ser Arg Ile Asn
            35                  40                  45

Asn Asn Gln Tyr Gly Thr Met Gln Asn Gln Asn Leu His Asp Ser Cys
    50                  55                  60

Ser Arg Gln Leu Tyr Val Ser Leu Met Leu Leu Tyr Lys Thr Tyr Gly
65                  70                  75                  80
```

Trp Lys Leu His Leu Tyr Ser His Pro Ile Val Leu Gly Phe Arg Lys
                85                  90                  95

Ile Pro Met Gly Val Gly Leu Ser Pro Phe Leu Leu Ala Gln Phe Thr
            100                 105                 110

Ser Ala Ile Cys Ser Val Val Arg Arg Ala Phe Pro His Cys Leu Ala
        115                 120                 125

Phe Ser Tyr Met Asp Asp Val Val Leu Gly Ala Lys Ser Val Gln His
    130                 135                 140

Arg Glu Ala Leu Tyr Thr Ala Val Thr Asn Phe Leu Leu Ser Leu Gly
145                 150                 155                 160

Ile His Leu Asn Pro Asn Lys Thr Lys Arg Trp Gly Tyr Ser Leu Asn
                165                 170                 175

Phe Met Gly Tyr Ile Ile Gly Ser Trp Gly
                180                 185

<210> SEQ ID NO 50
<211> LENGTH: 165
<212> TYPE: PRT
<213> ORGANISM: artificial sequence
<220> FEATURE:
<223> OTHER INFORMATION: Synthetic peptide

<400> SEQUENCE: 50

Ser Cys Pro Pro Ile Cys Pro Gly Tyr Arg Trp Met Cys Leu Arg Arg
1               5                   10                  15

Phe Met Ile Phe Leu Phe Ile Leu Leu Leu Cys Leu Ile Phe Leu Leu
            20                  25                  30

Val Leu Leu Asp Tyr Gln Gly Met Leu Pro Val Cys Pro Leu Ile Pro
        35                  40                  45

Gly Ser Thr Thr Thr Ser Thr Gly Pro Cys Lys Thr Cys Thr Thr
    50                  55                  60

Thr Pro Ala Gln Gly Asn Ser Met Phe Pro Ser Cys Cys Cys Thr Lys
65                  70                  75                  80

Pro Thr Asp Gly Asn Cys Thr Cys Ile Pro Ile Pro Ser Ser Trp Ala
                85                  90                  95

Phe Ala Lys Phe Leu Trp Glu Trp Ala Ser Val Arg Phe Ser Trp Leu
            100                 105                 110

Ser Leu Leu Val Pro Phe Val Gln Trp Phe Val Gly Leu Ser Pro Thr
        115                 120                 125

Val Trp Leu Ser Ala Ile Trp Met Met Trp Tyr Trp Gly Pro Ser Leu
    130                 135                 140

Tyr Ser Ile Val Arg Pro Phe Ile Gln Leu Leu Pro Ile Phe Phe Cys
145                 150                 155                 160

Leu Trp Val Tyr Ile
                165

<210> SEQ ID NO 51
<211> LENGTH: 669
<212> TYPE: DNA
<213> ORGANISM: artificial sequence
<220> FEATURE:
<223> OTHER INFORMATION: Synthetic oligonucleotide

<400> SEQUENCE: 51
aatcctcaca ataccgcaga gtctagactt cgtggtgact tctctcaatt ttctagggga      60
ccacccgtgt gtcttggcca aaattcgcag tccccaacct ccaatcactc accaacctct    120
tgtcctccaa tttgtcctgg ttatcgctgg atgtgtctgc ggcgttttat catatccctc    180

-continued

```
ttcatcctgc tgctatgcct catcttctta ttggttcttc tggattatca aggtatgttg      240
cccgtttgtc ctctaattcc aggatccaca acaaccagta cgggaccctg caaaacctgc      300
acgactcctg ctcaaggcaa ctctatgttt ccctcatgtt gctgtacaaa acctacggat      360
ggaaattgca cmtgtattcc catcccatca tcttgggctt tcgcaaaata ccctatggag      420
tgggcctcag tccgtttctc ttggttcagt ttactagtgc catttgttca gtggttcgta      480
gggctttccc ccactgtttg gctttcagct atatggatga tattgtactg ggggccaagt      540
ctgtacaaca tcttgagtcc ctttataccg ctgttaccaa ttttcttttg tctttgggta      600
tacatttaac ccctaacaaa acaaagagat ggggttattc cctgaatttc atgggttatg      660
taattggaa                                                              669
```

<210> SEQ ID NO 52
<211> LENGTH: 181
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (83)..(83)
<223> OTHER INFORMATION: Xaa = any amino acid

<400> SEQUENCE: 52

```
Ser Asn Leu Ser Trp Leu Ser Leu Asp Val Ser Ala Ala Phe Tyr His
1               5                   10                  15

Ile Pro Leu His Pro Ala Ala Met Pro His Leu Leu Ile Gly Ser Ser
            20                  25                  30

Gly Leu Ser Arg Tyr Val Ala Arg Leu Ser Ser Asn Ser Arg Ile His
        35                  40                  45

Asn Asn Gln Tyr Gly Thr Leu Gln Asn Leu His Asp Ser Cys Ser Arg
    50                  55                  60

Gln Leu Tyr Val Ser Leu Met Leu Leu Tyr Lys Thr Tyr Gly Trp Lys
65                  70                  75                  80

Leu His Xaa Tyr Ser His Pro Ile Ile Leu Gly Phe Arg Lys Ile Pro
                85                  90                  95

Met Gly Val Gly Leu Ser Pro Phe Leu Leu Val Gln Phe Thr Ser Ala
            100                 105                 110

Ile Cys Ser Val Val Arg Arg Ala Phe Pro His Cys Leu Ala Phe Ser
        115                 120                 125

Tyr Met Asp Asp Ile Val Leu Gly Ala Lys Ser Val Gln His Leu Glu
    130                 135                 140

Ser Leu Tyr Thr Ala Val Thr Asn Phe Leu Leu Ser Leu Gly Ile His
145                 150                 155                 160

Leu Thr Pro Asn Lys Thr Lys Arg Trp Gly Tyr Ser Leu Asn Phe Met
                165                 170                 175

Gly Tyr Val Ile Gly
            180
```

<210> SEQ ID NO 53
<211> LENGTH: 160
<212> TYPE: PRT
<213> ORGANISM: artificial sequence
<220> FEATURE:
<223> OTHER INFORMATION: Synthetic peptide

<400> SEQUENCE: 53

```
Pro Ile Cys Pro Gly Tyr Arg Trp Met Cys Leu Arg Arg Phe Ile Ile
1               5                   10                  15

Ser Leu Phe Ile Leu Leu Leu Cys Leu Ile Phe Leu Leu Val Leu Leu
                20                  25                  30

Asp Tyr Gln Gly Met Leu Pro Val Cys Pro Leu Ile Pro Gly Ser Thr
            35                  40                  45

Thr Thr Ser Thr Gly Pro Cys Lys Thr Cys Thr Pro Ala Gln Gly
    50                  55                  60

Asn Ser Met Phe Pro Ser Cys Cys Thr Lys Pro Thr Asp Gly Asn
65                  70                  75                  80

Cys Thr Cys Ile Pro Ile Pro Ser Ser Trp Ala Phe Ala Lys Tyr Leu
                85                  90                  95

Trp Glu Trp Ala Ser Val Arg Phe Ser Trp Phe Ser Leu Leu Val Pro
                100                 105                 110

Phe Val Gln Trp Phe Val Gly Leu Ser Pro Thr Val Trp Leu Ser Ala
            115                 120                 125

Ile Trp Met Ile Leu Tyr Trp Gly Pro Ser Leu Tyr Asn Ile Leu Ser
    130                 135                 140

Pro Phe Ile Pro Leu Leu Pro Ile Phe Phe Cys Leu Trp Val Tyr Ile
145                 150                 155                 160
```

<210> SEQ ID NO 54
<211> LENGTH: 554
<212> TYPE: DNA
<213> ORGANISM: artificial sequence
<220> FEATURE:
<223> OTHER INFORMATION: Synthetic oligonucleotide

<400> SEQUENCE: 54

```
tccaatttgt cctgggtatc gctggatgtg tctgcggcgt tttatcatat tcctcttcat      60
cctgctgcta tgcctcatct tcttgttggt tcttctggac tatcaaggta tgttgcccgt     120
ttgtcctcta cttccaggaa catcaactac cagcacggga ccatgcaaga cctgcacgac     180
tcctgctcaa ggaaccctct atgtttccctc ttgttgctgt acaaaacctt cggacggaaa    240
ttgcacttgt attcccatcc catcgtcttg ggctttcgca agattcctat gggagtgggc     300
ctcagtccgt ttctcttggc tcartttact agtgccattt gttcagtggt tcgtagggct     360
ttccccccact gtttggcttt cagttatatt gatgatgtgg tattgggggc caagtctgta    420
caacatcttg aatcccttt tacctctatt accaattttc ttatgtcttt gggtatacat      480
ttaaaccta agaaaaccaa acgttggggc tactccctta acttcatggg atatgtaatt      540
ggaagttggg gtac                                                       554
```

<210> SEQ ID NO 55
<211> LENGTH: 184
<212> TYPE: PRT
<213> ORGANISM: artificial sequence
<220> FEATURE:
<223> OTHER INFORMATION: Synthetic peptide

<400> SEQUENCE: 55

```
Ser Asn Leu Ser Trp Val Ser Leu Asp Val Ser Ala Ala Phe Tyr His
1               5                   10                  15

Ile Pro Leu His Pro Ala Ala Met Pro His Leu Leu Val Gly Ser Ser
                20                  25                  30

Gly Leu Ser Arg Tyr Val Ala Arg Leu Ser Ser Thr Ser Arg Asn Ile
            35                  40                  45
```

-continued

Asn Tyr Gln His Gly Thr Met Gln Asp Leu His Asp Ser Cys Ser Arg
 50                  55                  60

Asn Leu Tyr Val Ser Leu Leu Leu Tyr Lys Thr Phe Gly Arg Lys
 65                  70                  75                  80

Leu His Leu Tyr Ser His Pro Ile Val Leu Gly Phe Arg Lys Ile Pro
                 85                  90                  95

Met Gly Val Gly Leu Ser Pro Phe Leu Leu Ala Gln Phe Thr Ser Ala
            100                 105                 110

Ile Cys Ser Val Val Arg Arg Ala Phe Pro His Cys Leu Ala Phe Ser
            115                 120                 125

Tyr Ile Asp Asp Val Val Leu Gly Ala Lys Ser Val Gln His Leu Glu
            130                 135                 140

Ser Leu Phe Thr Ser Ile Thr Asn Phe Leu Met Ser Leu Gly Ile His
145                 150                 155                 160

Leu Asn Pro Lys Lys Thr Lys Arg Trp Gly Tyr Ser Leu Asn Phe Met
                165                 170                 175

Gly Tyr Val Ile Gly Ser Trp Gly
            180

<210> SEQ ID NO 56
<211> LENGTH: 160
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (108)..(108)
<223> OTHER INFORMATION: Xaa = any amino acid

<400> SEQUENCE: 56

Pro Ile Cys Pro Gly Tyr Arg Trp Met Cys Leu Arg Arg Phe Ile Ile
 1               5                  10                  15

Phe Leu Phe Ile Leu Leu Leu Cys Leu Ile Phe Leu Leu Val Leu Leu
                20                  25                  30

Asp Tyr Gln Gly Met Leu Pro Val Cys Pro Leu Leu Pro Gly Thr Ser
            35                  40                  45

Thr Thr Ser Thr Gly Pro Cys Lys Thr Cys Thr Thr Pro Ala Gln Gly
 50                  55                  60

Thr Ser Met Phe Pro Ser Cys Cys Cys Thr Lys Pro Ser Asp Gly Asn
 65                  70                  75                  80

Cys Thr Cys Ile Pro Ile Pro Ser Ser Trp Ala Phe Ala Arg Phe Leu
                85                  90                  95

Trp Glu Trp Ala Ser Val Arg Phe Ser Trp Leu Xaa Leu Leu Val Pro
            100                 105                 110

Phe Val Gln Trp Phe Val Gly Leu Ser Pro Thr Val Trp Leu Ser Val
            115                 120                 125

Ile Leu Met Met Trp Tyr Trp Gly Pro Ser Leu Tyr Asn Ile Leu Asn
            130                 135                 140

Pro Phe Leu Pro Leu Leu Pro Ile Phe Leu Cys Leu Trp Val Tyr Ile
145                 150                 155                 160

<210> SEQ ID NO 57
<211> LENGTH: 1045
<212> TYPE: DNA
<213> ORGANISM: artificial sequence
<220> FEATURE:
<223> OTHER INFORMATION: Synthetic oligonucleotide -continued

<400> SEQUENCE: 57

```
cagcaaatcc gcctcctgcc tctaccaatc gccagtcagg aaggcagcct acccctctgt      60
ctccaccttt grgaaacact catcctcagg ccatgcagtg gaactccaca accttccacc     120
aaactctgcw agatcccaga gtgagaggcc tgtatttccc tgctggtggc tccagttcag     180
gaacagtaaa ccctgttccg acttctgtct ctcacacatc gtcaatcttc tcgaggattg     240
gggwccctgc gctgaacatg gagaacatca catcaggatt cctaggaccc ctgctcgtgt     300
tacaggcggg gttttcttg ttgacaagaa tcctcacaat accgcagagt ctagactcgt      360
ggtggacttc tctcaatttt ctaggggaa ctaccgtgtg tcttggccaa aattcgcagt      420
tcccaacctc caatcactca ccaacctcct gtcctccaac ttgwcctggt tatcgctgga     480
tgtrtctgcg gcgttttatc atcttcctct tcatcctgct gctatgcctc atcttcttgt     540
tggttcttct ggactatcaa ggtatgttgc ccgtttgtcc tctarttcca ggatcttcaa     600
ccaccagcac gggaccatgc agaacctgca cgactcctgc tcaaggaamc tctatgaatc     660
cctcctgttg ctgtaccaaa ccttcggacg gaaattgcac ctgtattccc atcccatcat     720
cctgggcttt cggaaaattc ctatgggagt gggcctcagc ccgtttctcc tgrctcagtt     780
tactagtgcc atttgttcag tggttcgtag ggctttcccc cactgtttgg ctttcagtta     840
tatggatgat gtggtattgg gggccaagtc tgtaymgcat cttragtccc tttttaccgc     900
tgttaccaat tttcttttgt ctytgggtat acatttaaac cctmacaaaa caaaaagatg     960
gggttactct ttacatttca tgggctatgt cattggatgt tatgggtcat tgccacaaga    1020
tcacatcaga cagaaaatca aagaa                                          1045
```

<210> SEQ ID NO 58
<211> LENGTH: 348
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (24)..(24)
<223> OTHER INFORMATION: Xaa = any amino acid
<220> FEATURE:
<221> NAME/KEY: MISC_FEATURE
<222> LOCATION: (155)..(155)
<223> OTHER INFORMATION: Xaa = any amino acid
<220> FEATURE:
<221> NAME/KEY: MISC_FEATURE
<222> LOCATION: (195)..(195)
<223> OTHER INFORMATION: Xaa = any amino acid
<220> FEATURE:
<221> NAME/KEY: MISC_FEATURE
<222> LOCATION: (216)..(216)
<223> OTHER INFORMATION: Xaa = any amino acid
<220> FEATURE:
<221> NAME/KEY: MISC_FEATURE
<222> LOCATION: (258)..(258)
<223> OTHER INFORMATION: Xaa = any amino acid
<220> FEATURE:
<221> NAME/KEY: MISC_FEATURE
<222> LOCATION: (292)..(292)
<223> OTHER INFORMATION: Xaa = any amino acid
<220> FEATURE:
<221> NAME/KEY: MISC_FEATURE
<222> LOCATION: (295)..(295)
<223> OTHER INFORMATION: Xaa = any amino acid
<220> FEATURE:
<221> NAME/KEY: MISC_FEATURE
<222> LOCATION: (315)..(315)
<223> OTHER INFORMATION: Xaa = any amino acid

<400> SEQUENCE: 58

```
Ser Lys Ser Ala Ser Cys Leu Tyr Gln Ser Pro Val Arg Lys Ala Ala
1               5                   10                  15

Tyr Pro Ser Val Ser Thr Phe Xaa Lys His Ser Ser Gly His Ala
            20                  25                  30

Val Glu Leu His Asn Leu Pro Pro Asn Ser Ala Arg Ser Gln Ser Glu
        35                  40                  45

Arg Pro Val Phe Pro Cys Trp Trp Leu Gln Phe Arg Asn Ser Lys Pro
50                  55                  60

Cys Ser Asp Phe Cys Leu Ser His Ile Val Asn Leu Leu Glu Asp Trp
65                  70                  75                  80

Gly Pro Cys Ala Glu His Gly Glu His His Ile Arg Ile Pro Arg Thr
                85                  90                  95

Pro Ala Arg Val Thr Gly Gly Val Phe Leu Val Asp Lys Asn Pro His
                100                 105                 110

Asn Thr Ala Glu Ser Arg Leu Val Val Asp Phe Ser Gln Phe Ser Arg
            115                 120                 125

Gly Asn Tyr Arg Val Ser Trp Pro Lys Phe Ala Val Pro Asn Leu Gln
130                 135                 140

Ser Leu Thr Asn Leu Leu Ser Ser Asn Leu Xaa Trp Leu Ser Leu Asp
145                 150                 155                 160

Val Ser Ala Ala Phe Tyr His Leu Pro Leu His Pro Ala Ala Met Pro
                165                 170                 175

His Leu Leu Val Gly Ser Ser Gly Leu Ser Arg Tyr Val Ala Arg Leu
                180                 185                 190

Ser Ser Xaa Ser Arg Ile Phe Asn His Gln His Gly Thr Met Gln Asn
            195                 200                 205

Leu His Asp Ser Cys Ser Arg Xaa Leu Tyr Glu Ser Leu Leu Leu Leu
        210                 215                 220

Tyr Gln Thr Phe Gly Arg Lys Leu His Leu Tyr Ser His Pro Ile Ile
225                 230                 235                 240

Leu Gly Phe Arg Lys Ile Pro Met Gly Val Gly Leu Ser Pro Phe Leu
                245                 250                 255

Leu Xaa Gln Phe Thr Ser Ala Ile Cys Ser Val Val Arg Arg Ala Phe
        260                 265                 270

Pro His Cys Leu Ala Phe Ser Tyr Met Asp Asp Val Val Leu Gly Ala
            275                 280                 285

Lys Ser Val Xaa His Leu Xaa Ser Leu Phe Thr Ala Val Thr Asn Phe
290                 295                 300

Leu Leu Ser Leu Gly Ile His Leu Asn Pro Xaa Lys Thr Lys Arg Trp
305                 310                 315                 320

Gly Tyr Ser Leu His Phe Met Gly Tyr Val Ile Gly Cys Tyr Gly Ser
                325                 330                 335

Leu Pro Gln Asp His Ile Arg Gln Lys Ile Lys Glu
                340                 345

<210> SEQ ID NO 59
<211> LENGTH: 311
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (24)..(24)
<223> OTHER INFORMATION: Xaa = any amino acid
<220> FEATURE:
```

```
<221> NAME/KEY: MISC_FEATURE
<222> LOCATION: (43)..(43)
<223> OTHER INFORMATION: Xaa = any amino acid
<220> FEATURE:
<221> NAME/KEY: MISC_FEATURE
<222> LOCATION: (81)..(81)
<223> OTHER INFORMATION: Xaa = any amino acid
<220> FEATURE:
<221> NAME/KEY: MISC_FEATURE
<222> LOCATION: (154)..(154)
<223> OTHER INFORMATION: Xaa = any amino acid
<220> FEATURE:
<221> NAME/KEY: MISC_FEATURE
<222> LOCATION: (161)..(161)
<223> OTHER INFORMATION: Xaa = any amino acid
<220> FEATURE:
<221> NAME/KEY: MISC_FEATURE
<222> LOCATION: (195)..(195)
<223> OTHER INFORMATION: Xaa = any amino acid
<220> FEATURE:
<221> NAME/KEY: MISC_FEATURE
<222> LOCATION: (216)..(216)
<223> OTHER INFORMATION: Xaa = any amino acid
<220> FEATURE:
<221> NAME/KEY: MISC_FEATURE
<222> LOCATION: (257)..(257)
<223> OTHER INFORMATION: Xaa = any amino acid
<220> FEATURE:
<221> NAME/KEY: MISC_FEATURE
<222> LOCATION: (292)..(292)
<223> OTHER INFORMATION: Xaa = any amino acid

<400> SEQUENCE: 59

Ala Asn Pro Pro Pro Ala Ser Thr Asn Arg Gln Ser Gly Arg Gln Pro
1               5                   10                  15

Thr Pro Leu Ser Pro Pro Leu Xaa Asn Thr His Pro Gln Ala Met Gln
            20                  25                  30

Trp Asn Ser Thr Thr Phe His Gln Thr Leu Xaa Asp Pro Arg Val Arg
        35                  40                  45

Gly Leu Tyr Phe Pro Ala Gly Gly Ser Ser Ser Gly Thr Val Asn Pro
    50                  55                  60

Val Pro Thr Ser Val Ser His Thr Ser Ser Ile Phe Ser Arg Ile Gly
65                  70                  75                  80

Xaa Pro Ala Leu Asn Met Glu Asn Ile Thr Ser Gly Phe Leu Gly Pro
                85                  90                  95

Leu Leu Val Leu Gln Ala Gly Phe Phe Leu Leu Thr Arg Ile Leu Thr
            100                 105                 110

Ile Pro Gln Ser Leu Asp Ser Trp Trp Thr Ser Leu Asn Phe Leu Gly
        115                 120                 125

Gly Thr Thr Val Cys Leu Gly Gln Asn Ser Gln Phe Pro Thr Ser Asn
    130                 135                 140

His Ser Pro Thr Ser Cys Pro Pro Thr Xaa Pro Gly Tyr Arg Trp Met
145                 150                 155                 160

Xaa Leu Arg Arg Phe Ile Ile Phe Leu Phe Ile Leu Leu Leu Cys Leu
                165                 170                 175

Ile Phe Leu Leu Val Leu Leu Asp Tyr Gln Gly Met Leu Pro Val Cys
            180                 185                 190

Pro Leu Xaa Pro Gly Ser Ser Thr Thr Ser Thr Gly Pro Cys Arg Thr
        195                 200                 205

Cys Thr Thr Pro Ala Gln Gly Xaa Ser Met Asn Pro Ser Cys Cys Cys
    210                 215                 220

Thr Lys Pro Ser Asp Gly Asn Cys Thr Cys Ile Pro Ile Pro Ser Ser
225                 230                 235                 240
```

```
-continued

Trp Ala Phe Gly Lys Phe Leu Trp Glu Trp Ala Ser Ala Arg Phe Ser
            245             250             255

Xaa Leu Ser Leu Leu Val Pro Phe Val Gln Trp Phe Val Gly Leu Ser
            260             265             270

Pro Thr Val Trp Leu Ser Val Ile Trp Met Met Trp Tyr Trp Gly Pro
        275             280             285

Ser Leu Tyr Xaa Ile Leu Ser Pro Phe Leu Pro Leu Leu Pro Ile Phe
    290             295             300

Phe Cys Leu Trp Val Tyr Ile
305             310
```